(12) United States Patent
Watson et al.

(10) Patent No.: US 6,326,386 B1
(45) Date of Patent: Dec. 4, 2001

(54) BENZAMIDE DERIVATIVES AS THROMBIN INHIBITORS

(75) Inventors: Nigel Stephen Watson; Martin Pass; Vipulkumar Patel, all of Stevenage (GB)

(73) Assignee: Glaxo Group Limited, Greenford (GB)

( * ) Notice: Subject to any disclaimer, the term of this patent is extended or adjusted under 35 U.S.C. 154(b) by 0 days.

(21) Appl. No.: 09/678,610

(22) Filed: Oct. 4, 2000

Related U.S. Application Data

(63) Continuation of application No. 09/077,885, filed as application No. PCT/EP96/05143 on Dec. 13, 1996, now abandoned.

(30) Foreign Application Priority Data

Dec. 15, 1995 (GB) .................................................. 9525620

(51) Int. Cl.$^7$ ........................ C07D 213/02; A61K 31/44
(52) U.S. Cl. ............................................................ 514/352
(58) Field of Search .............................. 546/309; 514/352

(56) References Cited

U.S. PATENT DOCUMENTS 5,556,977 9/1996 Wayne .................................. 544/360

FOREIGN PATENT DOCUMENTS

WO 94 20467A 9/1994 (WO) .

OTHER PUBLICATIONS

Chem Rev., 1996, pp. 3170–3171, 3176, XP002027890 Patani et al.: "A Rational Approach in Drug Design", Reference on p. 2171 show that the general concept of the citations (listed on p. 3176) was known well before the priority date.

Primary Examiner—Zinna Northington Davis
(74) Attorney, Agent, or Firm—Bacon & Thomas

(57) ABSTRACT

The invention relates to a novel class of amide derivatives which act as thrombin inhibitors as described by formula (I), where $R^1$ and $R^2$, independently represent a group (a) or $R^1$ and $R^2$ together form a $C_{3-7}$ heterocycloalkyl or heterocycloalkenyl group which may be optionally substituted by $C_{1-6}$ alkyl, $C_{1-4}$ alkoxy, halogen, carboxylic acid or a $C_{1-4}$ carboxylic acid ester group; $R^3$ represents hydrogen, $C_{1-3}$ alkyl, halogen, or $C_{1-2}$ alkoxy; $R^4$, $R^5$ and $R^6$ independently represent hydrogen, or halogen; $R^7$ represents hydrogen or $C_{1-6}$ alkyl; $R^8$ represents hydrogen, $C_{3-7}$ cycloalkyl, $C_{3-7}$ cycloalkenyl, $C_{3-7}$ heterocycloalkyl, $C_{3-7}$ heterocycloalkenyl, aryl or heteroaryl, which groups are optionally substituted by one or more groups selected from halogen, hydroxy, CN, $C_{1-6}$ alkyl, $C_{1-6}$ alkoxy, $C_{1-6}$ acyloxy, $NR^9R^{10}$, $NHCOR^{11}$, $NHSO_2R^{12}$, $COR^{13}$, $CO_2R^{14}$, $CONR^{15}R^{16}$, and $SO_2NHR^{17}$; X represents a bond, a $C_{1-6}$ alkyl chain, or a $C_{3-6}$ alkenyl chain, where one or two nitrogen, oxygen, or sulfur atoms may be optionally contained within each chain, and the chains are optionally substituted by one or more groups selected from halogen, hydroxy, CN, $C_{1-6}$ alkyl, $C_{1-6}$ alkoxy, $C_{1-6}$ acyloxy, $NR^9R^{10}$, $NHCOR^{11}$, $NHSO_2R^{12}$, $COR^{13}$, $CO_2R^{14}$, $CONR^{15}R^{16}$, and $SO_2NHR^{17}$; $R^9$–$R^{17}$ represent hydrogen, $C_{1-6}$ alkyl, or $R^9$ and $R^{10}$ or $R^{15}$ and $R^{16}$ form a $C_{3-7}$ heterocycloalkyl ring, or $R^{12}$ additionally may represent trifluoromethyl; and pharmaceutically acceptable derivatives or solvates thereof, to processes for their preparation; and their use in the treatment of clinical conditions susceptible to amelioration by administration of a thrombin inhibitor.

14 Claims, No Drawings

BENZAMIDE DERIVATIVES AS THROMBIN INHIBITORS

This application is a continuation application of U.S. application Ser. No. 09/077,885, filed Jun. 12, 1998 now abandoned, which is a 371 of PCT/EP96/05743, filed on Dec. 13, 1996.

This invention relates to a new class of chemical compounds and to their use in medicine. In particular, the invention concerns novel amide derivatives, methods for their preparation, pharmaceutical compositions containing them and their use as thrombin inhibitors. Thrombin inhibitors have been described previously in, for example, WO94/20467.

Thrombin is a serine proteinase present in plasma and is formed by conversion from its prothrombin precursor by the action of Factor Xa. Thrombin plays a central role in the mechanism of blood coagulation by converting the soluble plasma protein; fibrinogen, into insoluble fibrin. The insoluble fibrin matrix is required for the stabilisation of the primary hemostatic plug. Many significant disease states are related to abnormal hemostasis. With respect to the coronary arterial vasculature, abnormal thrombus formation due to the rupture of an established atherosclerotic plaque is the major cause of acute myocardial infarction and unstable angina. Both treatment of an occlusive coronary thrombus by thrombolytic therapy and percutaneous transluminal coronary angioplasty (PTCA) are often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterised by the rapid consumption of coagulation factors and systemic coagulation which results in the formation of life-threatening thrombi occurring throughout the vasculature leading to widespread organ failure.

Beyond its direct role in the formation of fibrin rich blood clots, thrombin has been reported to have profound bioregulatory effects on a number of cellular components within the vasculature and blood, (Shuman, M. A., Ann. NY Acad. Sci., 405: 349 (1986)).

The inhibition of thrombin has been implicated as a potential treatment for a number of disease states. Thrombin inhibitors may be useful in the treatment of acute vascular diseases such as coronary thrombosis, stroke, pulmonary embolism, deep vein thrombosis, restenosis, atrial fibrillation, myocardial infarction, and unstable angina. They have been described as anti-coagulant agents both in-vivo and ex-vivo, and in oedema and inflammation, whereby a low dose of thrombin inhibitor can reduce platelet and endothelial cell thrombin mediated inflammatory responses without concomitant anticoagulant effects. Thrombin has been reported to contribute to lung fibroblast proliferation, thus, thrombin inhibitors could be useful for the treatment of some pulmonary fibrotic diseases. Thrombin inhibitors have also been reported in the treatment of tumour metastasis whereby the thrombin inhibitor prevents the fibrin deposition and metastasis caused by the inappropriate activation of Factor X by cysteine proteinases produced by certain tumour cells. They have been shown to inhibit neurite retraction and thus may have potential in neurogenerative diseases such as Parkinson's and Alzheimer's disease. They have also been reported to be used in conjunction with thrombolytic agents by permitting the use of a lower dose of thrombolytic agent. Other potential uses have been described in U.S. Pat. No. 5,371,091 for the treatment of Kasabach Merritt Syndrome and hemolytic uremic syndrome, in EP565897 for the prevention of fibrin deposits in the eye during ophthalmic surgery, and in DE4126277 for the treatment of osteoporosis.

Thus, we have now found a novel class of amide derivatives which act as thrombin inhibitors shown as formula (1)

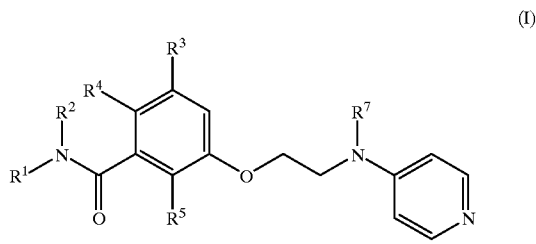

(I)

where
$R^1$ and $R^2$ independently represent a group

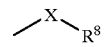

or $R^1$ and $R^2$ together form a $C_{3-7}$ heterocycloalkyl or heterocycloalkenyl group which may be optionally substituted by $C_{1-6}$ alkyl, $C_{1-4}$ alkoxy, halogen, carboxylic acid or a $C_{1-4}$ carboxylic acid ester group;

$R^3$ represents hydrogen, $C_{1-3}$ alkyl, halogen, or $C_{1-2}$ alkoxy;

$R^4$, $R^5$ and $R^6$ independently represent hydrogen, or halogen;

$R^7$ represents hydrogen or $C_{1-6}$ alkyl;

$R^8$ represents hydrogen, $C_{3-7}$ cycloalkyl, $C_{3-7}$ cycloalkenyl, $C_{3-7}$ heterocycloalkyl, $C_{3-7}$ heterocycloalkenyl, aryl, or heteroaryl, which groups are optionally substituted by one or more groups selected from halogen, hydroxy, CN, $C_{1-6}$ alkyl, $C_{1-6}$ alkoxy, $C_{1-6}$ acyloxy, $NR^9R^{10}$, $NHCOR^{11}$, $NHSO_2R^{12}$, $COR^{13}$, $CO_2R^{14}$, $CONR^{15}R^{16}$, and $SO_2NHR^{17}$;

X represents a bond, a $C_{1-6}$ alkyl chain, or a $C_{3-6}$ alkenyl chain, where one or two nitrogen, oxygen, or sulfur atoms may be optionally contained within each chain, and the chains are optionally substituted by one or more groups selected from halogen, hydroxy, CN, $C_{1-6}$ alkyl, $C_{1-6}$ alkoxy, $C_{1-6}$ acyloxy, $NR^9R^{10}$, $NHCOR^{11}$, $NHSO_2R^{12}$, $COR^{13}$, $CO_2R^{14}$, $CONR^{15}R^{16}$, and $SO_2NHR^{17}$;

$R^9$–$R^{17}$ represent hydrogen, $C_{1-6}$ alkyl, or $R^9$ and $R^{10}$ or $R^{15}$ and $R^{16}$ form a $C_{3-7}$ heterocycloalkyl ring, or $R^{12}$ additionally may represent trifluoromethyl;

and pharmaceutically acceptable derivatives or solvates thereof.

Referring to the general formula (I), alkyl includes both straight and branched chain saturated hydrocarbon groups.

Referring to the general formula (I), alkenyl includes both straight and branched chain hydrocarbon groups with at least one double bond.

Referring to the general formula (I), aryl includes optionally substituted monocyclic or bicyclic aromatic carbocyclic groups such as phenyl and naphthyl.

Referring to the general formula (I), heteroaryl includes 5 or 6 membered aromatic heterocyclic rings containing one or more heteroatoms selected from nitrogen, sulphur and oxygen atoms, and fused bicyclic ring systems containing one or more nitrogen, sulfur, and oxygen atoms. Examples of such groups include oxadiazole, thiazole. thiadiazole, triazole, tetrazole, benzimidazole, pyridine, furan and thiophene.

Referring to the general formula (I), examples of $C_{3-7}$ cycloalkyl groups include cyclohexyl and cyclopentyl groups.

Referring to the general formula (I), a $C_{3-7}$ cycloalkenyl group includes rings containing at least one double bond incorporated in the ring.

Referring to the general formula (I), a $C_{3-7}$ heterocycloalkyl group includes rings containing containing one or more heteroatoms selected from nitrogen, sulphur and oxygen atoms, for example, a tetrahydropyran-4-yl group.

Referring to the general formula (I), a $C_{3-7}$ heterocycloalkenyl group includes rings containing one or more heteroatoms selected from nitrogen, sulphur and oxygen atoms, together with at least on double bond incorporated in the ring.

Referring to the general formula (I) where $R^1$ represents a group

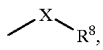

X is suitably a bond or $C_{1-6}$ alkyl group, e.g. methyl, isopropyl or isobutyl, and $R^8$ suitably represents hydrogen, $C_{3-7}$ cycloalkyl, aryl, or heteroaryl. When X represents a bond, $R^8$ is preferably phenyl optionally substuituted by one or more halogen groups, or $C_{3-7}$ cycloalkyl, e.g. cyclobutyl, cyclopentyl or cyclohexyl. When X represents. a $C_{1-6}$ alkyl group, $R^8$ is preferably hydrogen, cycloalkyl, e.g. cyclohexyl, or heteroaryl, e.g. thienyl or furyl.

Referring to the general formula (l) where $R^2$ represents a group

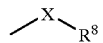

X is suitably $C_{3-6}$ alkenyl, e.g. allyl, or $C_{1-6}$ alkyl, e.g. methyl, ethyl, propyl or pentyl, which optionally contains an oxygen group within the chain and is optionally substituted by a group selected from hydroxy, $C_{1-6}$ alkoxy, $NHSO2R^{12}$, $CO_2R^{14}$, $CONR^{15}R^{16}$, or $SO_2NHR^{17}$, and $R^8$ is suitably hydrogen, $C_{3-7}$ heterocycloalkyl, e.g. pyrrolidine or morpholine, aryl, e.g. phenyl which is optionally substituted by $CO_2R^{14}$, or heteroaryl, e.g. oxadiazole optionally substituted by hydroxy, triazole, or tetrazole optionally substituted by $C_{1-6}$ alkyl.

$R^3$ is preferably $C_{1-3}$ alkyl, e.g. methyl, or halogen, e.g. chlorine or bromine.

$R^4$, $R^5$ and $R^6$ are preferably hydrogen, or halogen, e.g. fluorine.

$R^7$ is preferably hydrogen.

A preferred subclass of the compounds of formula (I) is defined by compounds of formula (IA)

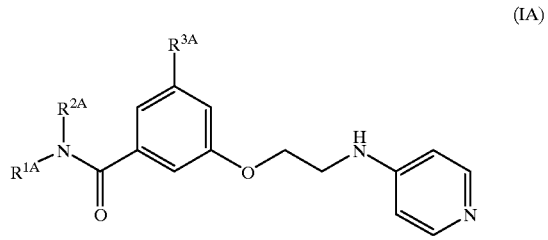

where
$R^{1A}$ represents a group

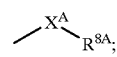

$X^A$ represents a bond or $C_{1-6}$ alkyl;
$R^{8A}$ represents hydrogen, $C_{3-7}$ cycloalkyl, aryl optionally substituted by halogen, or heteroaryl;
$R^{2A}$ represents a group

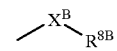

$X^B$ represents $C_{1-6}$ alkyl optionally substituted by $CO^2R^{14A}$
$R^{8B}$ represents hydrogen, phenyl substituted by $CO_2R^{14A}$, oxadiazole substituted by a hydroxy group, or an unsubstituted C-linked tetrazole group;
$R^{3A}$ represents $C_{1-3}$ alkyl or halogen;
and pharmaceutically acceptable derivatives or solvates thereof.

Suitable compounds of general formula (I) for use according to the invention are;
N-Cyclohexyl-3,N-dimethyl-5-[2-(pyridin-4-ylamino)-ethoxy]-benzamide;
3-Chloro-N-cyclohexyl-N-methyl-5-[2-pyridin-4-ylamino)-ethoxy]-benzamide;
3-Bromo-N-cyclohexyl-N-methyl-5-[2-(pyridin-4-ylamino)-ethoxy]-benzamide;
N-Allyl-3-chloro-N-cyclohexyl-5-[2-(pyridin-4-ylamino)-ethoxy]-benzamide;
N-Allyl-3-bromo-N-cyclohexyl-5-[2-(pyridin-4-ylamino)-ethoxy]-benzamide;
({3-Chloro-5-[2-(pyridin-4-ylamino)ethoxy]-benzoyl}-cyclohexyl-amino)-acetic acid;
({3-Bromo-5-[2-(pyridin-4-ylamino)ethoxy]-benzoyl}-cyclohexyl-amino)-acetic acid;
N-Allyl-3-chloro-N-cyclopentyl-5-[2-(pyridin-4-ylamino)-ethoxy]-benzamide;
N-Allyl-3-bromo-N-cyclopentyl-5-[2-(pyridin-4-ylamino)-ethoxy]-benzamide;
3-Chloro-N-propyl-5-[2-(pyridin-4-ylamino)-ethoxy]-N-(tetrahydro-pyran-4-yl)-benzamide;
3-Bromo-N-propyl-5-[2-(pyridin-4-ylamino)-ethoxy]-N-(tetrahydro-pyran-4-yl)-benzamide;
3-Chloro-N-propyl-N-pyridin-3-yl-5-[2-(pyridin-4-ylamino)-ethoxy]-benzamide;
3-Bromo-N-propyl-N-pyridin-3-yl-5-[2-(pyridin-4-ylamino)-ethoxy]-benzamide;

3-Chloro-N-(3,5-difluorophenyl)-N-propyl-5-[2-(pyridin-4-ylamino)-ethoxy]-benzamide;

3-Bromo-N-(3,5-difluorophenyl)-N-propyl-5-[2-(pyridin-4-ylamino)-ethoxy]-benzamide;

2-[{3-Chloro-5-[2-(pyridin-4-ylamino)-ethoxy]-benzoyl}-(2,4-difluoro-benzyl)-amino]-butyric acid;

4-[({3-Chloro-5-[2-(pyridin-4-ylamino)-ethoxy]-benzoyl}-isobutyl-amino)-methyl]-benzoic acid;

4-[2-({3-Chloro-5-[2-(pyridin-4-ylamino)-ethoxy]-benzoyl}-isobutyl-amino)-ethyl]-benzoic acid;

3-Chloro-N-cyclopentyl-5-[2-(pyridin-4-ylamino)-ethoxy]-N-(3-trifluoromethanesulfonylamino-propyl)-benzamide;

3-Chloro-N-isopropyl-N-methyl-5-[2-(pyridin-4-ylamino)-ethoxy]-benzamide;

N-[2-(3-Amino-[1,2,4]oxadiazol-5-yl)ethyl]-3-chloro-N-isopropyl-5-[2-(pyridin-4-ylamino)-ethoxy]-benzamide;

N-(2-Carbamoyl-ethyl)-N-isopropyl-3-methyl-5-[2-(pyridin-4-ylamino)-ethoxy]-benzamide;

N-(2-Carbamoyl-ethyl)-3-chloro-N-cyclopropylmethyl-5-[2-(pyridin-4-ylamino)-ethoxy]-benzamide;

N-(2-Carbamoyl-ethyl)-3-chloro-5-[2-(pyridin-4-ylamino)-ethoxy]-N-(tetrahydrofuran-2-ylmethyl)-benzamide;

N-(2-Carbamoyl-ethyl)-3-chloro-N-(2,2-dimethyl-propyl)-5-[2-(pyridin-4-ylamino)-ethoxy]-benzamide;

N-(2-Carbamoyl-ethyl)-3-chloro-N-isopropyl-5-[2-(pyridin-4-ylamino)-ethoxy]-benzamide;

N-2-Carbamoyl-ethyl)-3-chloro-N-isobutyl-5-[2-(pyridin-4-ylamino)-ethoxy]-benzamide;

6-[{3-Chloro-5-[2-(pyridin-4-ylamino)-ethoxy]-benzoyl}-(2-fluoro-benzyl)-amino]-hexanoic acid;

6-({3-Chloro-5-[2-(pyridin-4-ylamino)-ethoxy]-benzoyl}-isobutyl-amino)-hexanoic acid;

6-[{3-Chloro-5-[2-(pyridin-4-ylamino)-ethoxy]-benzoyl}-(2-methoxyethyl)-amino]-hexanoic acid;

6-({3-Chloro-5-[2-(pyridin-4-ylamino)-ethoxy]-benzoyl}-cyclohexylmethyl-amino)-hexanoic acid;

6-[{3-Chloro-5-[2-(pyridin-4-ylamino)-ethoxy]-benzoyl}-(3-fluoro-benzyl)-amino]-hexanoic acid;

6-({3-Chloro-5-[2-(pyridin-4-ylamino)-ethoxy]-benzoyl}-pyridin-4-ylmethyl-amino)-hexanoic acid;

N-(5-Carbamoyl-pentyl)-3-chloro-N-furan-2-ylmethyl-5-[2-(pyridin-4-ylamino)-ethoxy]-benzamide;

N-5-Carbamoyl-pentyl)-3-chloro-5-[2-(pyridin-4-ylamino)-ethoxy]-N-(2,2,2-trifluoroethyl)-benzamide;

N-(5-Carbamoyl-pentyl)-3-chloro-N-(2-fluoro-benzyl)-5-[2-(pyridin-4-ylamino)-ethoxy]-benzamide;

N-(5-Carbamoyl-pentyl)-3-chloro-N-(2-methoxy-ethyl)-5-[2-(pyridin-4-ylamino)-ethoxy]-benzamide;

N-(5-Carbamoyl-pentyl)-3-chloro-N-cyclohexylmethyl-5-[2-(pyridin-4-ylamino)-ethoxy]-benzamide;

N-(5-Carbamoyl-pentyl)-3-chloro-N-isobutyl-5-[2-(pyridin-4-ylamino)-ethoxy]-benzamide;

N-(5-Carbamoyl-pentyl)-3-chloro-5-[2-(pyridin-4-ylamino)-ethoxy]-N-thiophen-2-ylmethyl-benzamide;

1-{3-Chloro-5-[2-(pyridin-4-ylamino)-ethoxy]-benzoyl}-piperidine-2-carboxylic acid;

4-({3-Chloro-5-[2-(pyridin-4-ylamino)-ethoxy]-benzoyl}-cyclobutyl-amino)-butyric acid;

4-({3-Chloro-5-[2-(pyridin-4-ylamino)-ethoxy]-benzoyl}-furan-2-ylmethyl-amino)-butyric acid;

4-[{3-Chloro-5-[2-(pyridin-4-ylamino)-ethoxy]-benzoyl}-(3-fluoro-benzyl)-amino]-butyric acid;

{3-Chloro-5-[2-(pyridin-4-ylamino)-ethoxy]-phenyl}-(2-methyl-piperidin-1-yl)-methanone;

3-Chloro-N-(2-diethylcarbamoyl-ethyl)-N-isopropyl-5-[2-(pyridin-4-ylamino)-ethoxy]-benzamide;

3-Chloro-N-isopropyl-N-(3-methanesulfonylamino-propyl)-5-[2-(pyridin-4-ylamino)-ethoxy]-benzamide;

3-Chloro-N-isopropyl-N-[3-(propane-1-sulfonylamino)-propyl]-5-[2-(pyridin-4-ylamino)-ethoxy]-benzamide;

3-Chloro-N-isopropyl-N-(3-oxo-3-piperidin-1-yl-propyl)-5-[2-(pyridin-4-ylamino)-ethoxy]-benzamide;

3-Chloro-N-[2-(ethyl-methyl-carbamoyl)-ethyl]-N-isopropyl-5-[2-(pyridin-4-ylamino)-ethoxy]-benzamide;

3-Chloro-N-isopropyl-N-(3-oxo-3-pyrrolidin-1-yl-propyl)-5-[2-(pyridin-4-ylamino)-ethoxy]-benzamide;

3-Chloro-N-isopropyl-N-(3-morpholin-4-yl-3-oxo-propyl)-5-[2-(pyridin-4-ylamino)-ethoxy]-benzamide mixture with 3-({3-chloro-5-[2-(pyridin-4-ylamino)-ethoxy]-benzoyl}-isopropyl-amino)-propionic acid (1:2);

N-(2-tert-Butylcarbamoyl-ethyl)-3-chloro-N-isopropyl-5-[2-(pyridin-4-ylamino)-ethoxy]-benzamide;

3-Chloro-N-[2-(2,2-dimethyl-propylcarbamoyl)-ethyl]-N-isopropyl-5-[2-(pyridin-4-ylamino)-ethoxy]-benzamide;

3-Chloro-N-isopropyl-N-(3-oxo-3-thiomorpholin-4-yl-propyl)-5-[2-(pyridin-4-ylamino)-ethoxy]-benzamide;

3-Chloro-N-isopropyl-N-(3-oxo-3-thiazolidin-3-yl-propyl)-5-[2-(pyridin-4-ylamino)-ethoxy]-benzamide;

3-Chloro-N-(3-ethanesulfonylamino-propyl)-N-isopropyl-5-[2-(pyridin-4-ylamino)-ethoxy]-benzamide;

3-Chloro-N-isopropyl-N-[3-propane-2-sulfonylamino)-propyl]-5-[2-(pyridin-4-ylamino)-ethoxy]-benzamide;

3-Chloro-N-(4-fluoro-phenyl)-5-[2-(pyridin-4-ylamino)-ethoxy]-N-(3-[1,2,4]triazol-1-yl-propyl)-benzamide;

3-Chloro-N-cyclopentyl-5-[2-(pyridin-4-ylamino)-ethoxy]-N-(2-[1,2,4]triazol-1-yl-ethyl)-benzamide;

3-Chloro-N-cyclopentyl-5-[2-(pyridin-4-ylamino)-ethoxy]-N-(4-[1,2,4]triazol-1-yl-butyl)-benzamide;

3-Chloro-N-(4-fluoro-phenyl)-5-[2-(pyridin-4-ylamino)-ethoxy]-N-(3-tetrazol-2-yl-propyl)-benzamide;

3-Chloro-N-(3-fluoro-phenyl)-5-[2-(pyridin-4-ylamino)-ethoxy]-N-(3-tetrazol-2-yl-propyl)-benzamide;

3-Chloro-N-2-fluoro-phenyl)-5-[2-(pyridin-4-ylamino)-ethoxy]-N-(3-tetrazol-2-yl-propyl)-benzamide;

3-Chloro-N-phenyl-5-[2-(pyridin-4-ylamino)-ethoxy]-N-(2-tetrazol-2-yl-ethyl)-benzamide;

3-Chloro-N-phenyl-5-[2-(pyridin-4-ylamino)-ethoxy]-N-(2-[1,2,3]triazol-2-yl-(ethyl)-benzamide;

3-Chloro-N-phenyl-5-[2-(pyridin-4-ylamino)-ethoxy]-N-[2-(pyridin-2-yloxy)-ethyl]-benzamide;

3-Chloro-N-isopropyl-N-(2-methoxy-ethyl)-5-[2-(pyridin-4-ylamino)-ethoxy]-benzamide;

6-([3-Chloro-5-[2-(pyridin-4-ylamino)-ethoxy]-benzoyl]-thiophen-2-ylmethyl-amino)-hexanoic acid;

6-[{3-Chloro-5-[2-(pyridin-4-ylamino)-ethoxy]-benzoyl}-(2-methyl-butyl)-amino]-hexanoic acid;

{3-Chloro-5-[2-(pyridin-4-ylamino)-ethoxy]-phenyl}-(2,5-dimethyl-pyrrolidin-1-yl)-methanone;

4-({3-Chloro-5-[2-(pyridin-4-ylamino)-ethoxy]-benzoyl}-naphthalen-1-ylmethyl-amino)-butyric acid;
4-[{3-Chloro-5-[2-(pyridin-4-ylamino)-ethoxy]-benzoyl}-(1-methyl-1H-benzoimidazol-2-yl)-amino]-butyric acid;
3-Chloro-N-isopropyl-5-[2-(pyridin-4-ylamino)-ethoxy]-N-3-trifluoromethanesulfonylamino-propyl)-benzamide;
N-3-Amino-propyl)-3-chloro-N-isopropyl-5-[2-(pyridin-4-ylamino)-ethoxy]-benzamide;
({3-Chloro-5-[2-(pyridin-4-ylamino)ethoxy]-benzoyl}-cyclopentyl-amino)-acetic acid;
3-Chloro-N-cyclopentyl-N-propyl-5-[2-(pyridin-4-ylamino)-ethoxy]-benzamide;
3-Chloro-N-cyclopentyl-N-(3-hydroxy-propyl)-5-[2-(pyridin-4-ylamino)-ethoxy]-benzamide;
3-Chloro-N-propyl-5-[2-(pyridin-4-ylamino)-ethoxy]-N-(tetrahydro-pyran-4-yl)-benzamide;
3-Chloro-N-cyclopentyl-N-(2,3-dihydroxy-propyl)-5-[2-(pyridin-4-ylamino)-ethoxy]-benzamide;
3-Chloro-N-cyclopentyl-N-(3-morpholin-4-yl-propyl)-5-[2-(pyridin-4-ylamino)-ethoxy]-benzamide;
4-({3-Chloro-5-[2-(pyridin-4-ylamino)-ethoxy]-benzoyl}-cyclopentyl-amino)-butyric acid ethyl ester;
3-Chloro-N-cyclopentyl-5-[2-(pyridin-4-ylamino)-ethoxy]-N-(3-pyrrolidin-1-yl-propyl)-benzamide;
N-(3-Carbamoyl-propyl)-3-chloro-N-cyclopentyl-5-[2-(pyridin-4-ylamino)-ethoxy]-benzamide;
N-(2-Carbamoyl-ethyl)-3-chloro-N-cyclopentyl-5-[2-(pyridin-4-ylamino)-ethoxy]-benzamide;
N-Carbamoylmethyl-3-chloro-N-cyclopentyl-5-[2-(pyridin-4-ylamino)-ethoxy]-benzamide;
3-chloro-N-ethyl-N-phenyl-5-[2-(pyridin-4-ylamino)-ethoxy]-benzamide;
N-(2-Carbamoyl-ethyl)-3-chloro-N-cyclopropyl-5-[2-(pyridin-4-ylamino)-ethoxy]-benzamide;
3-Chloro-N,N-dipropyl-5-[2(pyridin-4-ylamino)-ethoxy]-benzamide;
4-({3-Chloro-5-[2-(pyridin-4-ylamino)-ethoxy]-benzoyl}-cyclopentyl-amino)-butyric acid;
N-(2-Carbamoyl-ethyl)-3-chloro-N-phenyl-5-[2-(pyridin-4-ylamino)-ethoxy]-benzamide;
N-(2-Carbamoyl-ethyl)-3-chloro-N-(2-chloro-phenyl)-5-[2-(pyridin-4-ylamino)-ethoxy]-benzamide;
N-(2-Carbamoyl-ethyl)-3-chloro-N-(2-fluoro-phenyl)-5-[2-(pyridin-4-ylamino)-ethoxy]-benzamide;
4-[{3-Chloro-5-[2-(pyridin-4-ylamino)-ethoxy]-benzoyl}-(2-fluoro-phenyl)-amino]-butyric acid methyl ester;
4-[{3-Chloro-5-[2-(pyridin-4-ylamino)-ethoxy]-benzoyl}-(2-fluoro-phenyl)-amino]-butyric acid;
3-Chloro-N-(2-fluoro-phenyl)-N-(4-oxo-4-pyrrolidin-1-yl-butyl)-5-[2-(pyridin-4-ylamino)-ethoxy]-benzamide;
N-(3-Carbamoyl-propyl)-3-chloro-N-(2-fluoro-phenyl)-5-[2-(pyridin-4-ylamino)-ethoxy]-benzamide;
4-((2-Carbamoyl-phenyl)-{3-chloro-5-[2-(pyridin-4-ylamino)-ethoxy]-benzoyl}-amino)-butyric acid methyl ester;
4-((2-Carbamoyl-phenyl)-{3-chloro-5-[2-(pyridin-4-ylamino)-ethoxy]-benzoyl}-amino)-butyric acid;
3-Chloro-N-(2-fluoro-phenyl)-5-[2-(pyridin-4-ylamino)-ethoxy]-N-[3-(1H-tetrazol-5-yl)-propyl]-benzamide;
3-Chloro-N-[2-(2,3-dihydroxy-propoxy)-ethyl]-N-(2-fluoro-phenyl)-5-[2-(pyridin-4-ylamino-ethoxy]-benzamide;
(R)-1-{3-[{3-Chloro-5-[2-(pyridin-4-ylamino)-ethoxy]-benzoyl}-(2-fluoro-phenyl)-amino]-propyl}-pyrrolidine-2-carboxylic acid;
3-Chloro-N-phenyl-5-[2-(pyridin-4-ylamino)-ethoxy]-N-(2-sulfamoyl-ethyl)-benzamide;
3-Chloro-N-[2-(ethyl-methyl-carbamoyl)-ethyl]-N-phenyl-5-[2-(pyridin-4-ylamino)-ethoxy]-benzamide;
3-Chloro-N-[2-(ethyl-methyl-carbamoyl)-ethyl]-N-phenyl-5-[2-(pyridin-4-ylamino)-ethoxy]-benzamide;
N-(2-tert-Butylcarbamoyl-ethyl)-3-chloro-N-phenyl-5-[2-(pyridin-4-ylamino)-ethoxy]-benzamide;
3-Chloro-N-[2-(2,2-dimethyl-propylcarbamoyl)-ethyl]-N-phenyl-5-[2-(pyridin-4-ylamino)-ethoxy]-benzamide;
3-Chloro-N-(3-oxo-3-thiomorpholin-4-yl-propyl)-N-phenyl-5-[2-(pyridin-4-ylamino)-ethoxy]-benzamide;
3-Chloro-N-(3-oxo-3-thiazolidin-3-yl-propyl)-N-phenyl-5-[2-(pyridin-4-ylamino)-ethoxy]-benzamide;
3-Chloro-N-isopropyl-N-[2-(1-methyl-1H-tetrazol-5-yl)-ethyl]-5-[2-(pyridin-4-ylamino)-ethoxy]-benzamide;
3-Chloro-N-(3,5-difluoro-phenyl)-N-propyl-5-[2-(pyridin-4-ylamino)-ethoxy]-benzamide;
3-Chloro-N-(3-morpholin-4-yl-propyl)-5-[2-(pyridin-4-ylamino)-ethoxy]-N-(tetrahydro-pyran-4-yl)-benzamide;
3-Chloro-5-[2-(pyridin-4-ylamino)-ethoxy]-N-(3-pyrrolidin-1-yl-propyl)-N-(tetrahydro-pyran-4-yl)-benzamide;
N-(2-Carbamoyl-ethyl)-3-chloro-N-(1-propyl-butyl)-5-[2-(pyridin-4-ylamino)-ethoxy]-benzamide;
3-Chloro-N-cyclopentyl-N-(4-oxo-4-pyrrolidin-1-yl-butyl)-5-[2-(pyridin-4-ylamino)-ethoxy]-benzamide;
3-Chloro-N-ethyl-N-(2-fluoro-phenyl)-5-[2-(pyridin-4-ylamino)-ethoxy]-benzamide;
3-Chloro-N-propyl-5-[2-(pyridin-4-ylamino)-ethoxy]-N-[1,3,4]thiadiazol-2-yl-benzamide;
3-Chloro-N-propyl-5-[2-(pyridin-4-ylamino)-ethoxy]-N-thiazol-2-yl-benzamide;
3-Chloro-N-[2-(2,3-dihydroxy-propoxy)-ethyl]-N-phenyl-5-[2-(pyridin-4-ylamino)-ethoxy]-benzamide;
N-(2-tert-Butylsulfamoyl-ethyl)-3-chloro-N-phenyl-5-[2-(pyridin-4-ylamino-ethoxy]-benzamide;
3-Chloro-N-(2-isopropylsulfamoyl-ethyl)-N-phenyl-5-[2-(pyridin-4-ylamino)-ethoxy]-benzamide;
3-Chloro-N-isopropyl-5-[2-(pyridin-4-ylamino)-ethoxy]-N-[2-(pyridin-2-yloxy)-ethyl]-benzamide;
3-Chloro-N-[2-(2,3-dihydroxy-propoxy)-ethyl]-N-(4-fluoro-phenyl)-5-[2-(pyridin-4-ylamino)-ethoxy]-benzamide;
3-Chloro-N-cyclopentyl-5-[2-(pyridin-4-ylamino)-ethoxy]-N-[2-(1H-tetrazol-5-yl)-ethyl]-benzamide;
3-Chloro-N-isopropyl-5-[2-(pyridin-4-ylamino)-ethoxy]-N-(2-[1,2,4]triazol-1-yl-ethyl)-benzamide;
3-Chloro-N-[2-(3-methyl-but-2-yl-carbamoyl)-ethyl]-N-isopropyl-5-[2-(pyridin-4-ylamino)-ethoxy]-benzamide;
3-Chloro-N-[2-(3,3-dimethyl-but-2-yl-carbamoyl)-ethyl]-N-isopropyl-5-[2-(pyridin-4-ylamino)-ethoxy]-benzamide;

3-Chloro-N-[2-(5-hydroxy-[1,2,4]oxadiazol-3-yl)-ethyl]-N-isopropyl-5-[2-(pyridin-4-ylamino)-ethoxy]-benzamide;

N-tert-Butyl-N-(2-tert-butylcarbamoyl-ethyl)-3-chloro-5-[2-(pyridin-4-ylamino)-ethoxy]-benzamide;

N-(2-tert-Butylcarbamoyl-ethyl)-3-chloro-N-cyclobutyl-5-[2-(pyridin-4-ylamino)-ethoxy]-benzamide;

3-Chloro-N-cyclobutyl-N-[2-(2,2-dimethyl-propylcarbamoyl)-ethyl]-5-[2-(pyridin-4-ylamino)-ethoxy]-benzamide;

N-(2-Carbamoyl-ethyl)-3-chloro-N-cyclobutyl-5-[2-(pyridin-4-ylamino)-ethoxy]-benzamide;

3-Chloro-N-isopropyl-5-[2-(pyridin-4-ylamino)-ethoxy]-N-(2-sulfamoyl-ethyl)-benzamide;

3-Chloro-N-2,2-dimethyl-propylsulfamoyl-ethyl)-N-isopropyl-5-[2-(pyridin-4-ylamino)-ethoxy]-benzamide;

6-({3-Chloro-5-[2-(pyridin-4-ylamino)-ethoxy]-benzoyl}-isopropyl-amino)-hexanoic acid;

N-(2-tert-Butylcarbamoyl-ethyl)-N-isopropyl-3-methyl-5-[2-(pyridin-4-ylamino)-ethoxy]-benzamide;

N-(5-tert-Butylcarbamoyl-pentyl)-N-isopropyl-3-methyl-5-[2-(pyridin-4-ylamino)-ethoxy]-benzamide;

3-Chloro-N-[5-(2,2-dimethyl-propylcarbamoyl)-pentyl]-N-isopropyl-5-[2-(pyridin-4-ylamino)-ethoxy]-benzamide;

N-(5-Carbamoyl-pentyl)-N-isopropyl-3-methyl-5-[2-(pyridin-4-ylamino)-ethoxy]-benzamide;

3-Chloro-N-(2-(4-tert-butylphenyl)-ethyl)-N-isopropyl-5-[2-(pyridin-4-ylamino)-ethoxy]-benzamide;

3-Chloro-N-[2-(1,1-dimethyl-propylcarbamoyl)-ethyl]-N-isopropyl-5-[2-(pyridin-4-ylamino)-ethoxy]-benzamide;

3-Chloro-N-isopropyl-N-(3-oxo-3-thiazolidin-3-yl-propyl)-5-[2-(pyridin-4-ylamino)-ethoxy]-benzamide;

N-{2-(2,2-dimethylpropylcarbamoyl)-ethyl}-N-isopropyl-3-methyl-5-[2-(pyridin-4-ylamino)-ethoxy]-benzamide;

3-(Isopropyl-{3-methyl-5-[2-(pyridin-4-ylamino)-ethoxy]-benzoyl}-amino)-propionic acid;

3-(Isopropyl-{3-methyl-5-[2-(pyridin-4-ylamino)-ethoxy]-benzoyl}-amino)-propionic acid methyl ester;

N-(5-tert-Butylcarbamoyl-pentyl)-3-chloro-N-isopropyl-5-[2-(pyridin-4-ylamino)-ethoxy]-benzamide;

6-({3-Methyl-5-[2-(pyridin-4-ylamino)-ethoxy]-benzoyl}-isopropyl-amino)-hexanoic acid;

N-(2-Cyano-ethyl)-N-isopropyl-3-methyl-5-[2-(pyridin-4-ylamino)-ethoxy]-benzamide;

3-Chloro-N,N-diisopropyl-5-[2-(pyridin-4-ylamino)-ethoxy]-benzamide;

3-Chloro-N-isopropyl-5-[2-(pyridin-4-ylamino)-ethoxy]-N-[3-(2,2-dimethyl-propionylamino)-propyl]-benzamide;

3-Chloro-N-isopropyl-5-[2-(pyridin-4-ylamino)-ethoxy]-N-[3-(3,3-dimethyl-butyrylamino)-propyl]-benzamide;

6-({3-Methyl-5-[2-(pyridin-4-ylamino)-ethoxy]-benzoyl}-isopropyl-amino)-hexanoic acid;

and pharmaceutically acceptable derivatives or solvates thereof.

Particularly suitable compounds of the invention include:

3-Chloro-N{2-(5-hydroxy-[1,2,4]oxadiazol-3-yl)-ethyl}-N-isopropyl-5-[2[(pyridin-4-ylamino)-ethoxy]-benzamide;

4-({3-Chloro-5-[2-(pyridin-4-ylamino)-ethoxy]-benzoyl}-cyclobutyl-amino)-butyric acid;

6-({3-Chloro-5-[2-(pyridin-4-ylamino)-ethoxy]-benzoyl}-isobutyl-amino)-hexanoic acid;

4-[({3-Chloro-5-[2-(pyridin-4-ylamino)-ethoxy]-benzoyl}-isobutyl-amino)-methyl]-benzoic acid;

4-[2-({3-Chloro-5-[2-(pyridin-4-ylamino)-ethoxy]-benzoyl}-isobutyl-amino)-ethyl]-benzoic acid;

4-({3-Chloro-5-[2-(pyridin-4-ylamino)-ethoxy]-benzoyl}-cyclopentyl-amino)-butyric acid ethyl ester;

4-({3-Chloro-5-[2-(pyridin-4-ylamino)-ethoxy]-benzoyl}-cyclopentyl-amino)-butyric acid;

3-Chloro-N-cyclopentyl-5-[2-(pyridin-4-ylamino)-ethoxy]-N-[2-(1H-tetrazol-5-yl)-ethyl]-benzamide;

6-({3-Chloro-5-[2-(pyridin-4-ylamino)-ethoxy]-benzoyl}-cyclohexylmethyl-amino)-hexanoic acid;

6-({3-Chloro-5-[2-(pyridin-4-ylamino)-ethoxy]benzoyl}-thiophen-2-ylmethyl-amino)-hexanoic acid;

4-[{3-Chloro-5-[2-(pyridin-4-ylamino)-ethoxy]-benzoyl}-(2-fluoro-phenyl)-amino]-butyric acid methyl ester;

4-[{3-Chloro-5-[2-(pyridin-4-ylamino)-ethoxy]-benzoyl}-(2-fluoro-phenyl)-amino]-butyric acid;

3-Chloro-N-(2-fluoro-phenyl)-5-[2-(pyridin-4-ylamino)-ethoxy]-N-[3-(1H-tetrazol-5-yl)-propyl]-benzamide;

and pharmaceutically acceptable derivatives or solvates thereof.

By "a pharmaceutically acceptable derivative" is meant any pharmaceutically acceptable salt, ester, or salt of such ester, of a compound of formula (I) or any other compound which, upon administration to the recipient, is capable of providing (directly or indirectly) a compound of formula (I) or an active metabolite or residue thereof.

It will be appreciated by those skilled in the art that the compounds of formula (I) may be modified to provide pharmaceutically acceptable derivatives thereof at any of the functional groups in the compounds of formula (I).

It will be appreciated by those skilled in the art that the pharmaceutically acceptable derivatives of the compounds of formula (I) may be derivatised at more than one position.

Preferred pharmaceutically acceptable derivatives of the compounds of formula (I) are pharmaceutically acceptable salts thereof.

Pharmaceutically acceptable salts of the compounds of formula (I) include those derived from pharmaceutically acceptable inorganic and organic acids. Examples of suitable acids include hydrochloric, hydrobromic, sulphuric, nitric, perchloric. fumaric, maleic, phosphoric, glycollic, lactic, salicylic, succinic, toluene-p-sulphonic, di-para-toluoyl tatrate, tartaric, acetic, citric, methanesulphonic, formic, benzoic, malonic, naphthalene-2-sulphonic and benzenesulphonic acids. Other acids such as oxalic, while not in themselves pharmaceutically acceptable may be useful in the preparation of salts useful as intermediates in obtaining compounds of the invention and their pharmaceutically acceptable acid addition salts.

The compounds of formula (I) are thrombin inhibitors and as such are useful in the treatment of clinical conditions susceptible to amelioration by administration of a thrombin inhibitor. Such conditions include: acute vascular diseases such as coronary thrombosis, stroke, pulmonary embolism, deep vein thrombosis, peripheral arterial occlusion, restenosis, and atrial fibrillation; in oedema and PAF mediated inflammatory diseases such as adult respiratory shock syndrome and reperfusion damage; the treatment of disseminated intravascular coagulopathy as a result of e.g. septic shock; the treatment of pulmonary fibrosis; the treatment of tumour metastasis; neurogenerative disease such as Parkinson's and Alzheimer's diseases; viral infection; Kasabach Merritt Syndrome; Haemolytic uremic syndrome; arthritis; and osteoporosis. They may also be useful as anticoagulants for extracorporeal blood in for example, dialysis, blood filtration, bypass, and blood product storage; and in the coating of invasive devices such as prostheses, artificial valves and catheters in reducing the risk of thrombus formation.

The ability of the compounds of formula (I) to inhibit thrombin may be exhibited by methods as described hereinafter.

Accordingly the present invention provides a method of treatment of a mammal, including man, suffering from conditions susceptible to amelioration by a thrombin inhibitor which method comprises administering to the subject an effective amount of a compound of general formula (I) or a pharmaceutically acceptable derivative thereof.

References in this specification to treatment include prophylactic treatment as well as the alleviation of symptoms.

In a further aspect, the present invention provides a compound of formula (I) or a pharmaceutically acceptable derivative thereof for use as a therapeutic agent for use in medicine, particularly human medicine.

In a further aspect, the invention provides the use of a compound of general formula (I) or a pharmaceutically acceptable salt or solvate thereof, for the manufacture of a medicament for the treatment of a condition susceptible to amelioration by a thrombin inhibitor.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable derivative thereof together with one or more pharmaceutically acceptable carriers therefor and, optionally, other therapeutic and/or prophylactic ingredients The compounds of the present invention may be used in combination with other antithrombotic drugs such as thromboxane receptor antagonists, prostacyclin mimetics, phosphodiesterase inhibitors, fibrinogen antagonists, thrombolytic drugs such as tissue plaminogen activator and streptokinase, non-steroidal anti-inflammatory drugs such as aspirin, and the like.

Thus the compounds for use according to the present invention may be formulated for oral, buccal, parenteral, topical, rectal, or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch, sodium starch glycollate or croscarmellose sodium); or wetting agents (e.g. sodium lauryl sulphate). The tablets may be coated by methods well known in the art. The capsules may contain a non-aqueous liquid formulation, for example, a solution or suspension. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds according to the present invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds according to the present invention may be formulated for topical administration by insufflation and inhalation. Examples of types of preparation for topical administration include sprays and aerosols for use in an inhaler or insufflator.

Powders for external application may be formed with the aid of any suitable powder base, for example, lactose, talc, or starch. Spray compositions may be formulated as aqueous solutions or suspensions or as aerosols delivered from pressurised such as metered dose inhalers, with the use of a suitable propellant.

The compounds according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds according to the present invention may be formulated with suitable polymeric or hydrophobic materials (for example as an emulsion in an acceptable oil) or ion exchange resins, or as sparingly soluble derivatives, for example, as a sparingly soluble salt.

For transdermal administration, the pharmaceutical composition may be given in the form of a transdermal patch, such as a transdermal iontophoretic patch.

As stated above, the compounds of the invention may also be used in combination with other therapeutic agents. The invention thus provides, in a further aspect, a combination comprising a compound of formula (I) or a pharmaceutically acceptable derivative thereof together with a further therapeutic agent.

A proposed dose of the compounds according to the present invention for administration to a human (of approximately 70 kg body weight) is 0.01 mg to 10 g, suitably 0.1 mg to 1 g of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and unit of the patient as well as the severity of the condition to be treated. The precise dose and route of administration will ultimately be at the discretion of the attendant physician or veterinarian.

The compounds of the invention may be prepared by any of the processes known in the art for the preparation of similar compounds. For example, according to a first process (A) wherein $R^1$, $R^2$, $R^3$, $R^4$, $R^5$, $R^6$ and $R^7$ are as previously defined, compounds of formula (I) may be prepared by reaction of a compound of formula (II) with a compound of formula (III),

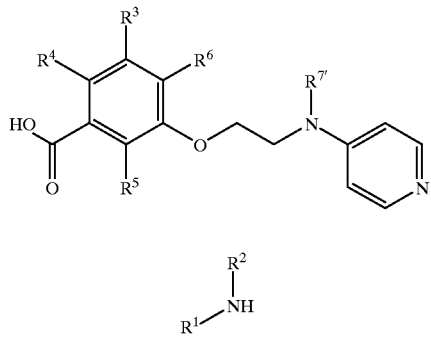

(II)

(III)

where $R^{7'}$ represents $R^7$ or a suitable protecting group such as tert-butoxycarbonyl. The reaction is carried out in the presence of an activating agent or agents such as 1-hydroxybenzotriazole, 2-(1H-benzotriazol-1-yl)-1,1,3,3-tetramethyluronium tetrafluoroborate (TBTU), and a base such as ethyldiisopropylamine in a suitable solvent such as N,N-dimethylformamide, 2-ethoxy-1-ethoxycarbonyl-1,2-dihydroquinolone in a suitable solvent such as acetonitrile, bromo-tris-pyrrolidino-phosphonic hexafluorophosphate in a suitable solvent such as N,N-dimethylformamide, or oxalyl chloride in a suitable solvent such as dichloromethane, followed by deprotection, where appropriate, of any protecting groups present under standard conditions, e.g. acidic conditions for the removal of a tert-butoxycarbonyl group.

Compounds of formula (II) may be prepared by oxidation of the corresponding alcohol of formula (IV)

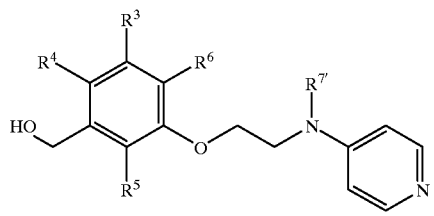

(IV)

where $R^{7'}$ is as defined above. The conversion is effected by treatment of the alcohol with an oxidising agent such as manganese dioxide or dichlorodicyanobenzoquinone in a suitable solvent such as 1,4-dioxan to give the corresponding aldehyde which is then treated with an oxidising agent such as sodium chlorite in the presence of sulfamic acid in a mixture of water and 1,4-dioxan.

Where $R^3$ is $C_{1-3}$ alkyl or $C_{1-2}$ alkoxy and $R^{7'}$ is defined above, compounds of formula (IV) may be prepared by reaction of compounds of formula (V) with compounds of formula (VI),

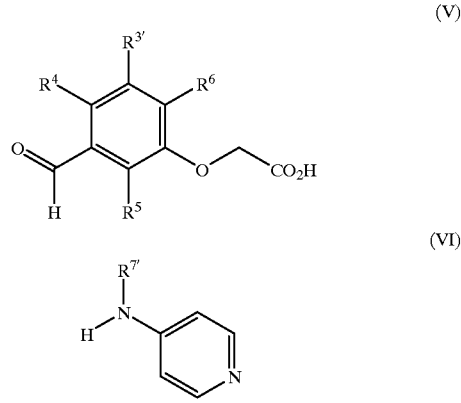

(V)

(VI)

The reaction is suitably carried out in the presence of an activating agent or agents such as TBTU in a suitable solvent such as N,N-dimethylformamide, followed by reduction of the carbonyl groups with a reducing agent such as lithium aluminium hydride in tetrahydrofuran.

Compounds of formula (V) may be prepared from compounds of formula (VII)

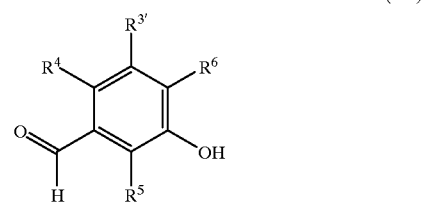

(VII)

using a suitable ester of bromoacetic acid, for example ethyl, in the presence of a suitable base such as potassium carbonate in a suitable solvent such as N,N-dimethylformamide, followed by deprotection of the ester group by conventional methods, for example using a base such as aqueous sodium hydroxide in a suitable solvent such as methanol.

Where $R^3$ represents halogen and $R^{7'}$ is $R^7$, compounds of formula (IV) may be prepared from compounds of formula (VIII)

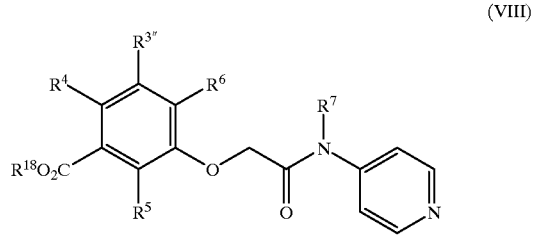

(VIII)

where $R^{3''}$ represents halogen and $R^{18}$ represents a suitable alkyl protecting group, using a suitable reducing agent such as lithium aluminium hydride in a suitable solvent such as tetrahydrofuran.

Compounds of formula (VIII) may be prepared from compounds of formula (IX) and (VI)

(IX)

(VI)

where R³" and R¹⁸ are previously defined. The reaction is carried out in the presence of an activating agent or agents such as 1-hydroxybenzotriazole, TBTU, and a base such as ethyldiisopropylamine in a suitable solvent such as N,N-dimethylformamide.

Compounds of formula (IX) may be prepared from compounds of formula (X)

(X)

where R³" and R¹⁸ are previously defined, using a suitable ester of bromoacetic acid, for example tert-butyl, in the presence of a suitable base such as potassium carbonate or sodium hydride in a suitable solvent such as N,N-dimethylformamide, followed by selective deprotection of the alkanoic ester group by conventional methods, for example cleavage under acidic conditions using trifluoroacetic acid.

Where R³ represents halogen, compounds of formula (II) may also be prepared from compounds of formula (XI)

(XI)

where R⁷' is a suitable protecting group and R¹⁸ is as defined above, by reaction with tert-butyl nitrite and the copper (II) salt of the halide in a suitable solvent such as acetonitrile, followed by deprotection of the the ester group under suitable aqueous base conditions.

Compounds of formula (XI) may be prepared by sequential reaction of ethylene glycol di-p-tosylate with a compound of formula (XII) and a compound of formula (XIII)

(XII)

(XIII)

where R⁷' and R¹⁸ are as defined above, using a suitable base such as sodium hydride in a suitable solvent such as N,N-dimethylformamide.

According to a second process (B), compounds of formula (I) may be prepared by reaction of compounds of formula (XIV) and (XV)

(XIV)

(XV)

where L is a suitable leaving group such as tosylate, in the presence of a suitable base such as sodium hydride in a suitable solvent such as N,N-dimethylformamide.

A compound of formula (XIV) may be prepared by reaction of a compound of formula (XVI) with a compound of formula (III)

(XVI)

where R¹⁹ is a suitable protecting group such as methyl, under conditions suitable for amide coupling as hereinbefore described above, followed by deprotection of R¹⁹ under standard conditions, for example boron tribromide removal of a methyl protecting group.

It will be appreciated that a compound of formula (X) may be reacted with a compound of formula (XV) to give a compound which can be converted to a compound of formula (I) by the methods described above and herein below.

According to a third process (C), compounds of formula (I) may be prepared by reaction of compounds of formula (II) with compounds of formula (III) which are bound to a solid phase resin via a carboxamide or carboxylate functional group on $R^8$ or X, by amide coupling techniques as described herein above, followed by deprotection of any protecting groups and cleavage from the resin under suitable conditions, such as acid treatment with a mixture of trifluoroacetic acid and dichloromethane. Suitable resin materials are described hereinafter with reference to the accompanying examples.

Compounds of formulae (III), (VI), (VII), (X), (XII) (XIII), (XV), and (XVI) are known compounds or may be prepared by standard methods.

It will be appreciated by persons skilled in the art that compounds of formula (I) may be prepared by interconversion, utilising other compounds of formula (I) which are optionally protected by standard protecting groups, as precursors. For instance compounds of formula (I) where $R^1$ or $R^2$ is $R^8$-X and X is substituted by a CN group, may be converted into compounds of formula (I) where X is substituted by e.g. $CONH_2$, $NHSO_2R^{12}$ by methods well known in the art. Further, compounds of formula (I) which contain an $SO_2NHR^{17}$ substituent may be prepared by coupling compounds of formula (II) with a compound of formula (III) containing a sulfonylfluoride group under standard coupling conditions, followed by reaction with a primary amine $R^{17}NH_2$, optionally in the presence of a suitable solvent such as dichloromethane, followed by deprotection of any protecting groups present The compounds of the invention possess thrombin inhibitory activity as determined in vitro by their ability to inhibit human α-thrombin in a chromogenic assay, using N-p-tosyl-gly-pro-lys p-nitroanilide as the chromogenic substrate. All dilutions were made in a buffer consisting of: 50 mM HEPES, 150 mM NaCl, 5 mM $CaCl_2$, 0.1% PEG and at pH 7.4. Briefly, the substrate (final conc. of 100 μM) was added to thrombin (final conc. of 1 nM) and the reaction monitored for 10 mins at 405 nm using a Biotek EL340 plate reader; the assay was performed at room temperature. To obtain $IC_{50}$s the data were analyzed using Kineticalc® with a 4-parameter curve fitting procedure to obtain the $IC_{50}$ value. To determine the $IC_{50}$ at zero and 15 mins. the compounds were preincubated with thrombin for these times prior to adding the chromogenic substrate.

The invention is further illustrated by the following intermediates and examples.

Abbreviations hplc high performance liquid chromatography
Rt Retention time
DIPEA N-Ethyldiisopropylamine
DMF N,N-Dimethylformamide
DMAP 4-Dimethylaminopyridine
TBTU 2-(1H-Benzotriazole-1-yl)-1,1,3,3-tetramethyluronium tetrafluoroborate
HOBt 1-Hydroxybenzotriazole
PyBrop® Bromo-tris-pyrrolidino-phosphonium hexafluorophosphate
HATU® O-(7-azabenzotriazol-1-yl)-1,1,3,3-tetramethyluronium hexafluorophosphate
9-BBN 9-borobicyclo-[3.3.1]-nonane
EEDQ=2-ethoxy-1-ethoxycarbonyl-1,2-dihydroquinoline Methods Analytical hplc was carried out on a Hewlett Packard Series II 1090 Liquid Chromatograph using a Rainin Microsorb C18 column (size 4.6×150 mm, catalog number 80-215-C5) operating at a flow rate of 1.5 ml/min. Eluents were A: 0.1% trifluoroacetic acid/water, B: 0.05% trifluoroacetic acid/acetonitrile.

Gradients:
System 1: 15–95%B in A over 15 min
System 2: 0–75%B in A over 15min
System 3: Supelcosil LCABZ+Plus column (size 4.3 mm×3.3cm; 3-mm particle size) operating at 1 ml/min flow rate. Eluents were A: 0.1% formic acid in 0.01M aqueous ammonium acetate, B: 0.05% formic acid in acetonitrile:water (19:1 v/v) with a gradient of 0–100%B over 3.5min and then running isocratically at 100%B for 3.5 min Retention times are given for the wavelength stated.

Preparative hplc was carried out either on on a Dynamax 60A C18 column (size 41.4 mm×25cm, catalog number 83-241-C) operating at a flow rate of 45 ml/min (eluents were the same as for analytical hplc) or a Supelcosil LC-ABZ column (size 21.2 mm×25 cm) operating at 15 ml/min (eluents were A: 0.1% trifluoroacetic acid/water, B: 0.01% trifluoroacetic acid in 95:5 acetonitrile/water) or Supelcosil LCABZ+Plus column (size 21 mm×10 cm; 5 mm particle size) operating at 4 ml/min flow rate (eluents were A: 0.1% formic acid in water, B: 0.05% formic acid in acetonitrile with a gradient of 0–95%B over 18.65 min.) This system used a Gilson 233XL autosampler/fraction collector.

Flash chromatography was performed on Silica gel 60 (particle size 40–63 μM) Merck catalogue no. 109385

The following amines were synthesized using standard methodology:

N-Propyl-4-aminotetrahydropyran; Mass spectrum: Found: $M^+$ 143;
Cyclopentyl-(3-morpholin-4-yl-propyl)-amine; Mass spectrum: Found: $MH^+$ 213;
Cyclopentyl-(3-pyrrolidin-1-yl-propyl)-amine; Mass spectrum: Found: $MH^+$ 197;
4-Cydopentylamino-butyric acid ethyl ester; Mass spectrum: Found: $MH^+$ 200;
3-Cyclopentylamino-propionamide; Mass spectrum: Found: $MH^+$ 157;
2-Cyclopentylamino-acetamide; Mass spectrum: Found: $MH^+$ 143;
N-Propyl-2,5-difluoroaniline; Mass spectrum: Found: $MH^+$ 172;
3-(2-Fluoro-phenylamino)-propionitrile; Mass spectrum: Found: $MH^+$ 165:
3-(2-Chloro-phenylamino)-propionitrile; Mass spectrum: Found: $MH^+$ 181:
4-(2-Fluoro-phenylamino)-butyric acid methyl ester; Mass spectrum: Found: $MH^+$ 212;
4-(2-Carbamoyl-phenylamino)-butyric acid methyl ester: Mass spectrum: Found: $MH^+$ 237;
4-(2-Fluoro-phenylamino)-butyronitrile; Hplc system 1 (λ=254 nm) Rt.8.0 min;
[2-(2,2-Dimethyl-[1,3]dioxolan-4-ylmethoxy)-ethyl]-phenyl-amine and toluene-4-sulfonic acid 2,2-dimethyl-[1,3]dioxolan-4-ylmethyl ester; Mass spectrum: Found: $MH^+$ 252;
[2-(2,2-Dimethyl-[1,3]dioxolan-4-ylmethoxy)-ethyl]-(2-fluoro-phenyl)-amine; Mass spectrum: Found: $MH^+$ 270;
[2-(2,2-Dimethyl-[1,3]dioxolan-4-ylmethoxy)-ethyl]-(4-fluoro-phenyl)-amine Mass spectrum: Found: $MH^+$ 270;

(R)-1-[3-(2-Fluoro-phenylamino)-propyl]-pyrrolidine-2-carboxylic acid tert-butyl ester; Mass spectrum: Found: MH$^+$ 323;

3-Phenylamino-propionic acid methyl ester; Mass spectrum: Found: MH$^+$ 180;

2-Phenylamino-ethanesulfonyl fluoride; Mass spectrum: Found: MH$^+$ 201;

N-(3-Pyrrolidin-1-yl-propyl)-4-aminotetrahydropyran; Mass spectrum: Found: MH$^+$ 213;

N-(3-Morpholin-4-yl-propyl)-4-aminotetrahydropyran; Mass spectrum: Found: MH$^+$ 229;

N-(2-Propylbutyl)-3-amino-propionamide; Mass spectrum: Found: MH$^+$ 187;

N-Propyl-2-amino-thiazole; Mass spectrum: Found: MH$^+$ 143;

3-Isopropylamino propionic acid methyl ester; Mass spectrum: Found: MH$^+$ 146;

N-Propyl-2-amino-[1,3,4]thiadiazole; Mass spectrum: Found: MH$^+$ 144;

2-(2-Isopropylamino-ethyl)-N-[1,2,4]-triazole; Mass spectrum: Found: MH$^+$ 154;

3-(2-Isopropylamino-ethyl)-5-hydroxy-[1,2,4]oxadiaxole trifluoroacetate; Mass spectrum: Found: MH$^+$ 172;

4-Fluorophenyl-(3-[1,2,4]triazol-1-yl-propyl)-amine; Mass spectrum: Found: MH$^+$ 221;

4-Fluorophenyl-(3-tetrazol-2-yl-propyl)-amine; Mass spectrum: Found: MH$^+$ 222;

Cyclopentyl-(2-[1,2,4]triazol-1-yl-ethyl)-amine; Mass spectrum: Found: MH$^+$ 181;

Cyclopentyl-(4-[1,2,4]triazol-1-yl-butyl)-amine; Mass spectrum: Found: MH$^+$ 209;

3-Fluorophenyl-(3-tetrazol-2-yl-propyl)-amine; Mass spectrum: Found: MH$^+$ 222;

2-Fluorophenyl-(3-tetrazol-2-yl-propyl)-amine; Mass spectrum: Found: MH$^+$ 222;

Phenyl-(3-tetrazol-2-yl-propyl)-amine; Mass spectrum: Found: MH$^+$ 190;

Phenyl-(3-[1,2,3]-triazol-2-yl-propyl)-amine; Mass spectrum: Found: MH$^+$ 189;

Phenyl-2-(pyridin-2-yloxy)-ethylamine; Mass spectrum: Found: MH$^+$ 215;

Isopropyl-2-methoxy-ethylamine; Mass spectrum: Found: MH$^+$ 118;

N-(3-Cyclopentylamino-propyl)-C,C,C-trifluoro-methanesulfonamide formate; Mass spectrum: Found: MH$^+$ 275;

5-(2-Isopropylamino-ethyl)-[1,2,4]oxadiazol-3-ylamine; Mass spectrum: Found: MH$^+$ 171;

3-(tert-Butylamino)-propionic acid methyl ester; Mass spectrum: Found: MH$^+$ 160;

3-Cyclobutylamino-propionic acid methyl ester, Mass spectrum: Found: MH$^+$ 158;

3-(Cyclobutylamino)propionitrile, Mass spectrum: Found: MH$^+$ 125;

2-Isopropylamino-ethanesulfonic acid amide, Mass spectrum: Found: MH$^+$ 167;

2-Isopropylaminoethanesulfonic acid (2,2-dimethyl-propyl)-amide, Mass spectrum: Found: MH$^+$ 237;

3-(2-Isopropylaminoethyl)-5-hydroxy-[1,2,4]oxadiaxole trifluoroacetate, Mass spectrum: Found: MH$^+$ 172;

Isopropyl-2-(4-tert-butylphenyl)-ethylamine, Mass spectrum: Found: MH$^+$ 220; and Isopropyl-2-(pyridin-2-yloxy)-ethylamine, Mass spectrum: Found: MH$^+$ 181.

INTERMEDIATE 1

2-(3-Formyl-5-methyl-phenoxy)-acetic acid ethyl ester

To a stirred suspension of anhydrous potassium carbonate (1.52 g) in dry DMF (20 ml) was added 3-hydroxy-5-methylbenzaldehyde[1] (0.5 g). The mixture was stirred under an atmosphere of nitrogen for 1.5 h and then ethyl bromoacetate (0.45 ml) was added. The mixture was stirred for a further 18 h and then evaporated to dryness under reduced pressure. The residue was partitioned between ethyl acetate and saturated sodium bicarbonate solution and the combined organic phase was washed with water, saturated lithium chloride solution, and saturated sodium chloride solution. The solution was dried over magnesium sulphate and concentrated to give the title compound as an amber-coloured gum (0.79 g). Hplc system 1 ($\lambda$=254 nm) Rt 8.0 min.

INTERMEDIATE 2

2-(3-Formyl-5-methyl-phenoxy)-acetic acid

A stirred solution of 2-(3-formyl-5-methyl-phenoxy)-acetic acid ethyl ester (0.79 g) in methanol (4 ml) at 5° C. was treated with a 2M sodium hydroxide solution (3.6 ml). After 15 min the mixture was allowed to warm to room temperature. After a further 2 h the stirred solution was again cooled to 5° C. and covered with ethyl acetate and the aqueous layer was adjusted to acidic pH with 2M hydrochloric acid. The layers were separated and the aqueous phase was extracted with more ethyl acetate. The combined organic phase was washed with water and brine and dried with magnesium sulphate. Concentration gave a gummy solid which was triturated with diethyl ether giving, after drying, the title compound (0.47 g) as a pale yellow solid. Hplc system 1 ($\lambda$=254 nm) Rt 5.2 min.

INTERMEDIATE 3

2-(3-Formyl-5-methyl-phenoxy)-N-pyridin-4-yl-acetamide 2-(3-Formyl-5-methyl-phenoxy)-acetic acid (0.47 g) and 4-aminopyridine (0.46 g) were dissolved in dry DMF (10 ml). The resulting solution, stirring under a nitrogen atmosphere, was treated with TBTU (0.82 g). The resulting mixture was stirred for 68 h and then concentrated at reduced pressure to give a yellow viscous gum. This crude material was purified by preparative hplc. The purified product was partitioned between ethyl acetate and an aqueous solution saturated with sodium bicarbonate, sodium chloride and ammonium sulphate. The organic phase was dried over magnesium sulphate and concentrated under reduced pressure giving the title compound as an off-white solid (0.40 g).

Mass spectrum: Found: MH$^+$ 271.

INTERMEDIATE 4

{3-Methyl-5-[2-(pyridin-4-ylamino)-ethoxy]-phenyl}-methanol

A suspension of 2-(3-formyl-5-methyl-phenoxy)-N-pyridin-4-yl-acetamide (0.30 g) in anhydrous tetahydrofuran (1 ml), stirring under a nitrogen atmosphere, was cooled to about 1° C. and treated with a 1M tetrahydrofuran solution of lithium aluminium hydnde (5.47 ml) over a period of 3 min. After 15 min the mixture was allowed to warm to room temperature. After stirring for a further 22 h the mixture was cooled to about 2° C. and the excess reagent was quenched with cautious dropwise addition of wet tetrahydrofuran and then water. The resulting aqueous mixture was partitioned between ethyl acetate and dilute sodium hydroxide solution saturated with sodium chloride and ammonium sulphate. The organic phase was dried with magnesium sulphate and concentrated under reduced pressure and the resulting gum was triturated with diethyl ether giving, after drying, the title compound as an off-white solid (0.13 g).

Hplc system 2 ($\lambda$=254 nm) Rt 7.6 min.

INTERMEDIATE 5

3-Methyl-5-[2-(pyridin-4-ylamino)-ethoxy]-benzaldehyde

A suspension of {3-methyl-5-[2-(pyridin-4-ylamino)-ethoxy]-phenyl}-methanol (0.132 g) and manganese dioxide (0.370 g) in 1,4-dioxan (5 ml) was heated to reflux with stirring under an atmosphere of dry nitrogen for 5 h. After cooling to room temperature the mixture was filtered through Harborlite® and the pad washed with 1,4-dioxan and then methanol. The combined filtrates were evaporated to dryness under reduced pressure to give an off-white solid. Trituration with diethyl ether gave, after drying, the title compound as a white powder (0.074 g).

Hplc system 2 ($\lambda$=254 nm) Rt 8.9 min.

INTERMEDIATE 6

3-Methyl-5-[2-(pyridin-4-ylamino)-ethoxy]-benzoic acid trifluoroacetate salt A stirred solution of 3-methyl-5-[2-(pyridin-4-ylamino)-ethoxy]-benzaldehyde (0.074 g) in a 3:2 v/v mixture of 1,4-dioxan and water (7 ml) was treated with sulphamic acid (0.163 g) and then sodium chlorite (0.208 g). After 22 h the mixture was cooled to 0° C. and treated with an aqueous solution of sodium bisulphite until the mixture was colourless. The pH was adjusted to about 7 by the addition of saturated sodium bicarbonate solution and the mixture concentrated to about 5 ml under reduced pressure and subjected to preparative hplc. The required fraction was concentrated and dried by addition of toluene followed by concentration at reduced pressure. This yielded the title compound as a white powder (0.061 g).

Hplc system 2 ($\lambda$=254 nm) Rt 8.3 min.

INTERMEDIATE 7

3-Bromo-5-hdroxybenzoic acid methyl ester

A solution of sodium nitrite (5.9 g) in water (17 ml) was added to a stirred solution of 3-amino-5-hydroxybenzoic acid methyl ester (12.2 g) in a mixture of methanol (33 ml) and concentrated sulphuric acid (66 ml) at 0° C. over 90 min. The reaction mixture was stored at 0° C. and added over 2 h to a stirred mixture of copper (I) bromide (32.3 g) in 8% w/v aqueous hydrobromic acid (120 ml) at 65° C. After the addition was complete the reaction mixture was cooled to 0° C. and then filtered. The residue was washed with water, 1M hydrochloric acid and further water. The solid was extracted with diethyl ether and the residual solids removed by filtration. The filtrate was dried with anhydrous sodium sulphate and then concentrated under reduced pressure. This yielded the title compound as a red solid (10.5 g).

Hplc system 1 ($\mu$=254 nm) Rt 7.5 min.

INTERMEDIATE 8

2-(5-Bromo-3-methoxycarbonyl-phenoxy)-acetic acid tert-butyl ester

To a stirred solution of 3-bromo-5-hydroxybenzoic acid methyl ester (10.2 g) and tert-butyl bromoacetate (9.7 ml) in anhydrous DMF was added sodium hydride (60% dispersion in mineral oil, 2.69). After 30 min water (10 ml) aws added. The reaction mixture was partitioned between ethyl acetate and water. The aqueous phase was removed and the organic phase washed with further water, 1M sodium hydroxide solution and dried with brine and over sodium sulphate. Concentration under reduced pressure gave the title compound as dark yellow gum (12.8 g).

Hplc system 1 ($\lambda$=254 nm) Rt 11.4 min.

INTERMEDIATE 9

2-(5-Bromo-3-ethoxycarbonyl-phenoxy)-acetic acid

A solution of 2-(5-bromo-3-methoxycarbonyl-phenoxy)-acetic acid tert-butyl ester (12.8 g) in a mixture of dichloromethane (100 ml) and trifluoroacetic acid (100 ml) was stored at room temperature for 2 h. The solution was concentrated under reduced pressure. The residual solid was suspended in toluene and the solvent removed under reduced pressure to give the title compound as a brown solid (10.6 g).

Hplc system 1 ($\lambda$=254 nm) Rt 7.3 min.

INTERMEDIATE 10

2-(5Bromo-3-methoxycarbonyl-phenoxy)-N-Pyridin-4-yl-acetamide

A solution of 2-(5-bromo-3-methoxycarbonyl-phenoxy)-acetic acid (10.6 g), TBTU (19.3 g) and HOBt (5.1 g) in dry DMF (50 ml) was treated with DIPEA (9.9 ml). The resulting solution was stirred under a nitrogen atmosphere and was then treated with 4-aminopyridine (3.6 g) after 30 min. The resulting mixture was stirred for 18 h and then concentrated at reduced pressure to give a yellow viscous gum which was partitioned between ethyl acetate and water. The aqueous layer was removed and the organic phase washed with further water, 1M sodium hydroxide solution, aqueous saturated ammonium chloride, water and dried with brine and over sodium sulphate. The organic phase was concentrated under reduced pressure giving the title compound as a yellow solid (6.60 g).

Hplc system 1 ($\lambda$=254 nm) Rt 6.7 min.

INTERMEDIATE 11

{3-Bromo-5-[2-(pyridin-4-ylamino)-ethoxy]-phenyl}-methanol

A stiired solution of 2-(5-bromo-3-methoxycarbonyl-phenoxy)-N-pyridin-4-yl-acetamide (6.61 g) in anhydrous tetrahydrofuran (200 ml) was treated with a 1M diethyl ether solution of lithium aluminium hydride (56.1 ml) over a period of 20 min. A brown precipitate appeared and the mixture was stirred at room temperature for 6 h. The reaction mixture was treated with water (2 ml) 1M sodium hydroxide solution (2 ml), water (6 ml) and then with 2M hydrochloric acid (150 ml). The reaction mixture was extracted with ethyl acetate and then basified with 2M sodium hydroxide solution. The reaction mixture was reextracted with ethyl acetate. The first organic phase was washed with saturated aqueous sodium bicarbonate and combined with the second organic phase. The combined organic phase was washed with water and dried with brine and over sodium sulphate. Concentration of the organic phase gave a gum which was found to be unsatisfactory so the gum was partitioned between ethyl acetate and 2M hydrochloric acid. The aqueous layer was separated, basified to pH 10 and extracted with ethyl acetate. The organic phase was washed with water and dried with brine and over sodium sulphate. Concentration under reduced pressure gave the title compound as an off-white solid (1.5 g).

Hplc system 1 ($\lambda$=254 nm) Rt 5.4 min.

INTERMEDIATE 12

3-Bromo-5-[2-(pyridin-4-ylamino)-ethoxy]-benzaldehyde

A suspension of {3-bromo-5-[2-(pyridin-4-ylamino)-ethoxy]-phenyl}-methanol (1.4 g) and manganese dioxide (3.2 g) in 1,4-dioxan (50 ml) was heated to reflux with stirring under an atmosphere of dry nitrogen for 8 h. After cooling to room temperature the mixture was stirred at room temperature for 16 h, and then filtered through Harborlite® and the pad washed with hot methanol. The combined filtrates were evaporated to dryness under reduced pressure to give the title compound as an off-white solid (1.2 g).

Hplc system 1 ($\lambda$=254 nm) Rt 9.8 min.

INTERMEDIATE 13

3-Bromo-5-[2-(pyridin-4-ylamino)-ethoxy]-benzoic acid trifluoroacetate salt

A stirred solution of 3-bromo-5-[2-(pyridin-4-ylamino)-ethoxy]-benzaldehyde (1.2 g) in 1,4-dioxan and water (3:2 v/v, 50 ml) was treated with sulphamic acid (2.5 g) and then sodium chlorite (3.2 g). After 3 h the mixture was treated with an aqueous solution of sodium bisulphite until the mixture was colourless. The mixture was concentrated under reduced pressure and extracted with several portions of hot ethanol. The combined ethanolic solution was concentrated under reduced pressure and purified by preparative hplc. The required fraction was concentrated and dried by addition of acetonitrile followed by concentration at reduced pressure. This yielded the title compound as a white solid (0.495 g).

Hplc system 1 ($\lambda$=254 nm) Rt 9.0 min.

INTERMEDIATE 14

3-Amino-5-[2-(tert-butoxycarbonyl-pyridin-4-yl-amino)-ethoxy]-benzoic acid methyl ester To a stirred solution of pyridin-4-yl-carbamic acid tert-butyl ester[2] (3.9 g) and ethylene glycol di-p-tosylate (7.4 g) in DMF at room temperature under a nitrogen atmosphere was added sodium hydride (60% dispersion in mineral oil, 0.88 g). Stirring was continued for 7 h and then 3-amino-5-hydroxybenzoic acid, methyl ester[3] (2.5 g) and sodium hydride (60% dispersion in mineral oil, 0.66 g) were added. The reaction mixture was stirred for 66 hr and then water (10 ml) added. The mixture was concentrated under reduced pressure and the residue partitioned between 2M hydrochloric acid and ethyl acetate. The aqueous phase was separated and the organic phase reextracted with 2M hydrochloric acid. The aqueous layers were combined and neutralised with sodium hydroxide pellets and then extracted with ethyl acetate. The organic phase was washed with water and then dried with brine and over sodium sulphate. Concentration under reduced pressure gave the title compound as a dark brown gum (4.2 g).

Mass spectrum: Found: MH$^+$ 388.

INTERMEDIATE 15

3-[2(tert-Butoxycarbonyl-pyridin-4-yl-amino)-ethoxy]-5-chloro-benzoic acid methyl ester To a stirred suspension of anhydrous copper(II)chloride (0.67 g) in acetonitrile (20 ml) at room temperature was added tert-butyl nitrite (0.7 ml). The reaction mixture was heated to reflux and a solution of 3-amino-5-[2-(tert-butoxycarbonyl-pyridin-4-yl-amino)-ethoxy]-benzoic acid methyl ester (1.94 g) in acetonitrile (5 ml) added. The reaction was stirred at reflux for 10 min, cooled to room temperature and then concentrated under reduced pressure. The residue was partitioned between ethyl acetate and 2M hydrochloric acid. The organic phase was washed with water and dried with brine and over sodium sulphate and concentrated under reduced pressure. The residue was purified by flash column chromatography eluting with dichloromethane:methanol (50:1 v/v) to give the title compound as a red gum (0.58 g).

Hplc system 1 ($\lambda$=254 nm) Rt 12.6 min.

INTERMEDIATE 16

3-[2-(tert-Butoxycarbonyl-pyridin-4-yl-amino)-ethoxy]-5-chloro-benzoic acid

To a stirred solution of 3-[2-(tert-butoxycarbonyl-pyridin-4-yl-amino)-ethoxy]-5-chloro-benzoic acid methyl ester (0.58 g) in a mixture of 1,4-dioxane (5 ml) and water (5 ml) was added 2M sodium hydroxide solution (0.72 ml). The reaction mixture was stirred at room temperature for 20 h, acidified by the addition of 2M hydrochloric acid (0.75 ml) and then concentrated under reduced pressure. The residue was partitioned between ethyl acetate and water, the aqueous layer removed and the organic phase washed with further water and dried with brine and over sodium sulphate. Concentration of the organic phase under reduced pressure gave the title compound as a yellow solid (0.32 g).

Hplc system 1 ($\lambda$=254 nm) Rt 7.7 min.

INTERMEDIATE 17

{2-[3-Chloro-5-(cyclohexyl-methyl-carbamoyl)-phenoxy]-ethyl}pyridin-4-yl-carbamic acid tert-butyl ester To a stirred solution of 3-[2-(tert-butoxycarbonyl-pyridin-4-yl-amino)-ethoxy]-5-chloro-benzoic acid (0.039 g), TBTU (0.064 g) and HOBt (0.027 g) in DMF (1 ml) was added DIPEA (0.036 ml) followed by N-methylcyclohexylamine (0.027 ml) after 15 min. The reaction mixture was stirred at room temperature for 18 h and then concentrated under reduced pressure. The residue was subjected to preparative hplc and the title compound (0.036 g) was obtained as a colourless gum by concentration of the required fraction under reduced pressure and drying by repetitive addition of acetonitrile and concentration under reduced pressure.

Hplc system 1 ($\lambda$=254 nm) Rt 10.7 min.

INTERMEDIATE 18

{2-[3-(Allyl-cyclopentyl-carbamoyl)-5-chloro-phenoxy]-ethyl}-pyridin-4-yl-carbamic acid tert-butyl ester To a strrred solution of 3-[2-(tert-butoxycarbonyl-pyridin-4-yl-amino)-ethoxy]-5-chloro-benzoic acid (0.039 g), TBTU (0.064 g) and HOBt (0.027 g) in DMF (1 ml) was added DIPEA (0.036 ml) followed by N-allylcyclopentylamine (0.029 ml) after 15 min. The reaction mixture was stirred at room temperature for 18 h and then concentrated under reduced pressure. The residue was subjected to preparative hplc and the title compound (0.030 g) obtained by concentration of the required fraction under reduced pressure and drying by repetitive addition of acetonitrile and concentration under reduced pressure.

Hplc system 1 ($\lambda$=254 nm) Rt 11.0 min.

INTERMEDIATE 19

{2-[3-(Allyl-cyclohexyl-carbamoyl)-5-chloro-phenoxy]-ethyl}-pyridin-4-yl-carbamic acid tertbutyl ester To a stirred solution of 3-[2-(tert-butoxycarbonyl-pyridin-4-yl-amino)-ethoxy]-5-chloro-benzoic acid (0.039 g), TBTU (0.064 g) and HOBt (0.027 g) in DMF (1 ml) was added DIPEA (0.036 ml) followed by N-allylcyclohexylamine (0.029 ml) after 15 min. The reaction mixture was stirred at room temperature for 18 h and then concentrated under reduced pressure. The residue was subjected to preparative hplc and the title compound (0.032 g) was obtained as a colourless gum by concentration of the required fraction under reduced pressure and drying by repetitive addition of acetonitrile and concentration under reduced pressure.

Hplc system 1 ($\lambda$=254 nm) Rt 11.5 min.

INTERMEDIATE 20

{2-[3-(Propyl-cyclopentyl-carbamoyl)-5-chloro-phenoxy]-ethyl}-pyridin-4-yl-carbamic acid tert-butyl ester A suspension of 5% Pd on carbon (0.01 g) in a solution of {2-[3-(allyl-cyclopentyl-carbamoyl)-5-chloro-phenoxy]-ethyl}-pyridin-4-yl-carbamic-acid tert-butyl ester (0.07 g) in toluene (10 ml) was stirred under an atmosphere of hydrogen for 2 h. The catalyst was filtered through diatomaceous earth and the filtrate evaporated to give the title compound as a pale yellow gum (0.07 g).

Mass spectrum: Found: MH$^+$ 502 ($^{35}$Cl).

INTERMEDIATE 21

(2-{3-Chloro-5-[cyclopentyl-(3-hydroxy-propyl)-carbamoyl]-phenoxy}-ethyl)-pyridin-4-yl-carbamic acid tert-butyl ester To {2-[3-(allyl-cyclopentyl-carbamoyl)-5-chloro-phenoxy]-ethyl}-pyridin-4-yl-carbamic acid tert-butyl ester (0.11 g) was added 9-BBN (0.5M in THF, 2.2 ml) and the resulting solution stirred at room temperature under nitrogen for 20 h. A mixture of 28% aqueous hydrogen peroxide solution (1.8 ml) and 2M aqueous sodium hydroxide (0.9 ml) was added and the reaction mixture stirred at reflux for 2 h. The solvent was removed in vacuo and the residue purified by preparative hplc and the title compound (0.064 g) was obtained as a colourless gum by concentration of the required fraction under reduced pressure and drying by repetitive addition of acetonitrile and concentration under reduced pressure.

Mass spectrum: Found: MH$^+$ 518 ($^{35}$Cl).

INTERMEDIATE 22

(2-{3-Chloro-5-[propyl-(tetrahydro-pyran-4-yl)-carbamoyl]-phenoxy}-ethyl)-pyridin-4-yl-carbamic acid tert-butyl ester To a stirred solution of 3-[2-(tert-butoxycarbonyl-pyridin-4-yl-amino)-ethoxy]-5-chloro-benzoic acid (0.06 g), TBTU (0.096 g) and HOBt (0.030 g) in DMF (1 ml) was added DIPEA (0.052 ml) followed by N-propyl-aminotetrahydropyran (0.033 g) as a solution in DMF (1 ml) after 20 min. The reaction mixture was stirred at room temperature for 20 h and then concentrated under reduced pressure. The residue was partitioned between ethyl acetate and water. The organic phase was washed with further water and saturated aqueous sodium bicarbonate and dried with brine and over sodium sulphate and concentrated under reduced pressure to give the title compound as a gum (0.07 g).

Mass spectrum: Found: MH$^+$ 518 ($^{35}$Cl).

INTERMEDIATE 23

(2-{3-Chloro-5-[cyclopentyl-(2,3-dihydroxy-propyl)-carbamoyl]-phenoxy}-ethyl)-pyridin-4-yl-carbamic acid tert-butyl ester To a solution of {2-[3-(allyl-cyclopentyl-carbamoyl)-5-chloro-phenoxy]-ethyl}-pyridin-4-yl-carbamic acid tert-butyl ester (0.075 g) in a mixture of acetone (1.0 ml) and water (0.5 ml) was added osmium tetroxide (1.52 ml of a 2.5% solution in tert-butanol. After 16 h excess sodium sulphite was added to the reaction mixture and the mixture partitioned between chloroform and water. The organic layer was concentrated to give the title compound (0.044 g) which was used without further purification.

INTERMEDIATE 24

(2-{3-Chloro-5-[cyclopentyl-(3-morpholin-4-yl-propyl)-carbamoyl]-phenoxy}-ethyl)-pyridin-4-yl-carbamic acid tert-butyl ester trifluoroacetate To a stirred solution of 3-[2-(tert-butoxycarbonyl-pyridin-4-yl-amino)-ethoxy]-5-chloro-benzoic acid (0.060 g), TBTU (0.096 g) and HOBt (0.030 g) in DMF (1 ml) was added DIPEA (0.052 ml) followed by cyclopentyl-(3-morpholin-4-yl-propyl)-amine (0.064 g) after 5 min. The reaction mixture was stirred at room temperature for 18 h and then concentrated under reduced pressure. The residue was subjected to preparative hplc and the title compound (0.060 g) was obtained as a colourless gum by concentration of the required fraction under reduced pressure and drying by repetitive addition of acetonitrile and concentration under reduced pressure.

Hplc system 1 ($\lambda$=254 nm) Rt 6.5 min.

INTERMEDIATE 25

(2-{3-Chloro-5-[cyclopentyl-(3-pyrrolidin-1-yl-propyl)-carbamoyl]-phenoxy}-ethyl)-pyridin-4-yl-carbamic acid tert-butyl ester trifluoroacetate To a stirred solution of 3-[2-(tert-butoxycarbonyl-pyridin-4-yl-amino)-ethoxy]-5-chloro-benzoic acid (0.060 g), TBTU (0.096 g) and HOBt (0.030 g) in DMF (1 ml) was added DIPEA (0.052 ml) followed by cyclopentyl-(3-pyrrolidin-1-yl-propyl)-amine (0.059 g) after 15 min. The reaction mixture was stirred at room temperature for 18 h and then concentrated under reduced pressure. The residue was subjected to preparative hplc and the title compound (0.080 g) was obtained as a colourless gum by concentration of the required fraction under reduced pressure and drying by repetitive addition of acetonitrile and concentration under reduced pressure.

Mass spectrum: Found: MH$^+$ 571 ($^{35}$Cl).

INTERMEDIATE 26

4-({3-[2-(tert-Butoxycarbonyl-pyridin-4-yl-amino)-ethoxy]-5-chloro-benzoyl}-cyclopentyl-amino)-butyric acid ethyl ester To a stirred solution of 3-[2-(tert-butoxycarbonyl-pyridin-4-yl-amino)-ethoxy]-5-chloro-benzoic acid (0.300 g), TBTU (0.482 g) and HOBt (0.150 g) in DMF (5 ml) was added DIPEA (0.260 ml) followed by 4-cyclopentylamino-butyric acid ethyl ester (0.316 g) after 10 min. The reaction mixture was stirred at room temperature for 16 h and then further 4-cyclopentylamino-butyric acid ethyl ester (0.316 g) was added. After 24 h, the reaction mixture was concentrated under reduced pressure to give a viscous gum which was partitioned between ethyl acetate and water. The aqueous layer was removed and the organic phase washed with further water, aqueous saturated sodium bicarbonate solution, water and dried with brine and over sodium sulphate. The organic phase was concentrated under reduced pressure to give crude product as a black gum (0.420 g) which was purified by preparative hplc and the title compound (0.189 g) was obtained as a colourless gum by concentration of the required fraction under reduced pressure and drying by repetitive addition of acetonitrile and concentration under reduced pressure.

Hplc system 1 ($\lambda$=254 nm) Rt 10.9 min.

INTERMEDIATE 27

4-({3-[2-(tert-Butoxycarbonyl-pyridin-4-yl-amino)-ethoxy]-5-chloro-benzoyl}-cyclopentyl-amino)-butyric acid 2M Aqueous sodium hydroxide (0.33 ml) was added to a stirred solution of 4-({3-[2-(tert-butoxycarbonyl-pyridin-4-yl-amino)-ethoxy]-5-chloro-benzoyl}-cyclopentyl-amino)-butyric acid ethyl ester (0.189 g) in 1,4-dioxan (2 ml). 2M aqueous hydrochloric acid (0.33 ml) was added after 1 h. The reaction mixture was partitioned between ethyl acetate and water. The aqueous layer was removed and the organic phase was dried with brine and over sodium sulphate and then concentrated under reduced pressure to give the title compound (0.138 g) as a white foam.

Mass spectrum: Found: MH$^+$ 546 ($^{35}$Cl).

INTERMEDIATE 28

(2-{3-[(3-Carbamoyl-propyl)-cyclopentyl-carbamoyl]-5-chloro-phenoxy}ethyl)-pyridin-4-yl-carbamic acid tert-butyl ester To a stirred solution of 4-({3-[2-(tert-butoxycarbonyl-pyridin-4-yl-amino)-ethoxy]-5-chloro-benzoyl}-cyclopentyl-amino)-butyric acid (0.049 g), TBTU (0.058 g) and HOBt (0.024 g) in DMF (1 ml) was added DIPEA (0.031 ml) followed a 0.5M solution of ammonia in 1,4-dioxane (0.36 ml) after 15 min. The reaction mixture was stirred at room temperature for 43 h and then concentrated under reduced pressure. The residue was subjected to preparative hplc and the title compound (0.040 g) was obtained as a colourless gum by concentration of the required fraction under reduced pressure and drying by repetitive addition of acetonitrile and concentration under reduced pressure.

Mass spectrum: Found: MH$^+$ 545 ($^{35}$Cl).

INTERMEDIATE 29

(2-{3-Chloro-N-cyclopentyl-N-(4-oxo-4-pyrrolidin-1-yl-butyl)-carbamoyl]-phenoxy}-ethyl)-pyridin-4-yl-carbamic acid tert-butyl ester To a stirred solution of 4-({3-[2-(tert-butoxycarbonyl-pyridin-4-yl-amino)-ethoxy]-5-chloro-benzoyl}-cyclopentyl-amino)-butyric acid (0.028 g), TBTU (0.034 g) and HOBt (0.008 g) in DMF (0.2 ml) was added DIPEA (0.024 ml) followed by pyrrolidine (0.008 ml) after 15 min. The reaction mixture was stirred at room temperature for 43 h and then concentrated under reduced pressure. The residue was subjected to preparative hplc and the title compound (0.025 g) was obtained as a colourless gum by concentration of the required fraction under reduced pressure and drying by repetitive addition of acetonitrile and concentration under reduced pressure.

Mass spectrum: Found: MH$^+$ 599 ($^{35}$Cl).

INTERMEDIATE 30

(2-{3-[(2-Carbamoyl-ethyl)-cyclopentyl-carbamoyl]-5-chloro-phenoxy}-ethyl)-pyridin-4-yl-carbamic acid tert-butyl ester To a stirred solution of 3-[2-(tert-butoxycarbonyl-pyridin-4-yl-amino)-ethoxy]-5-chloro-benzoic acid (0.060 g), TBTU (0.096 g) and HOBt (0.030 g) in DMF (1 ml) was added DIPEA (0.052 ml) followed by 3-cyclopentylamino-propionamide (0.047 mg) after 10 min. The reaction mixture was stirred at room temperature for 18 h and then concentrated under reduced pressure. The residue was subjected to preparative hplc and the title compound (0.074 g) was obtained as a colourless gum by concentration of the required fraction under reduced pressure and drying by repetitive addition of acetonitrile and concentration under reduced pressure.

Mass spectrum: Found: MH$^+$ 531 ($^{35}$Cl).

INTERMEDIATE 31

{2-[3-Chloro-5-(ethyl-phenyl-carbamoyl)-cyclopentyl-phenoxy]-ethyl}-pyridin-4-yl-carbamic acid tert-butyl ester To a stirred solution of 3-[2-(tert-butoxy carbonyl-pyridin-4-yl-amino)-ethoxy-]-5-chloro-benzoic acid (0.060 g), TBTU (0.096 g) and HOBt (0.030 g) in DMF (1 ml) was added DIPEA (0.052 ml) followed by 2-cyclopentylamino-acetamide (0.043 g) after 10 min. The reaction mixture was stirred at room temperature for 18 h and then concentrated under reduced pressure. The residue was subjected to preparative hplc and the title compound (0.064 g) was obtained as a colourless gum by concentration of the required fraction under reduced pressure and drying by repetitive addition of acetonitrile and concentration under reduced pressure.

Mass spectrum: Found: MH$^+$ 531 ($^{35}$Cl).

INTERMEDIATE 32

(2-{3-[(2-Carbamoyl-methyl)-cyclopentyl-carbamoyl]-5-chloro-phenoxy}-ethyl)-pyridin-4-yl-carbamic acid tert-butyl ester To a stirred solution of 3-[2-(tert-butoxycarbonyl-pyridin-4-yl-amino)-ethoxy]-5-chloro-benzoic acid (0.060 g), TBTU (0.096 g) and HOBt (0.030 g) in DMF (1 ml) was added DIPEA (0.052 ml) followed by 3-cyclopentylamino-acetamide (0.043 g) after 15 min. The reaction mixture was stirred at room temperature for 18 h and then concentrated under reduced pressure. The residue was subjected to preparative hplc and the title compound (0.057 g) was obtained as a colourless gum by concentration of the required fraction under reduced pressure and drying by repetitive addition of acetonitrile and concentration under reduced pressure.

Mass spectrum: Found: MH$^+$ 517 ($^{35}$Cl).

INTERMEDIATE 33

(2-{3-Chloro-5-[(2-cyano-ethyl)-cyclopropyl-carbamoyl]-phenoxy}-ethyl)-pyridin-4-yl-carbamic acid tert-butyl ester To a stirred solution of 3-[2-tert-butoxycarbonyl-pyridin-4-yl-amino)-ethoxy]-5-chloro-benzoic acid (0.060 g), TBTU (0.096 g) and HOBt (0.030 g) in DMF (1 ml) was added DIPEA (0.052 ml) followed by 3-cyclopropylpropionitrile (0.050 g) after 15 min. The reaction mixture was stirred at room temperature for 18 h and then concentrated under reduced pressure. The residue was subjected to preparative hplc and the title compound (0.075 g) was obtained as a colourless gum by concentration of the required fraction under reduced pressure and drying by repetitive addition of acetonitrile and concentration under reduced pressure.

Hplc system 1 ($\lambda$=254 nm) Rt 8.1 min.

INTERMEDIATE 34

[2-(3-Chloro-5-dipropylcarbamoyl-phenoxy)-ethyl]-pyridin-4-yl-carbamic acid tert-butyl ester To a stirred solution of 3-[2-tert-butoxycarbonyl-pyridin-4-yl-amino)-ethoxy]-5-chloro-benzoic acid (0.060 g), TBTU (0.096 g) and HOBt (0.030 g) in DMF (1 ml) was added DIPEA (0.052 ml) followed by dipropylamine (0.030 mg) after 20 min. The reaction mixture was stirred at room temperature for 18 h and then concentrated under reduced pressure. The residue was subjected to preparative hplc and the title compound (0.085 g) was obtained as a colourless gum by concentration of the required fraction under reduced pressure and drying by repetitive addition of acetonitrile and concentration under reduced pressure.

Mass spectrum: Found: MH$^+$ 476 ($^{35}$Cl).

INTERMEDIATE 35

{2-[3-Chloro-5-(ethyl-phenyl-carbamoyl)-phenoxy]-ethyl}-pyridin-4-yl-carbamic acid tert-butyl ester To a stirred solution of 3-[2-(tert-butoxycarbonyl-pyridin-4-yl-amino)ethoxy]-5-chloro-benzoic acid (0.060 g), TBTU (0.096 g) and HOBt (0.030 g) in DMF (1 ml) was added DIPEA (0.052 ml) followed by N-ethylaniline (0.038 ml) after 15 min. The reaction mixture was stirred at room temperature for 66 h and then concentrated under reduced pressure. The residue was subjected to preparative hplc and the title compound (0.080 g) was obtained as a colourless gum by concentration of the required fraction under reduced pressure and drying by repetitive addition of acetonitrile and concentration under reduced pressure.

Mass spectrum: Found: MH$^+$ 496 ($^{35}$Cl).

INTERMEDIATE 36

3-Chloro-N-(3,5-difluoro-phenyl)-5-methoxy-N-propyl-benzamide

2M Oxalyl chloride solution in dichloromethane (0.210 ml) and DMF (0.010 ml) were added to a solution of 3-chloro-5-methoxy-benzoic acid (0.373 g) in anhydrous dichloromethane (20 ml). The reaction was stirred at room temperature for 2 h then N-propyl-2,5-difluoroaniline (0.408 g), DMAP (0.010 g) and DIPEA (0.973 ml) were added. The reaction mixture was stirred at room temperature for 18 h, diluted with ethyl acetate and then extracted repeatedly with 2M hydrochloric acid until none of the aniline remained. The organic phase was dried with brine and over sodium sulphate and evaporated under reduced pressure to give the title compound (0.279 g) as a colourless gum.

Hplc system 1 ($\lambda$=254 nm) Rt 11.1 min.

INTERMEDIATE 37

3-Chloro-N-(3,5-difluoro-phenyl)-5-hydroxy-N-propyl-benzamide

To a stirred solution of 3-chloro-N-(3,5-difluoro-phenyl)-5-methoxy-N-propyl-benzamide (0.164 g) in anhydrous dichloromethane (5 ml) at −78° C. was added 1M boron tribromide solution in dichloromethane (3.5 ml). The reaction mixture was stirred at this temperature for 15 min. The reaction was allowed to warm to room temperature, and after 3.5 h the reaction was cooled to −78° C. and methanol (6 ml) added. The reaction was allowed to rewarm to room temperature and the solvent removed in vacuo. The residue was purified by flash column chromatography eluting with cyclohexane:ethyl acetate (3:1 v/v) to give the title compound as a colourless oil (0.110 g).

Hplc system 1 ($\lambda$=254 nm) Rt 9.1 min.

INTERMEDIATE 38

Toluene-4-sulfonic acid 2-(tert-butoxycarbonyl-pyridin-4-yl-amino)-ethyl ester

To a solution of pyridin-4-yl-carbamic acid tert-butyl ester[2] (14.0 g) in dry DMF (200 ml) was added sodium hydride (60% dispersion in mineral oil, 3.17 g) and ethylene glycol tosylate (26.7 g). The reaction mixture was stirred for 16 h. Water (150 ml) was added and the mixture extracted with ethyl acetate, washed with brine (75 ml), dried (MgSO$_4$) and concentrated under reduced pressure. The residue was purified by flash chromatography using eluting with chloroform:methanol (49:1 v/v) to give the title compound as a brown oil (10.7 g).

Mass spectrum found: MH$^+$ 393.

INTERMEDIATE 39

(2-{3-Chloro-5-[(propyl)-(3,5-difluoro-phenyl)-carbamoyl]-phenoxy}-ethyl)-pyridin-4-yl-carbamic acid tert-butyl ester To a solution of 3-chloro-N-(3,5-difluoro-phenyl)-5-hydroxy-N-propyl-benzamide (0.050 g) in DMF (0.5 ml) stirred at room temperature under nitrogen was added sodium hydride (60% dispersion in oil, 0.007 g) and after 10 min was added toluene-4-sulfonic acid 2-(tert-butoxycarbonyl-pyridin-4-yl-amino)-ethyl ester (0.060 g). The reaction was stirred for 66 h, quenched with water and then concentrated in vacuo. and the residue subjected to preparative hplc. The title compound (0.029 g) was obtained as an colourless gum by concentration of the required fraction under reduced pressure and drying by repetitive addition of acetonitrile.

Hplc system 1 ($\lambda$=254 nm) Rt 11.1 min.

INTERMEDIATE 40

(2-{3-Chloro-5-[(2-cyano-ethyl)-(2-fluoro-phenyl)-carbamoyl]-phenoxy}-ethyl)-pyridin-4-yl-carbamic acid tert-butyl ester 2M Oxalyl chloride solution in dichloromethane (0.090 ml) and DMF (0.001 ml) were added to a suspension of 3-[2-(tert-butoxycarbonyl-pyridin-4-yl-amino)-ethoxy]-5-chloro-benzoic acid (0.059 g) in anhydrous dichloromethane (1 ml). The reaction was stirred at room temperature for 1.5 h then a solution of 3-(2-fluoro-phenylamino)propionitrile (0.026 g) in dichloromethane (1 ml), DMAP (0.002 g) and DIPEA (0.078 m l) were added. The reaction mixture was stirred at room temperature for 66 h. The reaction mixture was partitioned between ethyl acetate and 1M aqueous hydrochloric acid. The aqueous layer was removed and the organic phase washed with further 1M aqueous hydrochloric acid, saturated aqueous sodium bicarbonate solution, water and dried with brine and over sodium sulphate and concentrated under reduced pressure. The residue was purified by flash column chromatography, eluting with ethyl acetate:cyclohexane (4:1 v/v), to give the title compound as a colourless gum (0.028 g).

Hplc system 1 ($\lambda$=254nm) Rt 9.7 min.

INTERMEDIATE 41

(2-{3-Chloro-5-[2-chloro-phenyl)-(2-cyano-ethyl)-(carbamoyl]-phenoxy}-ethyl)-pyridin-4-yl-carbamic acid tert-butyl ester 2M Oxalyl chloride solution in dichloromethane (0.090 ml) and DMF (0.001 ml) were added to a suspension of 3-[2-tert-butoxycarbonyl-pyridin-4-yl-amino)-ethoxy]-5-chloro-benzoic acid (0.059 g) in anhydrous dichloromethane (1 ml). The reaction was stirred at room temperature for 1.5 h then a solution of 3-(2-chloro-phenylamino)-propionitrile (0.029 g) in dichloromethane (1 ml), DMAP (0.002 g) and DIPEA (0.078 ml) were added. The reaction mixture was stirred at room temperature for 66 h. The reaction mixture was partitioned between ethyl acetate and water. The aqueous layer was removed and the organic phase washed with further 1M aqueous hydrochloric acid, saturated aqueous sodium bicarbonate solution, water and dried with brine and over sodium sulphate and concentrated under reduced pressure. The residue was purified by flash column chromatography, eluting with ethyl acetate:cyclohexane (4:1 v/v), to give the title compound as a colourless gum (0.040 g).

Hplc system 1 ($\lambda$=254 nm) Rt 9.7 min.

INTERMEDIATE 42

4-[{3-[2-(tert-Butoxycarbonyl-pyridin-4-yl-amino)-ethoxy]-5-chloro-benzoyl}-(2-fluoro-phenyl)-amino]-butyric acid methyl ester 2M Oxalyl chloride solution in dichloromethane (0.600 ml) and DMF (0.01 ml) were added to a suspension of 3-[2-(tert-butoxycarbonyl-pyridin-4-yl-amino)-ethoxy]-5-chloro-benzoic acid (0.393 g) in anhydrous dichloromethane (5 ml). The reaction was stirred at room temperature for 1 h then a solution of 4-(2-fluoro-phenylamino)-butyric acid methyl ester (0.422 g) in dichloromethane (1.5 ml), DMAP (0.006 g) and DIPEA (0.522 ml) were added. The reaction mixture was stirred at room temperature for 2 h. The reaction mixture was partitioned between ethyl acetate and saturated aqueous sodium bicarbonate. The aqueous layer was removed and the organic phase washed with 1M aqueous hydrochloric acid, saturated aqueous sodium bicarbonate solution, water and dried with brine and over sodium sulphate and concentrated under reduced pressure. The residue was purified by flash column chromatography, eluting with ethyl acetate:cyclohexane (4:1 v/v), to give the title compound as a colourless gum (0.287 g).

Hplc system 1 ($\lambda$=254 nm) Rt 10.5 min.

INTERMEDIATE 43

4-[{3-[2-tert-Butoxycarbonyl-pyridin-4-yl-amino)-ethoxy]-5-chloro-benzoyl}-(2-fluoro-phenyl)-amino]-butyric acid 2M Aqueous sodium hydroxide (0.75 ml) was added to a stirred solution of 4-({3-[2-(tert-butoxycarbonyl-pyridin-4-yl-amino)-ethoxy]-5-chloro-benzoyl}-(2-fluoro-phenyl)-amino)-butyric acid ethyl ester (0.270 g) in 1,4-dioxan (2 ml). 2M aqueous hydrochloric acid (1.0 ml) was added after 16 h. The reaction mixture was partitioned between ethyl acetate and water. The aqueous layer was removed and the organic phase was dried with brine and over sodium sulphate and then concentrated under reduced pressure to give the title compound (0.1 85 g) as a white foam.

Hplc system 1 ($\lambda$=254 nm) Rt 8.7 min.

INTERMEDIATE 44

(2-{3-[(3-Carbamoyl-propyl)-(2-fluoro-phenyl)-carbamoyl]-5-chloro-phenoxy}-ethyl)-pyridin-4-yl-carbamic acid tert-butyl ester To a stirred solution of 4-({3-[2-(tert-butoxycarbonyl-pyridin-4-yl-amino)-ethoxy]-5-chloro-benzoyl}-(2-fluoro-phenyl)-amino)-butyric acid (0.100 g), TBTU (0.112 g) and HOBt (0.047 g) in DMF (2 ml) was added DIPEA (0.060 ml) followed by a 0.5M solution of ammonia in 1,4-dioxane (0.70 ml) after 10 min. The reaction mixture was stirred at room temperature for 70 h and then concentrated under reduced pressure. The residue was subjected to preparative hplc and the title compound (0.100 g) was obtained as a colourless gum by concentration of the required fraction under reduced pressure and drying by repetitive addition of acetonitrile and concentration under reduced pressure.

Mass spectrum: Found: MH$^+$ 571 ($^{35}$Cl).

INTERMEDIATE 45

(2-{3-Chloro-5-[(2-fluoro-phenyl)-(4-oxo-4-pyrrolidin-1-yl-butyl)-carbamoyl]-phenoxy}-ethyl)-pyridin-4-yl-carbamic acid tert-butyl ester To a stirred solution of 4-({3-[2-(tert-butoxycarbonyl-pyridin-4-yl-amino)-ethoxy]-5-chloro-benzoyl}-(2-fluoro-phenyl)-amino)-butyric acid (0.025 g), TBTU (0.028 g) and HOBt (0.012 g) in DMF (1 ml) was added DIPEA (0.015 ml) followed by pyrrolidine (0.007 ml) after 10 min. The reaction mixture was stirred at room temperature for 16 h and then concentrated under reduced pressure. The residue was subjected to preparative hplc and the title compound (0.025 g) was obtained as a colourless gum by concentration of the required fraction under reduced pressure and drying by repetitive addition of acetonitrile and concentration under reduced pressure.

Mass spectrum: Found: MH$^+$ 625 ($^{35}$Cl).

INTERMEDIATE 46

4-[{3-[2-(tert-Butoxycarbonyl-pyridin-4-yl-amino)-ethoxy]-5-chloro-benzoyl}-(2-carbamoyl-phenyl)-amino]-butyric acid methyl ester 2M Oxalyl chloride solution in dichloromethane (0.090 ml) and DMF (0.01 ml) were added to a suspension of 3-[2-(tert-butoxycarbonyl-pyridin-4-yl-amino)-ethoxy]-5-chloro-benzoic acid (0.060 g) in anhydrous dichloromethane (1 ml). The reaction was stirred at room temperature for 2 h then 4-(2-carbamoyl phenylamino)-butyric acid methyl ester (0.037 g), DMAP (0.002 g) and DIPEA (0.078 ml) were added. The reaction mixture was stirred at room temperature for 18 h. The reaction mixture was partitioned between ethyl acetate and water. The aqueous layer was removed and the organic phase washed with saturated aqueous sodium bicarbonate solution, water and dried with brine and over sodium sulphate and concentrated under reduced pressure. The residue was purified by flash column chromatography, eluting with ethyl acetate:cyclohexane (9:1 v/v), neat ethyl acetate and dichloromethane:methanol (9:1) to give the title compound as a colourless gum (0.031 g).

Hplc system 1 ($\lambda$=254 nm) Rt 7.9 min.

INTERMEDIATE 47

(2-{3-Chloro-5-[(3-cyano-propyl)-2-fluoro-phenyl)-carbamoyl]-phenoxy}-ethyl)-pyridin-4-yl-carbamic acid tert-butyl ester 2M Oxalyl chloride solution in dichloromethane (0.300 ml) and DMF (0.01 ml) were added to a suspension of 3-[2-(tert-butoxycarbonyl-pyridin-4-yl-amino)-ethoxy]-5-chloro-benzoic acid (0.195 g) in anhydrous dichloromethane (5 ml). The reaction was stirred at room temperature for 2 h then 4-(2-fluoro-phenylamino)buyronitrile (0.178 g) as a solution in dichloromethane (1 ml), DMAP (0.012 g) and DIPEA (0.105 ml) were added. The reaction mixture was stirred at room temperature for 40 h. The reaction mixture was partitioned between ethyl acetate and saturated aqueous sodium bicarbonate. The aqueous layer was removed and the organic phase washed with 1M aqueous hydrochloric acid, saturated aqueous sodium bicarbonate, water and dried with brine and over sodium sulphate and concentrated under reduced pressure. The residue was purified by flash column chromatography. eluting with ethyl acetate:cyclohexane (1:1 v/v) and neat ethyl acetate, to give the title compound as a colourless gum (0.132 g).

Hplc system 1 ($\lambda$=254 nm) Rt 9.2 min.

INTERMEDIATE 48

[2-(3-Chloro-5-{[2-(2,2-dimethyl-[1,3]dioxolan-4-ylmethoxy)-ethyl]-phenyl-carbamoyl}-phenoxy)-ethyl]-pyridin-4-yl-carbamic acid tert-butyl ester 2M Oxalyl chloride solution in dichloromethane (0.115 ml) and DMF (0.005 ml) were added to a suspension of 3-[2-tert-butoxycarbonyl-pyridin-4-yl-amino)-ethoxy]-5-chloro-benzoic acid (0.060 g) in anhydrous dichloromethane (5 ml). The reaction was stirred at room temperature for 1 h then a mixture of [2-(2,2-dimethyl-[1,3]dioxolan-4-ylmethoxy)ethyl]-phenyl-amine and toluene-4-sulfonic acid 2,2-dimethyl-[1,3]dioxolan-4-ylmethyl ester compound (0.194 g in a ratio of 2:1 mol/mol), DMAP (0.005 g) and DIPEA (0.080 ml) were added. The reaction mixture was stirred at room temperature for 20 h. The reaction mixture was diluted with further dichloromethane and extracted with saturated aqueous sodium bicarbonate. The aqueous layer was removed and the organic phase washed with 1M aqueous hydrochloric acid, saturated aqueous sodium bicarbonate, water and dried with brine and over sodium sulphate and concentrated under reduced pressure. The residue was purified by flash column chromatography, eluting with ethyl acetate:petroleum ether (1:1 v/v) and neat ethyl acetate, to give the title compound as a colourless gum (0.037 g).

Hplc system 1 ($\lambda$=254 nm) Rt 11.1 min.

INTERMEDIATE 49

(2-{3-Chloro-5-[[2-(2,2-dimethyl-[1,3]dioxolan-4-ylmethoxy)-ethyl]-(2-fluoro-phenyl)-carbamoyl]-phenoxy}-ethyl)-pyridin-4-yl-carbamic acid tert-butyl ester 2M Oxalyl chloride solution in dichloromethane (0.115 ml), and DMF (0.005 ml) were added to a suspension of 3-[2-(tert-butoxycarbonyl-pyridin-4-yl-amino)-ethoxy]-5-chloro-benzoic acid (0.060 g) in anhydrous dichloromethane (5 ml). The reaction was stirred at room temperature for 1.5 h then [2-(2,2-dimethyl-[1,3]dioxolan-4-ylmethoxy)-ethyl]-(2-fluoro-phenyl)-amine (0.121 g) as a solution in dichloromethane (0.5 ml), DMAP (0.005 g) and DIPEA (0.080 ml) were added. The reaction mixture was stirred at room temperature for 20 h. The reaction mixture was diluted with further dichloromethane and extracted with saturated aqueous sodium bicarbonate. The aqueous layer was removed and the organic phase washed with water and dried with brine and over sodium sulphate and concentrated under reduced pressure. The residue was purified by flash column chromatography, eluting with ethyl acetate:petroleum ether (1:1, 2:1 and 4:1 v/v) and neat ethyl acetate, to give the title compound as a colourless gum (0.035 g).

Hplc system 1 ($\lambda$=254 nm) Rt 11.0 min.

INTERMEDIATE 50

(2-{3-Chloro-5-[[2-(2,2-dimethyl-[1,3]dioxolan-4-ylmethoxy)-ethyl]-(4-fluoro-phenyl)-carbamoyl]-phenoxy}-ethyl)-pyridin-4-yl-carbamic acid tert-butyl ester 2M Oxalyl chloride solution in dichloromethane (0.115 ml) and DMF (0.005 ml) were added to a suspension of 3-[2-(tert-butoxycarbonyl-pyridin-4-yl-amino)-ethoxy]-5-chloro-benzoic acid (0.060 g) in anhydrous dichloromethane (5 ml). The reaction was stirred at room temperature for 1.5 h then [2-(2,2-dimethyl-[1,3]dioxolan-4-ylmethoxy)-ethyl]-(4-fluoro-phenyl)-amine (0.078 g) as a solution in dichloromethane (0.5 ml), DMAP (0.002 g) and DIPEA (0.080 ml) were added. The reaction mixture was stirred at room temperature for 16 h. The reaction mixture was diluted with further dichloromethane and extracted with saturated aqueous sodium bicarbonate. The aqueous layer was removed and the organic phase washed with water and dried with brine and over sodium sulphate and concentrated under reduced pressure. The residue was purified by flash column chromatography, eluting with ethyl acetate:petroleum ether (1:1, 2:1 and 4:1 v/v), to give the title compound as a colourless gum (0.037 g).

Hplc system 1 ($\lambda$=254 nm) Rt 11.2 min.

INTERMEDIATE 51

(R)-1-{3-[{3-[2-(tert-Butoxycarbonyl-pyridin-4-yl-amino)-ethoxy]-5-chloro-benzoyl}-(2-fluoro-phenyl)-amino]-propyl}-pyrrolidine-2-carboxylic acid tert-butyl ester and (R)-1-[3-(2-fluoro-phenylamino)-propyl]-pyrrolidine-2-carboxylic acid tert butyl ester 2M Oxalyl chloride solution in dichloromethane (0.112 ml) and DMF (0.005 ml) were added to a suspension of 3-[2-tert-butoxycarbonyl-pyridin-4-yl-amino)-ethoxy]-5-chloro-benzoic acid (0.060 g) in anhydrous dichloromethane (2.0 ml). The reaction was stirred at room temperature for 1 h then a mixture of (R)-1-[3-(2-fluoro-phenylamino)-propyl]-pyrrolidine-2-carboxylic acid tert-butyl ester (0.145 g), DMAP (0.002 g) and DIPEA (0.080 ml) as a solution in dichloromethane (0.4 ml) was added. The reaction mixture was stirred at room temperature for 18 h and evaporated in vacuo. The residue was purified by preparative hplc give the title compounds as a colourless gum (0.110 g) by concentration of the required fraction under reduced pressure and drying by repetitive addition of acetonitrile and concentration under reduced pressure.

Hplc system 1 ($\lambda$=254 nm); Rt 8.3 min ((R)-1-[3-(2-fluoro-phenylamino)-propyl]-pyrrolidine-2-carboxylic acid tert butyl ester); Rt 9.7 min ((R)-1-{3-[{3-[2-(tert-butoxycarbonyl-pyridin-4-yl-amino)-ethoxy]-5-chloro-benzoyl}-(2-fluoro-phenyl)-amino]-propyl}-pyrrolidine-2-carboxylic acid tert-butyl ester).

INTERMEDIATE 52

3-({3-[2-(tert-Butoxycarbonyl-pyridin-4-yl-amino)-ethoxy]-5-chloro-benzoyl}-phenyl-amino)-propionic acid methyl ester 2M Oxalyl chloride solution in dichloromethane (1.8 ml), and DMF (0.05 ml) were added to a suspension of 3-[2-(tert-butoxycarbonyl-pyridin-4-yl-amino)-ethoxy]-5-chloro-benzoic acid (1.18 g) in anhydrous dichloromethane (30 ml). The reaction was stirred at room temperature for 1 h then 3-phenylamino-propionic acid methyl ester (0.644 g), DMAP (0.036 g) and DIPEA (1.04 ml) were added. The reaction mixture was stirred at room temperature for 20 h and partitioned between ethyl acetate and 1M aqueous hydrochloric acid. The aqueous layer was removed and the organic phase washed with saturated aqueous sodium bicarbonate, water and dried with brine and over sodium sulphate and concentrated under reduced pressure. The residue was purified by flash column chromatography, eluting with ethyl acetate:petroleum ether (4:1 v/v) and neat ethyl acetate, to give the title compound as a colourless gum (1.22 g).

Hplc system 1 ($\lambda$=254 nm) Rt 9.8 min.

INTERMEDIATE 53

3-({3-[2-(tert-Butoxycarbonyl-pyridin-4-yl-amino)-ethoxy]-5-chloro-benzoyl}-phenyl-amino)-propionic acid 2M Aqueous sodium hydroxide (2.54 ml) was added to a stirred solution of 3-({3-[2-(tert-butoxycarbonyl-pyridin-4-yl-amino)-ethoxy]-5-chloro-benzoyl}-phenyl-amino)-propionic acid methyl ester (1.22 g) in 1,4-dioxan (15 ml). 2M Aqueous hydrochloric acid (2.54 ml) was added after 16 h. The reaction mixture was evaporated and the residue partitioned between ethyl acetate and water. The aqueous layer was removed and the organic phase was dried with brine and over sodium sulphate and then concentrated under reduced pressure to give the title compound (1.10 g) as a white foam.

Mass spectrum: Found: MH$^+$ 540 ($^{35}$Cl).

INTERMEDIATE 54

(2-{3-Chloro-5-[(2-fluorosulfonyl-ethyl)-phenyl-carbamoyl]-phenoxy}-ethyl)-pyridin-4-yl-carbamic acid tert-butyl ester 2M Oxalyl chloride solution in dichloromethane (0.9 ml) and DMF (0.025 ml) were added to a suspension of 3-[2-(tert-butoxycarbonyl-pyridin-4-yl-amino)-ethoxy]-5-chloro-benzoic acid (0.610 g) in anhydrous dichloromethane (50 ml). The reaction was stirred at room temperature for 1 h then 2-phenylamino-ethanesulfonyl fluoride(0.257 g), DMAP (0.018 g) and DIPEA (0.261 ml) were added. The reaction mixture was stirred at room temperature for 20 h and partitioned between ethyl acetate and 1M aqueous hydrochloric acid. The aqueous layer was removed and the organic phase washed with saturated aqueous sodium bicarbonate, water and dried with brine and over sodium sulphate and concentrated under reduced pressure. The residue was purified by flash column chromatography, eluting with using ethyl acetate:petroleum ether (3:1 v/v) to give the title compound as a white foam (0.40 g).

Hplc system 1 ($\lambda$=254 nm) Rt 10.3 min.

INTERMEDIATE 55

3-[(3-Chloro-5-methoxy-benzoyl)-isopropyl-amino]-propionic acid methyl ester

To a stirred solution of 3-chloro-5-methoxy-benzoic acid (0.932 g), TBTU (3.21 g) and in DMF (10 ml) was added DIPEA (1.73 ml) followed by 3-isopropylamino propionic acid methyl ester (0.871 g) after 10 min. The reaction mixture was stirred at room temperature for 48 h and then concentrated under reduced pressure. The residue was partitioned between ethyl acetate and water. The organic phase was washed with further water and 2M aqueous sodium hydroxide, water and dried with brine and over sodium sulphate and concentrated under reduced pressure to give the title compound as a brown oil (1.6 g).

Mass spectrum: Found: MH$^+$ 314.

INTERMEDIATE 56

3-[(3-Chloro-5-methoxy-benzoyl)-isopropyl-amino]-propionic acid

2M Aqueous sodium hydroxide (4.5 ml) was added to a stirred solution of 3-[(3-chloro-5-methoxy-benzoyl)-isopropyl-amino]-propionic acid methyl ester (1.50 g) in 1,4-dioxan (30 ml). 2M aqueous hydrochloric acid (4.5 ml) was added after 20 h. The reaction mixture was evaporated and the residue partitioned between ethyl acetate and water. The aqueous layer was removed and the organic phase was dried with brine and over sodium sulphate and then concentrated under reduced pressure to give the title compound (1.41 g) as a brown solid.

Mass spectrum: Found: MH$^+$ 300 ($^{35}$Cl).

INTERMEDIATE 57

3-Chloro-N-isopropyl-5-methoxy-N-(2-methylcarbamoyl-ethyl)-benzamide

To a stirred solution of 3-[(3-chloro-5-methoxy-benzoyl)-isopropyl-amino]-propionic acid (0.600 g), TBTU (1.28 g) in DMF (10 ml) was added DIPEA (0.696 ml) followed a 2M solution of methylamine in THF (8.0 ml) after 10 min. The reaction mixture was stirred at room temperature for 4 h and then concentrated under reduced pressure. The residue was partitioned between ethyl acetate and water. The organic phase was washed with further water and 1M aqueous hydrochloric acid, saturated aqueous sodium bicarbonate, water and dried with brine and over sodium sulphate and concentrated under reduced pressure to give the title compound as a brown oil (0.575 g).

Mass spectrum: Found: MH$^+$ 313 ($^{35}$Cl).

INTERMEDIATE 58

3-Chloro-N-isopropyl-5-methoxy-N-[2-(1-methyl-1H-tetrazol-5-yl)ethyl]-benzamide To a stirred solution of 3-chloro-N-isopropyl-5-methoxy-N-(2-methylcarbamoyl-ethyl)-benzamide (0.312 g) in anhydrous dichloromethane (5.0 ml) was added sodium azide (0.065 g) and the mixture cooled to 0° C. Trifluoromethanesulphonic anhydride (0.200 ml) was added and the reaction stirred at room temperature for 18 h. The reaction mixture was partitioned between ethyl acetate and water. The aqueous layer was removed and the organic layer dried with brine and over sodium sulphate and concentrated under reduced pressure. The residue was purified by flash column chromatography, eluting with ethyl acetate:petroleum ether (4:1 v/v); to give the title compound as a white solid (0.121 g).

Hplc system 1 ($\lambda$=254 nm) Rt 8.2 min.

INTERMEDIATE 59

3-Chloro-5-hydroxy-N-isopropyl-N-[2-(1-methyl-1H-tetrazol-5-yl)-ethyl]-benzamide To a stirred solution of 3-chloro-N-isopropyl-5-methoxy-N-[2-(1-methyl-1H-tetrazol-5-yl)-ethyl]-benzamide (0.115 g) in anhydrous dichloromethane (5.0 ml) at −78° C. was added 1M boron tribromide solution in dichloromethane (1.36 ml). The reaction mixture was stirred at this temperature for 15 min. The reaction was allowed to warm to room temperature. After 24 h, the reaction was cooled to −78° C. and methanol (1 ml) added. The reaction was allowed to rewarm to room temperature and absorbed on to silica. This was loaded on to an already prepared flash column, eluting with ethyl acetate:petroleum ether (4:1 v/v) and 25:1 dichloromethane:methanol (25:1 v/v) to give the title compound as a white solid (0.072 g).

Hplc system 1 ($\lambda$=254 nm) Rt 6.6 min.

INTERMEDIATE 60

[2-(3-Chloro-5-{isopropyl-[2-(1-methyl-1H-tetrazol-5-yl)-ethyl]-carbamoyl}-phenoxy)-ethyl]-pyridin-4-yl-carbamic acid tert-butyl ester To a solution of 3-chloro-5-hydroxy-N-isopropyl-N-[2-(1-methyl-1H-tetrazol-5-yl)-ethyl]-benzamide (0.070 g) in DMF (2.0 ml) stirred at room temperature under nitrogen was added sodium hydride (60% dispersion in oil, 0.010 g) and after 10 min was added toluene-4-sulfonic acid 2-(tert-butoxycarbonyl-pyridin-4-yl-amino)-ethyl ester (0.120 g). The reaction was stirred for 88 h and the sovent removed in vacuo. The residue was partitioned between ethyl acetate and water. The organic phase was washed with further water and 1M aqueous sodium hydroxide, water and dried with brine and over sodium sulphate and concentrated under reduced pressure to give the crude product which was purified by flash column chromatography, eluting with ethyl acetate:petroleum ether (4:1 v/v) and 24:1 dichloromethane:methanol (24:1 v/v), to give the title compound as a colourless gum (0.028 g).

Hplc system 1 ($\lambda$=254 nm) Rt 8.3 min.

INTERMEDIATE 61

(2-{3-Chloro-5-[cyclopentyl-(3-trifluoromethanesulfonylamino-propyl)-carbamoyl]-phenoxy}-ethyl)-pyridin-4-yl-carbamic acid tert-butyl ester To a stirred solution of 3-[2-(tert-butoxycarbonyl-pyridin-4-yl-amino)-ethoxy]-5-chloro-benzoic acid (0.059 g), TBTU (0.072 g), and HOBt (0.034 g) in DMF (1 ml) was added DIPEA (0.078 ml) followed by N-(3-cyclopentylamino-propyl)-C,C,C-trifluoromethanesulfonamide formate (0.053 g) after 5 min. The reaction mixture was stirred at room temperature for 4 days then more TBTU (0.072 g), HOBt (0.034 g) and DIPEA (0.078 ml) were added followed by more of the secondary amine (0.06 g). The mixture was heated to 60° C. for 3 h, the solvent was removed by evaporation at reduced pressure and the residue subjected to preparative hplc. This gave the title compound as a colourless gum (0.012 g).

Hplc system 1 ($\lambda$=254 nm) Rt 12.5 min.

INTERMEDIATE 62

[2-(3-{[2-(3-Amino-[1,2,4]oxadiazol-5-yl)-ethyl]-isopropyl-carbamoyl}-5-chloro-phenoxy)-ethyl]-pyridin-4-yl-carbamic acid tert-butyl ester To a stirred solution of 3-[2-(tert-butoxycarbonyl-pyridin-4-yl-amino)-ethoxy]-5-chloro-benzoic acid (0.104 g), TBTU (0.128 g), and HOBt (0.061 g) in DMF (1 ml) was added DIPEA (0.139 ml) and 5-(2-isopropylamino-ethyl)-[1,2,4]oxadiazol-3-ylamine (0.05 g). The reaction mixture was stirred at room temperature for 10 days, then silica was added and the solvent removed by evaporation at reduced pressure. The resulting silica was loaded onto the top of a column of silica which was then eluted with a gradient [cyclohexane:ethyl acetate (1:1 v/v) to neat ethyl acetate to ethyl acetate:methanol (9:1 v/v)]. Concentration of the required fraction at reduced pressure furnished the title compound as a yellow glass (0.069 g).

Hplc system 1 ($\lambda$=254 nm) Rt 8.2 min.

INTERMEDIATE 63

(2-{3-Chloro-5-[(2-cyano-ethyl)-cyclopropylmethyl-carbamoyl]-phenoxy}-ethyl)-pyridin-4-yl-carbamic acid tert-butyl ester To a stirred solution of 3-[2-(tert-butoxycarbonyl-pyridin-4-yl-amino)-ethoxy]-5-chloro-benzoic acid (0.060 g), TBTU (0.096 g) and HOBt (0.030 g) in DMF (1 ml) was added DIPEA (0.052 ml) followed by 3-(cyclopropylmethyl-amino)-propionitrile[4] (0.044 g) after 15 min. The reaction was stirred at room temperature for 14 h, and then concentrated under reduced pressure. The residue was subjected to preparative hplc and the title compound (0.070 g) was obtained as a brown oil by concentration of the required fraction under reduced pressure and drying by repetitive addition of acetonitrile and concentration under reduced pressure.

Mass spectrum: Found: MH$^+$ 499 ($^{35}$Cl).

INTERMEDIATE 64

(2-{3-Chloro-5-[(2-cyano-ethyl)-(2,2-dimethyl-propyl)-carbamoyl]-phenoxy}-ethyl)-pyridin-4-yl-carbamic acid tert-butyl ester To a stirred solution of 3-[2-(tert-butoxycarbonyl-pyridin-4-yl-amino)-ethoxy]-5-chloro benzoic acid (0.060 g), TBTU (0.096 g) and HOBT (0.030 g) in DMF (1 ml) was added DIPEA (0.052 ml) followed by 3-(2,2-dimethyl-propylamino)-propionitrile[5] (0.043 g) after 15 min. The reaction was stirred at room temperature for 18 h, and then concentrated under reduced pressure. The residue was subjected to preparative hplc and the title compound (0.053 g) was obtained as a colourless oil by concentration of the

INTERMEDIATE 65

(2-{3-Chloro-5-[(2-cyano-ethyl)-(tetrahydro-furan-2-ylmethyl)-carbamoyl]-phenoxy}-ethyl)-pyridin-4-yl-carbamic acid tert-butyl ester To a stirred solution of 3-[2-(tert-butoxycarbonyl-pyridin-4-yl-amino)-ethoxy]-5-chloro-benzoic acid (0.060 g), TBTU (0.096 g) and HOBT (0.030 g) in DMF (1 ml) was added DIPEA (0.052 ml) followed by 3-[(tetrahydro-furan-2-ylmethyl)-amino]-propionitrile (0.047 g) after 15 min. The reaction was stirred at room temperature for 96 h, and then concentrated under reduced pressure. The residue was subjected to preparative hplc and the title compound (0.078 g) was obtained as a brown oil by concentration of the required fraction under reduced pressure and drying by repetitive addition of acetonitrile and concentration under reduced pressure.

Mass spectrum: Found: MH$^+$ 529 ($^{35}$Cl).

INTERMEDIATE 66

(2-{3-Chloro-5-[(2-cyano-ethyl)-isopropyl-carbamoyl]-phenoxy}-ethyl)-pyridin-4-carbamic acid tert-butyl ester To a stirred solution of 3-[2-tertbutoxycarbonyl-pyridin-4-yl-amino)-ethoxy]-5-chloro-benzoic acid (0.060 g), TBTU (0.096 g) and HOBT (0.030 g) in DMF (1 ml) was added DIPEA (0.052 ml) followed by 34sopropylamino propionitrile$^6$ (0.034 g) after 15 min. The reaction was stirred at room temperature for 96 h, and then concentrated under reduced pressure. The residue was subjected to preparative hplc and the title compound (0.072 g) was obtained as a brown oil by concentration of the required fraction under reduced pressure and drying by repetitive addition of acetonitrile and concentration under reduced pressure.

Mass spectrum: Found: MH$^+$ 487 (35Cl).

INTERMEDIATE 67

(2-{3-Chloro-5-[(2-cyano-ethyl)-isobutyl-carbamoyl]-phenoxy}-ethyl)-pyridin-4-yl-carbamic acid tert-butyl ester To a stirred solution of 3-[2-(tert-butoxycarbonyl-pyridin-4-yl-amino)-ethoxy]-5-chloro-benzoic acid (0.060 g), TBTU (0.096 g) and HOBT (0.030 g) in DMF (1 ml) was added DIPEA (0.052 ml) followed by 3-isobutylamino-propionitrile$^7$ (0.038 g) after 15 min. The reaction was stirred at room temperature for 18 h, and then concentrated under reduced pressure. The residue was subjected to preparative hplc and the title compound (0.060 g) was obtained as a colourless oil by concentration of the required fraction under reduced pressure and drying by repetitive addition of acetonitrile and concentration under reduced pressure.

Mass spectrum: Found: MH$^+$ 501 ($^{35}$Cl).

INTERMEDIATE 68

3-({3-[2-(tert-Butoxycarbonyl-pyridin-4-yl-amino)-ethoxy]-5-chloro-benzoyl}-isopropyl-amino)-propionic acid methyl ester trifluoroacetate To a stirred solution of 3-[2-(tert-butoxycarbonyl-pyridin-4-yl-amino)-ethoxy]-5-chloro-benzoic acid (0.344 g), TBTU (0.549 g) and HOBT (0.173 g) in DMF (6 ml) was added DIPEA (0.296 ml) followed by 3-isopropylamino-propionic acid methyl ester (0.254 g) after 15 min. The reaction was stirred at room temperature for 24 h, and then concentrated under reduced pressure. The residue was partitioned between saturated sodium bicarbonate solution and ethyl acetate. The aqueous layer was separated and extracted with further ethyl acetate. The combined, dried (MgSO$_4$) organic fractions were concentrated under reduced pressure. The residue was subjected to preparative hplc to give the title compound (0.332 g) as a colourless oil, by concentration of the required fraction under reduced pressure and drying by repetitive addition of acetonitrile and concentration under reduced pressure.

Hplc system 1 ($\lambda$=254 nm) Rt 9.7 min.

INTERMEDIATE 69

3-({3-[2-(tert-Butoxycarbonyl-pyridin-4-yl-amino)-ethoxy]-5-chloro-benzoyl}-isopropyl-amino)-propionic acid hydrochloride To a solution of 3-({3-[2-(tert-butoxycarbonyl-pyridin-4-yl-amino)-ethoxy]-5-chloro-benzoyl}-isopropyl-amino)-propionic acid methyl ester trifluoroacetate (0.33 g) in dioxan (3 ml) was added 2M sodium hydroxide 0.95 ml, and the resultant solution was stirred at room temperature for 3 h. 1M Hydrochloric acid (ca. 4 ml) was added and the resultant suspension extracted with ethyl acetate. The combined, dried (MgSO$_4$) extracts were concentrated under reduced pressure to give the title compound (0.201 g) as a colourless oil.

Mass spectrum: Found: MH$^+$ 506 ($^{35}$Cl).

INTERMEDIATE 70

(2-{3-Chloro-5-[(2-diethylcarbamoyl-ethyl)-isopropyl-carbamoyl]-phenoxy}-ethyl)-pyridin-4-yl-carbamic acid tert-butyl ester trifluoroacetate To a stirred solution of 3-({3-[2-(tert-butoxycarbonyl-pyridin-4-yl-amino)-ethoxy]-5-chloro-benzoyl}-isopropyl-amino)-propionic acid hydrochloride (0.052 g), TBTU (0.064 g) and HOBT (0.027 g) in DMF (1 ml) was added DIPEA (0.035 ml) followed diethylamine (0.021 ml) after 15 min. The reaction was stirred at room temperature for 3 days, and then concentrated under reduced pressure. The residue was subjected to preparative hplc and the title compound (0.065 g) was obtained as a colourless oil by concentration of the required fraction under reduced pressure and drying by repetitive addition of acetonitrile and concentration under reduced pressure.

Mass spectrum: Found: MH$^+$ 561 ($^{35}$Cl).

INTERMEDIATE 71

1-{3-[2-(tert-Butoxycarbonyl-pyridin-4-yl-amino)-ethoxy]-5-chloro-benzoyl}-piperidine-2-carboxylic acid ethyl ester To a stirred solution of 3-[2-(tert-butoxycarbonyl-pyridin-4-yl-amino)-ethoxy]-5-chloro-benzoic acid (0.12 g) in dichloromethane (4 ml) was added dimethylformamide (0.05 ml) followed by 2M oxalyl chloride solution in dichloromethane (0.183 ml). The resultant solution was stirred at room temperature for 1 h, and then ethyl pipecolinate (0.096 g) followed by DIPEA (0.160 ml) were added. After 18 h, the reaction mixture was concentrated under reduced pressure and the residue was subjected to preparative hplc. The title compound (0.165 g) was obtained as a colourless oil by concentration of the required fraction under reduced pressure and drying by repetitive addition of acetonitrile and concentration under reduced pressure.

Mass spectrum: Found: MH+532 (35Cl).

INTERMEDIATE 72

{2-[3-Chloro-5-(2-methyl-piperidine-1-carbonyl)-phenoxy]-ethyl}-pyridin -4-yl-carbamic acid tert-butyl ester To a stirred solution of 3-[2-(tert-butoxycarbonyl-pyridin-4-yl-amino)-ethoxy]-5-chloro-benzoic acid (0.060 g) in dichloromethane (4 ml) was added DMF (0.025 ml) followed by 2M oxalyl chloride solution in dichloromethane (0.091 ml). The resultant solution was stirred at room temperature for 1 h, and then 2-methylpiperidine (0.03 g) followed by DIPEA (0.080 ml) were added. After 3 h, the solution was concentrated under reduced pressure and the residue was subjected to preparative hplc. The title compound (0.080 g) was obtained as a colourless oil by concentration of the required fraction under reduced pressure and drying by repetitive addition of acetonitrile and concentration under reduced pressure.

Hplc system 1 ($\lambda$=254 nm) Rt 10.4 min.

INTERMEDIATE 73

(2-{3-Chloro-5-[(2-cyano-ethyl)-cyclopentyl-carbamoyl]-phenoxy}-ethyl)-pyridin-4-yl-carbamic acid tert-butyl ester To a stirred solution of 3-[2-(tert-butoxycarbonyl-pyridin-4-yl-amino)-ethoxy]-5-chloro-benzoic acid (0.100 g), TBTU (0.080 g) and HOBt (0.034 g) in DMF (3 ml) was added DIPEA (0.087 ml) followed by 3-(cyclopentylamino) propionitrile (0.035 g) after 15 min. The reaction mixture was stirred at room temperature for 18 h and then concentrated under reduced pressure. The residue was washed with water and extracted with ethyl acetate. The organic layer was dried with brine and MgSO$_4$, filtered and concentrated to give the title compound (0.190 g) as a brown oil.

Mass spectrum: Found: MH$^+$ 513 ($^{35}$Cl).

INTERMEDIATE 74

(2-{3-Chloro-5-[isopropyl-(2-[1,2,4]triazol-1-yl-ethyl)-carbamoyl]-phenoxy}-ethyl)-pyridin-4-yl-carbamic acid tert-butyl ester To a stirred solution of 3-[2-(tert-butoxycarbonyl-pyridin-4-yl-amino)-ethoxy]-5-chloro-benzoic acid (0.1 g) in DMF (1 ml) and dichloromethane (3 ml), was added 2M oxalyl chloride in dichloromethane (0.153 ml) and after 30 min, a catalytic amount of DMAP and DIPEA (0.013 ml), followed by 2-(2-isopropylamino-ethyl)-N-[1,2,4]-triazole (0038 g). The reaction mixture was stirred at room temperature for 18 h and then concentrated under reduced pressure. The residue was washed with water and extracted with ethyl acetate. The organic layer was dried with brine and MgSO$_4$, filtered and concentrated to give the title compound (0.097 g) as a brown oil.

Mass spectrum: Found: MH$^+$ 529 ($^{35}$Cl).

INTERMEDIATE 75

(2-{3-[(3-Amino-propyl)-isopropyl-carbamoyl]-5-chloro-phenoxy}-ethyl)-pyridin-4-yl-carbamic acid tert-butyl ester A solution of (2-{3-chloro-5-[(-cyano-ethyl)-isopropyl-carbamoyl]-phenoxy}-ethyl)-pyridin-4yl-carbamic acid tert-butyl ester (0.200 g) in methanol (2 ml) at 0° C. was treated with cobalt (II) chloride hexahydrate (0.195 g) and sodium borohydride (0.078 g) and stirred overnight at room temperature. Silica was added and the mixture was evaporated under reduced pressure, the residue was subjected to flash chromatography eluting with methanol:chloroform:ammonia(0.88) (10:89:1 v/v/v). The required fractions were evaporated under reduced pressure to give the title compound as a pale straw coloured oil (0.128 g).

Hplc system 1 ($\lambda$=254 nm) Rt 6.5 min.

INTERMEDIATE 76

(2-{3-Chloro-5-[isopropyl-(3-trifluoromethanesulfonylamino-propyl)-carbamoyl]-phenoxy}-ethyl)-pyridin-4-yl-carbamic acid tert-butyl ester trifluoroacetate To a solution of (2-{3-[(3-amino-propyl)-isopropyl-carbamoyl]-5-chloro-phenoxy}-ethyl)-pyridin-4-yl-carbamic acid tert-butyl ester (0.044 g) and triethylamine (0.024 ml) in dichloromethane (1 ml) at −70° C. was added trifluoromethanesulphonic anhydride (0.016 ml), and the mixture was stirred overnight at room temperature. The mixture was diluted with dichloromethane(4 ml) and washed with saturated sodium bicarbonate(2 ml), dried (sodium sulphate) and evaporated under reduced pressure. The residue was subjected to preparative hplc to give the title compound (0.022 g). Hplc system 1 ($\lambda$=254 nm) Rt 11.4 min.

INTERMEDIATE 77

{2-[3-Chloro-5-(2,5-dimethyl-pyrrolidine-1-carbonyl)-phenoxy]-ethyl}-pyridin-4yl-carbamic acid tert-butyl ester 2,5-Dimethylpyrrolidine (0.14 ml) in DMF (1 ml) was added to a mixture of 3-[2-tert-butoxycarbonyl-pyridin-4yl-amino)ethoxy]-5-chlorobenzoic acid (0.30 g), HOBT (0.10 g), TBTU (0.37 g), and DIPEA (0.30 ml) in DMF (1 ml) and stirred overnight at room temperature. The mixture was diluted with water, extracted with ether, the ether layer was washed with water, brine, dried over sodium sulphate and evaporated under reduced pressure. The residue was subjected to flash chromatography eluting with ethyl acetate:cyclohexane (80:20 v/v) to give the title compound as an oil (0.27 g).

Tlc Rf(Silica gel 60 F$_{254}$)=0.2[ethyl acetate:cyclohexane (80:20 v/v)].

INTERMEDIATE 78

[2-(3-chloro-5-{[3-(2,2-dimethyl-prorpionylamino)-propyl]-isopropyl-carbamoyl}-phenoxy)-ethyl]-pyridine-4-yl-carbamic acid tert-butyl ester To a solution of (2-{3-[(3-amino-propyl)-isopropyl carbamoyl]-5-chloro-phenoxy}-ethyl)-pyridin-4-yl-carbamic acid tert-butyl ester (0.040 g) and DIPEA (0.030 ml) in dichloromethane (1 ml) was added a solution of trimethylacetyl chloride (0.012 ml) in dichloromethane (1 ml) and the mixture was stirred for 3 h at room temperature. The mixture was evaporated under reduced pressure to give the title compound.

Hplc system 1 ($\lambda$=254 nm) Rt 10.3 min.

INTERMEDIATE 79

{2-[3-Chloro-5-(cyclopentyl-(2-[1,2,4]triazol-1-yl-ethyl)-carbamoyl)-phenoxy]-ethyl}-pyridin-4-yl-carbamic acid tert-butyl ester A solution of 3-[2-(tert-butoxycarbonyl-pyridin-4-yl-amino)-ethoxy]-5-chloro-benzoic acid (0.040 g), cyclopentyl-(2-[1,2,4]triazol-1-yl-ethyl)-amine (0.05 g) and EEDQ (0.040 g) in acetonitrile (2 ml) was stirred at reflux, under nitrogen, for 2 h. The solvent was evaporated and the residue was purified by flash chromatography eluting with dichloromethane:methanol (95:5 v/v) to give the title compound as a yellow oil (0.022 g).

Mass spectrum: Found: MH$^+$ 555.

INTERMEDIATE 80

{2-[3-Chloro-5-(cyclopentyl-(4-[1,2,4]triazol-1-yl-butyl)-carbamoyl)-phenoxy]-ethyl}-pyridin-4-yl-carbamic acid tert-butyl ester A solution of 3-[2-(tert-butoxycarbonyl-pyridin-4-yl-amino)-ethoxy]-5-chloro-benzoic acid (0.040 g), cyclopentyl-(4-[1,2,4]triazol-1-yl-butyl)-amine (0.055 g) and EEDQ (0.050 g) in acetonitrile (2 ml) was stirred at reflux, under nitrogen, for 4 h. The solvent was evaporated and the residue was purified by flash chromatography eluting with dichloromethane:methanol:ammonia (95:5:0.5 then 90:10:1 v/v/v) to give the title compound as an orange oil (0.022 g).

Mass spectrum: Found: MH$^+$ 583 ($^{35}$Cl).

INTERMEDIATE 81

{2-[3-Chloro-5-(3-fluorophenyl-(3-tetrazol-2-yl-propyl)-carbamoyl)-phenoxy]-ethyl}-pyridin-4-yl-carbamic acid tert-butyl ester 2M Oxalyl chloride solution in dichloromethane (0.11 ml) and dry DMF (0.002 ml) were added to a stirred suspension of 3-[2-(tert-butoxycarbonyl-pyridin-4-yl-amino)-ethoxy]-5-chloro-benzoic acid (0.060 g) in dry dichloromethane (1 ml) under nitrogen. After 5 min, DIPEA (0.090 ml) was added followed after a further 40 min by 3-fluorophenyl-(3-tetrazol-2-yl-propyl)-amine (0.066 g) and DMAP (0.002 g). After 3 days the solvent was evaporated and the residue was purified by flash chromatography eluting with dichloromethane:methanol (98:2 v/v) to give the title compound as a green foam (0.079 g).

Mass spectrum: Found: MH$^+$ 596 ($^{35}$Cl).

INTERMEDIATE 82

{2-[3-Chloro-5-(2-fluorophenyl-(3-tetrazol-2-yl-propyl)-carbamoyl)-phenoxy]-ethyl}-pyridin-4-yl-carbamic acid tert-butyl ester 2M Oxalyl chloride solution in dichloromethane (0.110 ml) and dry DMF (0.002 ml) were added to a stirred suspension of 3-[2-(tert-butoxycarbonyl-pyridin-4-yl-amino)-ethoxy]-5-chloro-benzoic acid (0.060 g) in dry dichloromethane (1 ml) under nitrogen. After 5 min DIPEA (0.090 ml) was added followed after a further 40 min by 2-fluorophenyl-(3-tetrazol-2-yl-propyl)-amine (0.066 g) and DMAP (0.002 g). After 40 h the solvent was evaporated and the residue was purified by flash chromatography, eluting with dichloromethane:methanol (98:2 v/v) to give the title compound as a viscous yellow oil (0.059 g).

Mass spectrum: Found: MH$^+$ 596 ($^{35}$Cl).

INTERMEDIATE 83

{2-[3-Chloro-5-(phenyl-(3-tetrazol-2-yl-propyl)-carbamoyl)-phenoxy]ethyl}-pyridin-4-yl-carbamic acid tert-butyl ester 2M Oxalyl chloride solution in dichloromethane (0.11 ml), and dry DMF (0.005 ml) were added to a stirred suspension of 3-[2-(tert-butoxycarbonyl-pyridin-4-yl-amino)-ethoxy]-5-chloro-benzoic acid (0.067 g) in dry dichloromethane (1 ml) under nitrogen. After 10 min, DIPEA (0.100 ml) was added followed after a further 40 min by phenyl-(3-tetrazol-2-yl-propyl)-amine (0.033 g) and DMAP (0.004 g). After 7 days the solvent was evaporated and the residue was purified by flash chromatography, eluting with dichloromethane:methanol (98:2 v/v) to give the title compound as a pale yellow oil (0.024 g).

Mass spectrum: Found: MH$^+$ 564 ($^{35}$Cl).

INTERMEDIATE 84

{2-[3-Chloro-5-(phenyl-(3-[1,2,3]-triazol-2-yl-propyl)-carbamoyl)-phenoxy]-ethyl}-pyridin-4-yl-carbamic acid tert-butyl ester 2M Oxalyl chloride solution in dichloromethane (0.25 ml) and dry DMF (0.010 ml) were added to a stirred suspension of 3-[2-tert-butoxycarbonyl-pyridin-4-yl-amino)-ethoxy]-5-chloro-benzoic acid (0.161 g) in dry dichloromethane (2 ml) under nitrogen. After 10 min. DIPEA (0.25 ml) was added followed after a further 40 min by phenyl-(3-[1,2,3]-triazol-2-yl-propyl)-amine (0.077 g) and DMAP (0.012 g). After 7 days the solvent was evaporated and the residue was purified by flash chromatography, eluting with dichloromethane:methanol (96:4 v/v) to give the title compound as a yellow oil (0.083 g).

Mass spectrum: Found: MH$^+$ 563 ($^{35}$Cl).

INTERMEDIATE 85

{2-[3-Chloro-5-(phenyl-2-(pyridin-2-yloxy)-ethyl-carbamoyl)-phenoxy]-ethyl}-pyridin-4-yl-carbamic acid tert-butyl ester 2M Oxalyl chloride in dichloromethane (0.16 ml) and dry DMF (0.008 ml) were added to a stirred suspension of 3-[2-(tert-butoxycarbonyl-pyridin-4-yl-amino)-ethoxy]-5-chloro-benzoic acid (0.115 g) in dry dichloromethane (1.5 ml) under nitrogen. After 10 min, DIPEA (0.18 ml) was added followed after a further 40 min by phenyl-2-(pyridin-2-yloxy)-ethylamine (0.059 g) and DMAP (0.008 g). After 7 days the solvent was evaporated and the residue was purified by flash chromatography, eluting with dichloromethane:methanol (98:2 v/v), to give the title compound as a pale yellow oil (0.065 g).

Mass spectrum: Found: MH$^+$ 589 ($^{35}$Cl).

INTERMEDIATE 86

{2-[3-Chloro-5-(isopropyl-2-methoxy-ethyl-carbamoyl)-phenoxy]-ethyl}-pyridin-4-yl-carbamic acid tert-butyl ester A solution of 3-[2-(tert-butoxycarbonyl-pyridin-4-yl-amino)-ethoxy]-5-chloro-benzoic acid (0.100 g) isopropyl-2-methoxy-ethylamine (0.140 g) and EEDQ (0.130 g) in acetonitrile (2 ml) was stirred at 50° C., under nitrogen, for 18 h. The solvent was evaporated and the residue was partitioned between water and ethyl acetate. The organic layer was washed with water and brine, dried (Na$_2$SO$_4$) and concentrated to an orange oil which was purified by flash chromatography, eluting with dichloromethane:methanol (98:2 then 96:4 v/v) to give the title compound as a pale yellow oil (0.065 g).

Mass spectrum: Found: MH$^+$ 492 ($^{35}$Cl).

INTERMEDIATE 87

{2-[3-Chloro-5-isopropyl-methyl-carbamoyl)-phenoxy]-ethyl}-pyridin-4-yl-carbamic acid tert-butyl ester To a stirred solution of 3-[2-(tert-butoxycarbonyl-pyridin-4-yl-amino)-ethoxy]-5-chloro-benzoic acid (0.071 g), TBTU (0.064 g), and HOBt (0.03 g) in DMF (1 ml) was added N-isopropylmethylamine (0.095 ml) after 25 min. The reaction mixture was stirred at room temperature for 2 days then the solvent was removed by evaporation at reduced pressure and the residue partitioned between ethyl acetate and water The combined organic layers were washed with saturated brine and dried over magnesium sulphate. After concentration, the crude product was purified by flash chromatography eluting with ethyl acetate. Evaporation of the required fraction at reduced pressure gave the title compound as a pale yellow gum (0.065 g).

Hplc system 3 ($\lambda$=220–330 nm) Rt 4.2 min.

INTERMEDIATE 88

{2-[3-Chloro-5-(isopropyl-2-(pyridin-2-yloxy)-ethyl-carbamoyl)-phenoxy]ethyl}-pyridin-4-yl-carbamic acid tert-butyl ester A solution of 3-[2-(tert-butoxycarbonyl-pyridin-4-yl-amino)-ethoxy]-5-chloro-benzoic acid (0.10 g) isopropyl-2-(pyridin-2-yloxy)-ethylamine (0.18 g) and EEDQ (0.136 g) in acetonitrile (2 ml) was stirred at reflux, under nitrogen, for 18 h. The solvent was evaporated and the residue was purified by flash chromatography on silica eluting with dichloromethane/methanol (98:2 then 96:4) to give the title compound as a pale yellow oil (0.033 g).

Mass spectrum: Found: MH$^+$ 555 ($^{35}$Cl).

INTERMEDIATE 89

{2-[3-Chloro-5-(diisopropylcarbamoyl)-phenoxy]-ethyl}-pyridin-4-yl-carbamic acid tert-butyl ester To a suspension of 3-[2-(tert-butoxycarbonyl-pyridin-4-yl-amino)-ethoxy]-5-chloro-benzoic acid (0.10 g) in tetrahydrofuran (5 ml) was added DMF (0.005 ml) and oxalyl chloride (0.175 ml). After 0.5 h DIPEA (0.13 ml), diisopropylamine (0.20 ml) and DMAP (0.002 g) were added. After 18 h the mixture was partitioned between ethyl acetate and saturated aqueous sodium bicarbonate solution. The combined organic phases were washed with brine and dried over magnesium sulphate. Filtration and evaporation gave the crude product which was purified by flash column chromatography on silica eluting with cyclohexane/ethyl acetate (1:3). This afforded the title compound as a colourless gum (0.078 g).

Mass spectrum: Found: MH$^+$ 476.2304 C$_{25}$H$_{35}$$^{35}$ClN$_3$O$_4$ requires 476.2316.

INTERMEDIATE 90

3-[2-(Benzyloxycarbonyl-pyridin-4-yl-amino)-ethoxy]-5-chloro-benzoic acid methyl ester A solution of 3-[2-(tert-butoxycarbonyl-pyridin-4-yl-amino)-ethoxy]-5-chloro-benzoic acid methyl ester (0.950 g) in dichloromethane (16 ml) and trifluoroacetic acid (4 ml) was stored at room temperature for 1 h. The solution was concentrated in vacuo and residual trifluoroacetic acid removed by co-evaporation with further dichloromethane. The residue was dissolved in dichloromethane (20 ml) and the solution stirred with saturated aqueous sodium bicarbonate (25 ml). Benzyl chloroformate (0.394 ml) was added to the bi-phasic mixture and stirring continued for 20 h. The aqueous layer was removed and the organic layer washed with 1M aqueous hydrochloric acid, saturated aqueous sodium bicarbonate, water and dried with brine and over sodium sulphate and concentrated under reduced pressure.

The residue was purified by flash column chromatography, eluting with ethyl acetate:petroleum ether (3:1 v/v), to give the title compound as a colourless gum (0.32 g).

Hplc system 1 ($\lambda$=254 nm) Rt 10.6 min.

INTERMEDIATE 91

3-[2-Benzyloxycarbonyl-pyridin-4-yl-amino)-ethoxy]-5-chloro-benzoic acid

To a stirred solution of 3-[2-(benzyloxycarbonyl-pyridin-4-yl-amino)-ethoxy]-5-chloro-benzoic acid methyl ester (0.32 g) in a mixture of 1,4-dioxane (10 ml) and water (5 ml) was added 2M sodium hydroxide solution (0.72 ml). The reaction mixture was stirred at room temperature for 20 h, neutralised by the addition of 2M hydrochloric acid (0.72 ml) and then concentrated under reduced pressure. The residue was triturated with water and then dissolved in a mixture of ethyl acetate, chloroform, tetrahydrofuran and methanol until all the gum had dissolved. The solution was dried over sodium sulphate and then concentrated under reduced pressure gave the title compound as a white solid (0.27 g).

Hplc system 1 ($\lambda$=254 nm) Rt 8.1 min.

INTERMEDIATE 92

3-({3-[2-Benzyloxycarbonyl-pyridin-4-yl-amino)-ethoxy]-5-chloro-benzoyl}-tert-butyl-amino)-propionic acid methyl ester To a stirred suspension of 3-[2-(benzyloxycarbonyl-pyridin-4-yl-amino)-ethoxy]-5-chloro-benzoic acid (0.265 g) and DMF (0.010 ml) in anhydrous dichloromethane (15 ml) was added a 2M solution of oxalyl chloride in dichloromethane (0.434 ml). After 1 h a mixture of 3-(tert-butylamino)-propionic acid methyl ester (0.987 g), DIPEA (0.324 ml) and DMAP (0.008 g) in dichloromethane (5 ml) was added and the reaction stirred at room temperature for 18 h. The reaction mixture was diluted with chloroform:dichloromethane (1:1 v/v, 50 ml) and extracted with 2M aqueous sodium hydroxide, 2M aqueous hydrochloric acid, saturated aqueous sodium bicarbonate and dried with brine and over sodium sulphate. The solvent was evaporated under reduced pressure and the residue purified by flash column chromatography, eluting with ethyl acetate:petroleum ether (2:1 and 3:1 v/v) to give the title compound as a colourless gum (0.038 g).

Hplc system 1 ($\lambda$254 nm) Rt 10.5 min.

INTERMEDIATE 93

3-({3-[2-(Benzyloxycarbonyl-pyridin-4-yl-amino)-ethoxy]-5-chloro-benzoyl}-tert-butyl-amino)-propionic acid To a stirred solution of 3-({3-[2-(benzyloxycarbonyl-pyridin-yl-amino)-ethoxy]-5-chloro-benzoyl}-tert-butyl-amino)-propionic acid methyl ester (0.038 g) in a mixture of 1,4-dioxane (1 ml) and water (0.5 ml) was added 2M sodium hydroxide solution (0.066 ml). The reaction mixture was stirred at room temperature for 1 h, neutralised by the addition of 2M hydrochloric acid (0.066 ml) and then concentrated under reduced pressure. The residue was partitioned between ethyl acetate and brine, the aqueous layer was removed and the organic layer was dried over sodium sulphate and then concentrated under reduced pressure gave the title compound as a white solid (0.034 g).

Hplc system 1 (λ=254 nm) Rt 8.5 min.

INTERMEDIATE 94

(2-{3-[tert-Butyl-(2-tert-butylcarbamoyl-ethyl)-carbamoyl]-5-chloro-phenoxy}-ethyl)-pyridin-4-yl-carbamic acid benzyl ester A solution of 3-({3-[2-benzyloxycarbonyl-pyridin-yl-amino)-ethoxy]-5-chloro-benzoyl}-tert-butyl-amino)-propionic acid (0.034 g), HATU® (0.046 g) and DIPEA (0.020 ml) was stirred for 20 min then tert-butylamine (0.063 ml) was added. After 14 h the solvent was removed in vacuo and the residue partitioned between ethyl acetate and water. The aqueous layer was removed and the organic layer washed with further water, 1M aqueous hydrochloric acid, saturated aqueous sodium bicarbonate, water and dried with brine and over sodium sulphate. The solvent was removed to give the title compound as a colourless gum (0.024 g).

Hplc system 1 (λ=254 nm) Rt 8.5 min.

INTERMEDIATE 95

3-({3-[2-(tert-Butoxycarbonyl-pyridin-4-yl-amino)-ethoxy]-5-chloro-benzoyl}-cyclobutyl-amino)-propionic acid methyl ester compound To a stirred solution of 3-[2-(tert-butoxycarbonyl-pyridin-4-yl-amino)-ethoxy]-5-chloro-benzoic acid (0.196 g) and TBTU (0.321 g) in DMF (5 ml) was added DIPEA (0.1 74 ml) followed by 3-(cyclobutyl-amino)-propionic acid methyl ester (0.314 g) after 10 min. The reaction mixture was stirred at room temperature for 68 h and then concentrated under reduced pressure. The residue was partitioned between ethyl acetate and water. The aqueous layer was removed and the organic layer washed with further water, saturated aqueous sodium bicarbonate, 1M aqueous hydrochloric acid, saturated aqueous sodium bicarbonate and water. The organic layer was dried with brine and over sodium sulphat. The solvent was removed under reduced pressure and the residue purified by flash column chromatography, eluting with ethyl acetate:petroleum ether (2:1 v/v), to give the title compound (0.096 g) as a colourless gum.

Mass spectrum: Found: MH$^+$ 532 ($^{35}$Cl).

INTERMEDIATE 96

3-({3-[2-tert-Butoxycarbonyl-pyridin-4-yl-amino)-ethoxy]-5-chloro-benzoyl}-cyclobutyl-amino)-propionic acid To a stirred solution of 3-({3-[2-(tert-butoxycarbonyl-pyridin-4-yl-amino)-ethoxy]-5-chloro-benzoyl}-cyclobutyl-amino)-propionic acid methyl ester (0.096 g) in a mixture of 1,4-dioxane (2 ml) and water (1 ml) was added 2M sodium hydroxide solution (0.180 ml). The reaction mixture was stirred at room temperature for 2 h, neutralised by the addition of 2M hydrochloric acid (0.180 ml) and then concentrated under reduced pressure. The residue was partitioned between ethyl acetate and water, the aqueous layer removed and the organic layer extracted with 0.2M sodium hydroxide. The aqueous layer was acidified with an equivalent volume of 0.2M hydrochloric acid, and extracted with ethyl acetate. This solution was dried over sodium sulphate and then concentrated under reduced pressure gave the title compound as a colourless gum (0.050 g).

Hplc system 1 (λ=8.2 nm) Rt 8.2 min.

INTERMEDIATE 97

(2-{3-[(2-tert-Butylcarbamoyl-ethyl)-cyclobutylcarbamoyl]-5-chloro-phenoxy}-ethyl)-pyridin-4-yl-carbamic acid tert-butyl ester To a stirred solution of ({3-[2-(tert-butoxycarbonyl-pyridin-4-yl-amino)-ethoxy]-5-chloro-benzoyl}-cyclobutyl-amino)-propionic acid (0.025 g) and HATU® (0.038 g) in DMF (1 ml) was added DIPEA (0.017 ml) followed by tert-butylamine (0.053 ml) after 10 min. The reaction mixture was stirred at room temperature for 18 h and then concentrated under reduced pressure. The residue was subjected to preparative hplc and the title compound (0.021 g) was obtained as a colourless gum by concentration of the required fraction under reduced pressure and drying by repetitive addition of acetonitrile and concentration under reduced pressure.

Mass spectrum: Found: MH$^+$ 573 ($^{35}$Cl).

INTERMEDIATE 98

[2-(3-Chloro-5-{cyclobutyl-[2-(2,2-dimethyl-propylcarbamoyl)-ethyl]-carbamoyl}-phenoxy)-ethyl]-pyridin-4-yl-carbamic acid tert-butyl ester To a stirred solution of ({3-[2-(tert-butoxycarbonyl-pyridin-4-yl-amino)-ethoxy]-5-chloro-benzoyl}-cyclobutyl-amino)-propionic acid (0.025 g) and HATU® (0.038 g) in DMF (1 ml) was added DIPEA (0.017 ml) followed by neopentylamine (0.053 ml) after 10 min. The reaction mixture was stirred at room temperature for 18 h and then concentrated under reduced pressure. The residue was subjected to preparative hplc and the title compound (0.016 g) was obtained as a colourless gum by concentration of the required fraction under reduced pressure and drying by repetitive addition of acetonitrile and concentration under reduced pressure.

Mass spectrum: Found: MH$^+$ 587 ($^{35}$Cl).

INTERMEDIATE 99

(2-{3-Chloro-5-[(2-cyano-ethyl)-cyclobutyl-carbamoyl]-phenoxy}-ethyl)-pyridin-4-yl-carbamic acid tert-butyl ester To a stirred solution of 3-[2-(tert-butoxycarbonyl-pyridin-4-yl-amino)-ethoxy]-5-chloro-benzoic acid (0.030 g) and HATU® (0.058 g) in DMF (0.4 ml) was added DIPEA (0.040 ml) followed by a solution of 3-(cyclobutylamino) propionitrile (0.038 g) in DMF (0.6 ml) after 10 min. The reaction mixture was stirred at room temperature for 18 h and then concentrated under reduced pressure. The residue was subjected to preparative hplc and the title compound (0.042 g) was obtained as a colourless gum by concentration of the required fraction under reduced pressure and drying by repetitive addition of acetonitrile and concentration under reduced pressure.

Mass spectrum: Found: MH$^+$ 499 ($^{35}$Cl).

INTERMEDIATE 100

(2-{3-Chloro-5-[isopropyl-(2-sulfamoyl-ethyl)-carbamoyl]-phenoxy}-ethyl)-pyridin-4-yl-carbamic acid tert-butyl ester To a stirred solution of 3-[2-(tert-butoxycarbonyl-pyridin-4-yl-amino)-ethoxy]-5-chloro-benzoic acid (0.030 g) and HATU® (0.058 g) in DMF (0.4 ml) was added DIPEA (0.040 ml) followed by a solution of 2-isopropylamino-ethanesulfonic acid amide (0.058 g) in DMF (0.6 ml) after 10 min. The reaction mixture was stirred at room temperature for 18 h and then concentrated under reduced pressure. The residue was subjected to preparative hplc and the title compound (0.012 g) was obtained as a colourless gum by concentration of the required fraction under reduced pressure and drying by repetitive addition of acetonitrile and concentration under reduced pressure.

Mass spectrum: Found: MH$^+$ 541 ($^{35}$Cl).

INTERMEDIATE 101

[2-(3-Chloro-5-{[2-(2,2-dimethyl-propylsulfamoyl)-ethyl]-isopropyl-carbamoyl}-phenoxy)ethyl]-pyridin-4-yl-carbamic acid tert-butyl ester To a stirred solution of 3-[2-(tert-butoxycarbonyl-pyridin-4-yl-amino)-ethoxy]-5-chloro-benzoic acid (0.030 g) and HATU® (0.058 g) in DMF (0.4 ml) was added DIPEA (0.040 ml) followed by a solution of 2-isopropylamino-ethanesulfonic acid (2,2-dimethyl-propyl)-amide (0.070 g) in DMF (0.6 ml) after 10 min. The reaction mixture was stirred at room temperature for 18 h and then concentrated under reduced pressure. The residue was subjected to preparative hplc and the title compound (0.042 g) was obtained as a colourless gum by concentration of the required fraction under reduced pressure and drying by repetitive addition of acetonitrile and concentration under reduced pressure.

Mass spectrum: Found: MH$^+$ 611 ($^{35}$Cl).

INTERMEDIATE 102

3-Chloro-N{2-(5-hydroxy-[1,2,4]oxadiazol-3-yl)-ethyl}-N-isopropyl-5-[2[(pyridin-4-ylamino)-ethoxy]-benzamide carbamic acid tert-butyl ester To a stirred solution of 3-[2-(tert-butoxycarbonyl-pyridin-4-yl-amino)-ethoxy]-5-chloro-benzoic acid (0.100 g), TBTU (0.164 g) in DMF (3 ml) was added DIPEA (0.174 ml) followed by (3-(2-isopropylamino-ethyl)-5-hydroxy-[1,2,4]oxadiaxole trifluoroacetate (0.043 g) after 15 min. The reaction mixture was stirred at room temperature for 18 h and then concentrated under reduced pressure and the residue subjected to preparative hplc to give the title compound (0.046 g) as a colourless oil.

Mass spectrum: Found: MH$^+$ 546 ($^{35}$Cl).

INTERMEDIATE 103

{2-[3-Chloro-5-(isopropyl-(2-(4-tert-butylphenyl)-ethyl-carbamoyl)-phenoxy]-ethyl}pyridin-4-yl-carbamic acid tert-butyl ester A solution of 3-[2-(tert-butoxycarbonyl-pyridin-4-yl-amino)-ethoxy]-5-chloro-benzoic acid (0.100 g), isopropyl-2-(4-tert-butylphenyl)-ethylamine (0.170 g) and EEDQ (0.136 g) in acetonitrile (2 ml) was stirred at reflux, under nitrogen, for 6 h. The solvent was evaporated and the residue was purified by flash chromatography, eluting with dichloromethane:methanol (98:2 v/v), to give the title compound as a pale yellow oil (0.063 g).

Mass Spectrum: Found: MH$^+$ 594 ($^{35}$Cl).

EXAMPLE 1

N-Cyclohexyl-3, N-dimethyl-5-[2-(pyridin-4-ylamino)-ethoxy]-benzamide trifluoroacetate salt A stirred solution of 3-methyl-5-[2-(pyridin-4-ylamino)-ethoxy]-benzoic acid trifluoroacetate salt (0.031 g) in DMF (1 ml) was treated with HOBt (0.011 g), DIPEA (0.028 ml), N-methylcyclohexylamine (0.010 ml), and TBTU (0.026 g). The resulting solution was retained in a sealed flask for 64 h. The reaction mixture was concentrated under reduced pressure and the resulting gum subjected to preparative hplc. The required fraction was concentrated and then dried by addition of methanol and concentration under reduced pressure, addition of toluene and again concentration under reduced pressure giving the title compound as a colourless gum (0.034 g).

Hplc system 2 ($\lambda$=254 nm) Rt 11.6 min; Mass spectrum: Found: MH$^+$ 368.2336 C$_{22}$H$_{30}$N$_3$O$_2$ requires 368.2338.

EXAMPLE 2

3-Bromo-N-cyclohexyl-N-methyl-5-[2-(pyridin-4-ylamino)-ethoxy]-benzamide trifluoroacetate salt To a stirred solution of 3-bromo-5[-2-(pyridin-4-ylamino)-ethoxy]-benzoic acid trifluoroacetate salt (0.034 g), TBTU (0.048 g) and HOBt (0.014 g) in DMF (0.3 ml) was added DIPEA (0.026 ml) followed by N-methylcyclohexylamine (0.020 ml) after 15 min. The reaction mixture was stirred at room temperature for 18 h and then concentrated under reduced pressure. The residue was subjected to preparative hplc and the title compound (0.005 g) was obtained as a colourless gum by concentration of the required fraction under reduced pressure and drying by repetitive addition of acetonitrile and concentration under reduced pressure.

Hplc system 2 ($\lambda$=254 nm) Rt 12.0 min; Mass spectrum: Found: MH$^+$ 432 ($^{79}$Br).

EXAMPLE 3

N-Allyl-3-bromo-N-cyclohexyl-5-[2-(pyridin-4-ylamino)-ethoxy]-benzamide trifluoroacetate salt To a stirred solution of 3-bromo-5-[2-(pyridin-4-ylamino)-ethoxyl-benzoic acid trifluoroacetate salt (0.034 g), TBTU (0.048 g) and HOBt (0.0149) in DMF (0.3 ml) was added DIPEA (0.026 ml) followed by N-allylcyclohexylamine (0.022 ml) after 15 min. The reaction mixture was stirred at room temperature for 18 h and then concentrated under reduced pressure. The residue was subjected to preparative hplc and the title compound (0.011 g) was obtained as a colourless gum by concentration of the required fraction under reduced pressure and drying by repetitive addition of acetonitrile and concentration under reduced pressure.

Hplc system 2 ($\lambda$=254 nm) Rt 12.8 min; Mass spectrum: Found: MH$^+$ C$_{23}$H$_{29}$$^{79}$Br$_1$N$_3$O$_2$ requires 458.1443.

EXAMPLE 4

N-Allyl-3-bromo-N-cyclopentyl-5-[2-(pyridin-4-ylamino)-ethoxy]-benzamide trifluoroacetate salt To a stirred solution of 3-bromo-5-[2-(pyridin-4-ylamino)-ethoxy]-benzoic acid trifluoroacetate salt (0.034 g), TBTU (0.048 g) and HOBt (0.014 g) in DMF (0.3 ml) was added DIPEA (0.026 ml) followed by N-allylcyclopentyamine (0.022 ml) after 15 min. The reaction mixture was stirred at room temperature for 18 h and then concentrated under reduced pressure. The residue was subjected to preparative hplc and the title compound (0.022 g) was obtained as a colourless gum by concentration of the required fraction under reduced pressure and drying by repetitive addition of acetonitrile and concentration under reduced pressure.

Hplc system 2 (λ=254 nm) Rt 12.4 min; Mass spectrum: Found: MH$^+$ C$_{22}$H$_{27}$$^{79}$Br$_1$N$_3$O$_2$ requires 444.1287.

EXAMPLE 5

3-Chloro-N-cyclohexyl-N-methyl-5-[2-(pyridin-4-ylamino)-ethoxy]-benzamide trifluoroacetate salt A solution of {2-[3-chloro-5-(cyclohexyl-methyl-carbamoyl)-phenoxy]-ethyl}-pyridin-4-yl-carbamic acid tert-butyl ester (0.036 g) in a mixture of dichloromethane (1 ml) and trifluoroacetic acid (1 ml) was stored at room temperature for 2 h and then concentrated under reduced pressure. The residue was subjected to preparative hplc and the title compound (0.024 g) was obtained as a colourless gum by concentration of the required fraction under reduced pressure and drying by repetitive addition of acetonitrile and concentration under reduced pressure.

Hplc system 1 (λ=254 nm) Rt 8.1 min; Mass spectrum: Found: MH$^+$ C$_{21}$H$_{27}$$^{35}$Cl$_1$N$_3$O$_2$ requires 388.1792.

EXAMPLE 6

N-Allyl-3-chloro-N-cyclopentyl-5-[2-(pyridin-4-ylamino)-ethoxy]-benzamide trifluoroacetate salt A solution of {2-[3-(allyl-cyclopentyl-carbamoyl)-5-chloro-phenoxy]-ethyl}-pyridin-4-yl-carbamic acid tert-butyl ester (0.030 g) in a mixture of dichloromethane (1 ml) and trifluoroacetic acid (1 ml) was stored at room temperature for 2 h and then concentrated under reduced pressure The residue was subjected to preparative hplc and the title compound (0.026 g) was obtained as a colourless gum by concentration of the required fraction under reduced pressure and drying by repetitive addition of acetonitrile and concentration under reduced pressure.

Hplc system 1 (λ=254 nm) Rt 8.7 min; Mass spectrum: Found: MH$^+$ 400 ($^{35}$Cl).

EXAMPLE 7

N-Allyl-3-chloro-N-cyclopentyl-5-[2-(pyridin-4-ylamino)-ethoxy]-benzamide trifluoroacetate salt A solution of {2-[3-(allyl-cyclohexyl-carbamoyl)-5-chloro-phenoxy]-ethyl}-pyridin-4-yl-carbamic acid tert-butyl ester (0.032 g) in a mixture of dichloromethane (1 ml) and trifluoroacetic acid (1 ml) was stored at room temperature for 2 h and then concentrated under reduced pressure. The residue was subjected to preparative hplc and the title compound (0.027 g) was obtained as a colourless gum by concentration of the required fraction under reduced pressure and drying by repetitive addition of acetonitrile and concentration under reduced pressure.

Hplc system 1 (λ=254 nm) Rt 9.3 min; Mass spectrum: Found: MH$^+$ 414.1960 C$_{23}$H$_{29}$$^{35}$Cl$_1$N$_3$O$_2$ requires 414.1962.

EXAMPLE 8

3-Chloro-N-cyclohexyl-N-propyl-5-[2-(pyridin-4-ylamino)-ethoxy]-benzamide trifluoroacetate salt A solution of {2-[3-(propyl-cyclopentyl-carbamoyl)-5-chloro-phenoxy]-ethyl}-pyridin-4-yl-carbamic acid tert-butyl ester (0.07 g) in a mixture of dichloromethane (2 ml) and trifluoroacetic acid (2 ml) was stored at room temperature for 1 h and then concentrated under reduced pressure. The residue was subjected to preparative hplc and the title compound (0.036 g) was obtained as a colourless gum by concentration of the required fraction under reduced pressure and drying by repetitive addition of acetonitrile and concentration under reduced pressure.

Hplc system 1 (λ=254 nm) Rt 9.2 min; Mass spectrum: Found: MH$^+$ 402.1952 C$_{22}$H$_{28}$$^{35}$Cl$_1$N$_3$O$_2$ requires 402.1948.

EXAMPLE 9

3-Chloro-N-cyclopentyl-N-(3-hydroxy-propyl)-5-[2-(pyridin-4-ylamino)-ethoxy]-benzamide trifluoroacetate A solution of (2-{3-chloro-5-[cyclopentyl-(3-hydroxy-propyl)-carbamoyl]-phenoxy}-ethyl)-pyridin-4-yl-carbamic acid tertbutyl ester (0.07 g) in a mixture of dichloromethane (2 ml) and trifluoroacetic acid (2 ml) was stored at room temperature for 1 h and then concentrated under reduced pressure. The residue was subjected to preparative hplc and the title compound (0.011 g) was obtained as a colourless gum by concentration of the required fraction under reduced pressure and drying by repetitive addition of acetonitrile and concentration under reduced pressure.

Hplc system 1 (λ=254 nm) Rt 6.9 min; Mass spectrum: Found: MH$^+$ 418 ($^{35}$Cl).

EXAMPLE 10

3-Chloro-N-propyl-5-[2-(pyridin-4-ylamino)-ethoxy]-N-(tetrahydro-pyran-4-yl)-benzamide trifluoroacetate A solution of (2-{3-chloro-5-[propyl-(tetrahydro-pyran-4-yl)-carbamoyl]-phenoxy}-ethyl)-pyridin-4-yl-carbamic acid tert-butyl ester (0.070 g) in a mixture of dichloromethane (2 ml) and trifluoroacetic acid (2 ml) was stored at room temperature for 2 h and then concentrated under reduced pressure. The residue was subjected to preparative hplc and the title compound (0.048 g) was obtained as a colourless gum by concentration of the required fraction under reduced pressure and drying by repetitive addition of acetonitrile and concentration under reduced pressure.

Hplc system 1 (λ=254 nm) Rt 6.9 min; Mass spectrum: Found: MH$^+$ 418.1882 C$_{22}$H$_{29}$$^{35}$Cl$_1$N$_3$O$_3$ requires 418.1897.

EXAMPLE 11

({3-Chloro-5-[2-(pyridin-4-ylamino)-ethoxy]-benzoyl}-cyclopentyl-amino)-acetic acid To a solution of {2-[3-(allyl-cyclopentyl-carbamoyl)-5-chloro-phenoxy]-ethyl}-pyridin-4-yl-carbamic acid tert-butyl ester (0.06 g) in tert-butanol (3.2 ml) was added a solution of potassium permanganate (0.006 g), sodium periodate (0.157 g) and sodium bicarbonate (0.051 g) in water (3.2 ml). The purple reaction mixture was stirred at room temperature for 1.5 h and then added to ethanol (25 ml) the precipitate was filtered and the filtrate evaporated in vacuo. The residue was dissolved in a mixture of dichloromethane (5 ml) and trifluoroacetic acid (5 ml) was stored at room temperature for 17 h and then concentrated under reduced pressure. The residue was subjected to preparative hplc and the title compound (0.021 g) was obtained as a colourless gum by concentration of the required fraction under reduced pressure.

Hplc system 1 (λ=254 nm) Rt 6.7 min; Mass spectrum: Found: MH$^+$ 418.1548 C$_{21}$H$_{25}$$^{35}$Cl$_1$N$_3$O$_4$ requires 418.1534.

EXAMPLE 12

3-Chloro-N-cyclopentyl-N-(2,3-dihydroxy-propyl)-5-[2-(pyridin-4-ylamino)-ethoxy]-benzamide trifluoroacetate A solution of crude (2-{3-chloro-5-[cyclopentyl-(2,3-dihydroxy-propyl)-carbamoyl]-phenoxy}-ethyl)-pyridin-4-yl-carbamic acid tert-butyl ester (0.044 g) in a mixture of dichloromethane (1 ml) and trifluoroacetic acid (1 ml) was stored at room temperature for 1 h and then concentrated under reduced pressure. The residue was subjected to preparative hplc and the title compound (0.007 g) was obtained as a colourless gum by concentration of the required fraction under reduced pressure and drying by repetitive addition of acetonitrile and concentration under reduced pressure.

Hplc system 1 ($\lambda$=254 nm) Rt 6.2 min; Mass spectrum: Found: $MH^+$ 434.1862 $C_{22}H_{29}{}^{35}Cl_1N_3O_4$ requires 434.1847.

EXAMPLE 13

3-Chloro-N-cyclopentyl-N-(3-morpholin-4-yl-propyl)-5-[2-(pyridin-4-ylamino)-ethoxy]-benzamide bis(trifluoroacetate)

A solution of (2-{3-chloro-5-[cyclopentyl-(3-morpholin-4-yl-propyl)-carbamoyl]-phenoxy}-ethyl)-pyridin-4-yl-carbamic acid tert-butyl ester trifluoroacetate (0.060 g) in a mixture of dichloromethane (1 ml) and trifluoroacetic acid (1 ml) was stored at room temperature for 2 h and then concentrated under reduced pressure. The residue was subjected to preparative hplc and the title compound (0.034 g) was obtained as a colourless gum by concentration of the required fraction under reduced pressure and drying by repetitive addition of acetonitrile and concentration under reduced pressure.

Hplc system 1 ($\lambda$=254 nm) Rt 6.4 min; Mass spectrum: Found: $MH^+$ 487.2472 $C_{26}H_{36}{}^{35}Cl_1N_4O_3$ requires 487.2476.

EXAMPLE 14

3-Chloro-N-cyclopentyl-5-[2-(pyridin-4-ylamino)-ethoxy]-N-(3-pyrrolidin-1-yl-propyl)-benzamide bis(trifluoroacetate)

A solution of (2-{3-chloro-5-[cyclopentyl-(3-pyrrolidin-1-yl-propyl)-carbamoyl]-phenoxy}-ethyl)-pyridin-4-yl-carbamic acid tert-butyl ester trifluoroacetate (0.080 g) in a mixture of dichloromethane (1 ml) and trifluoroacetic acid (1 ml) was stored at room temperature for 2 h and then concentrated under reduced pressure to give the title compound (0.075 g) as a colourless gum.

Hplc system 1 ($\lambda$=254 nm) Rt 6.6 min; Mass spectrum: Found: $MH^+$ 471.2514 $C_{26}H_{36}{}^{35}Cl_1N_4O_2$ requires 471.2527.

EXAMPLE 15

3-Chloro-5-[2-(pyridin-4-ylamino)-ethoxy]-N-(3-pyrrolidin-1-yl-propyl)-N-(tetrahydropyran-4-yl)-benzamide bis(trifluoroacetate)

To a stirred solution of 3-[2-(tert-butoxycarbonyl-pyridin-4-yl-amino)-ethoxy]-5-chloro-benzoic acid (0.059 g), TBTU (0.085 g) and HOBt (0.0209) in DMF (0.6 ml) was added DIPEA (0.052 ml) followed by N-(3-pyrrolidin-1-yl-propyl)-4-aminotetrahydropyran (0.048 g) after 20 min. The reaction mixture was stirred at room temperature for 20 h and then concentrated under reduced pressure. The residue was subjected to preparative hplc and the product (0.005 g) was obtained as a colourless gum by concentration of the required fraction under reduced pressure and drying by repetitive addition of acetonitrile and concentration under reduced pressure. A solution of this product in trifluoroacetic acid (2 ml) was stored at room temperature for 18 h and the solvent removed under reduced pressure to give the title compound (0.005 g) as a colourless gum.

Hplc system 1 ($\lambda$=254 nm) Rt 5.6 min; Mass spectrum: Found: $MH^+$ 487 ($^{35}Cl$).

EXAMPLE 16

3-Chloro-N-(3-morpholin-4-yl-propyl)-5-[2-(pyridin-4-ylamino)-ethoxy]-N-(tetrahydropyran-4-yl)-benzamide bis(trifluoroacetate)

To a stirred solution of 3-[2-(tert-butoxycarbonyl-pyridin-4-yl-amino)-ethoxy]-5-chloro-benzoic acid (0.059 g), TBTU (0.085 g) and HOBt (0.020 g) in DMF (0.6 ml) was added DIPEA (0.052 ml) followed by N-(3-morpholin-4-yl-propyl)-4-aminotetrahydropyran (0.051 g) after 20 min. The reaction mixture was stirred at room temperature for 20 h and then concentrated under reduced pressure. The residue was subjected to preparative hplc and the and the product (0.062 g) was obtained as a colourless gum by concentration of the required fraction under reduced pressure and drying by repetitive addition of acetonitrile and concentration under reduced pressure. A solution of this product in TFA (2 ml) was stored at room temperature for 18 h and the solvent removed under reduced pressure to give the title compound (0.060 g) as a colourless gum.

Hplc system 1 ($\lambda$=254 nm) Rt 4.9 min; Mass spectrum: Found: $MH^+$ 503 ($^{35}Cl$).

EXAMPLE 17

4-({3-Chloro-5-[2-(pyridin-4-ylamino)-ethoxy]-benzoyl}-cyclopentyl-amino)-butyric acid ethyl ester trifluoroacetate A solution of crude 4-({3-[2-(tert-butoxycarbonyl-pyridin-4-yl-amino)ethoxy]-5-chloro-benzoyl}-cyclopentyl-amino)-butyric acid ethyl ester (0.020 g) in a mixture of dichloromethane (1 ml) and trifluoroacetic acid (1 ml) was stored at room temperature for 2 h and then concentrated under reduced pressure. The residue was subjected to preparative hplc and the title compound (0.005 g) was obtained as a colourless gum by concentration of the required fraction under reduced pressure and drying by repetitive addition of acetonitrile and concentration under reduced pressure.

Hplc system 1 ($\lambda$=254 nm) Rt 9.1 min; Mass spectrum: Found: $MH^+$ 474.2172 $C_{25}H_{32}{}^{35}Cl_1N_3O_4$ requires 474.2160.

EXAMPLE 18

4-({3-Chloro-5-[2-(pyridin-4-ylamino)-ethoxy]-benzoyl}-cyclopentyl-amino)-butyric acid A solution of 4-({3-[2-(tert-butoxycarbonyl-pyridin-4-yl-amino)-ethoxy]-5-chloro-benzoyl}-cyclopentyl-amino)-butyric acid (0.015 g) in trifluoroacetic acid (3 ml) was stored at room temperature for 2 h and then the solvent removed under reduced pressure. The residue was purified by preparative hplc to give title compound (0.09 g) as a colourless gum.

Hplc system 3 (λ=220 nm) Rt 3.7 min; Mass spectrum: Found: MH$^+$ 446 ($^{35}$Cl).

EXAMPLE 19

N-(3-Carbamoyl-propyl)-3-chloro-N-cyclopentyl-5-[2-(pyridin-4-ylamino)-ethoxy]-benzamide trifluoroacetate A solution of (2-{3-[(3-carbamoyl-propyl)-cyclopentyl-carbamoyl]-5-chloro-phenoxy}-ethyl)-pyridin-4-yl-carbamic acid tert-butyl ester (0.040 g) in a mixture of dichloromethane (1 ml) and trifluoroacetic acid (1 ml) was stored at room temperature for 2 h and then concentrated under reduced pressure to give the title compound (0.040 g) as a colourless gum.

Hplc system 1 (λ=254 nm) Rt 6.7 min; Mass spectrum: Found: MH$^+$ 445.1989 $C_{23}H_{30}{}^{35}Cl_1N_4O_3$ requires 445.2006.

EXAMPLE 20

3-Chloro-N-cyclopentyl-N-(4-oxo-4-pyrrolidin-1-yl-butyl)-5-[2-(pyridin-4-ylamino)-ethoxy]-benzamide bis(trifluoroacetate)

A solution of (2-{3-chloro-N-cyclopentyl-N-(4-oxo-4-pyrrolidin-1-yl-butyl)-carbamoyl]-phenoxy}-ethyl)-pyridin-4-yl-carbamic acid tert-butyl ester (0.025 g) in a mixture of dichloromethane (1 ml) and trifluoroacetic acid (1 ml) was stored at room temperature for 2 h and then concentrated under reduced pressure to give the title compound (0.025 g) as a colourless gum.

Hplc system 1 (λ=254 nm) Rt 8.5 min; Mass spectrum: Found: MH$^+$ 499 ($^{35}$Cl).

EXAMPLE 21

N-(2-Carbamoyl-ethyl)-3-chloro-N-cyclopentyl-5-[2-(pyridin-4-ylamino)-ethoxy]-benzamide trifluoroacetate A solution of (2-{3-[(2-carbamoyl-ethyl)-cyclopentyl-carbamoyl]-5-chloro-phenoxy}-ethyl)-pyridin-4-yl-carbamic acid tert-butyl ester (0.074 g) in a mixture of dichloromethane (1 ml) and trifluoroacetic acid (1 ml) was stored at room temperature for 2 h and then concentrated under reduced pressure to give the title compound (0.060 g) as a colourless gum.

Hplc system 1 (λ=254 nm)=254 nm) Rt 6.2 min; Mass spectrum: Found: MH$^+$ 431.1857 $C_{22}H_{28}{}^{35}Cl_1N_4O_3$ requires 431.1830.

EXAMPLE 22

N-Carbamoylmethyl-3-chloro-N-cyclopentyl-5-[2-(pyridin-4-ylamino)-ethoxy]-benzamide trifluoroacetate A solution of (2-{3-[(2-carbamoyl-methyl)-cyclopentyl-carbamoyl]-5-chloro-phenoxy}-ethyl)-pyridin-4-yl-carbamic acid tert-butyl ester (0.064 g) in a mixture of dichloromethane (1 ml) and trifluoroacetic acid (1 ml) was stored at room temperature for 2 h and then concentrated under reduced pressure to give the title compound (0.057 g) as a colourless gum.

Hplc system 1 (λ=254 nm) Rt 6.0 min; Mass spectrum: Found: MH$^+$ 417.1703 $C_{21}H_{26}{}^{35}Cl_1N_4O_3$ requires 417.1693.

EXAMPLE 23

N-(2-Carbamoyl-ethyl)-3-chloro-N-cyclopropyl-5-[2-(pyridin-4-ylamino)-ethoxy]-benzamide hydrochloride A solution of (2-{3-chloro-5-[(2-cyano-ethyl)-cyclopropyl-carbamoyl]-phenoxy}-ethyl)-pyridin-4-yl-carbamic acid tert-butyl ester (0.075 g) in a mixture of dichloromethane (5 ml) and trifluoroacetic acid (5 ml) was stored at room temperature for 18 h and then concentrated under reduced pressure. The residue was triturated with ethereal hydrogen chloride to give the title compound (0.065 g) as a colourless gum.

Hplc system 1 (λ=254 nm) Rt 5.1 min; Mass spectrum: Found: MH$^+$ 417.1532 $C_{20}H_{24}{}^{35}Cl_1N_4O_3$ requires 417.1537.

EXAMPLE 24

N-(2-Carbamoyl-ethyl)-3-chloro-N-(1-propyl-butyl)-5-[2-(pyridin-4-ylamino)-ethoxy]-benzamide trifluoroacetate To a stirred solution of 3-[2-(tert-butoxycarbonyl-pyridin-4-yl-amino)-ethoxy]-5-chloro-benzoic acid (0.118 g), TBTU (0.170 g) and HOBt (0.040 g) in DMF (0.6 ml) was added DIPEA (0.104 ml) followed by N-(2-propylbutyl)-3-amino-propionamide (0.086 g) after 15 min. The reaction mixture was stirred at room temperature for 20 h and then concentrated under reduced pressure. The residue was subjected to preparative hplc and the product (0.005 g) was obtained as a colourless gum by concentration of the required fraction under reduced pressure and drying by repetitive addition of acetonitrile and concentration under reduced pressure. A solution of this product in triflouroacetic acid (2 ml) was stored at room temperature for 18 h and the solvent removed under reduced pressure to give the title compound (0.090 g) as a colourless gum.

Hplc system 1 (λ=254 nm) Rt 7.6 min; Mass spectrum: Found: MH$^+$ 461 ($^{35}$Cl).

EXAMPLE 25

3-Chloro-N,N-dipropyl-5-[2-(pyridin-4-ylamino)-ethoxy]-benzamide hydrochloride

A solution of [2-(3-chloro-5-dipropylcarbamoyl-phenoxy)-ethyl]-pyridin-4-yl-carbamic acid tert-butyl ester (0.085 g) in a mixture of dichloromethane (2 ml) and trifluoroacetic acid (2 ml) was stored at room temperature for 18 h and then concentrated under reduced pressure. The residue was triturated with ethereal hydrogen chloride to give the title compound (0.063 g) as a colourless gum.

Hplc system 1 (λ=254 nm) Rt 7.9 min; Mass spectrum: Found: MH$^+$ 376.1782 $C_{20}H_{27}{}^{35}Cl_1N_3O_2$ requires 376.1792.

EXAMPLE 26

3-Chloro-N-propyl-5-[2-(pyridin-4-ylamino)-ethoxy]-N-[1,3,4]thiadiazol-2-yl-benzamide trifluoroacetate To a stirred solution of 3-[2-(tert-butoxycarbonyl-pyridin-4-yl-amino)-ethoxy]-5-chloro-benzoic acid (0.050 g), TBTU (0.074 g) and HOBt (0.018 g) in DMF (0.9 ml) was added DIPEA (0.045 ml) followed by N-propyl-2-amino-[1,3,4]thiadiazole (0.037 g) after 15 min. The reaction mixture was stirred at room temperature for 20 h and then concentrated under reduced pressure. The residue was subjected to preparative hplc and the product (0.007 g) was obtained as a colourless gum by concentration of the required fraction under reduced pressure and drying by repetitive addition of acetonitrile and concentration under reduced pressure. A solution of this product in trifluoroacetic acid (2 ml) was stored at room temperature for 18 h and the solvent removed under reduced pressure to give the title compound (0.005 g) as a colourless gum.

Hplc system 1 ($\lambda$=254 nm) Rt 7.2 min; Mass spectrum: Found: MH$^+$ 418 ($^{35}$Cl).

EXAMPLE 27

3-Chloro-N-propyl-5-[2-(pyridin-4-ylamino)-ethoxy]-N-thiazol-2-yl-benzamide trifluoroacetate To a stirred solution of 3-[2-(tert-butoxycarbonyl-pyridin-4-yl-amino)-ethoxy]-5-chloro-benzoic acid (0.050 g), TBTU (0.074 g) and HOBt (0.018 g) in DMF (0.9 ml) was added DIPEA (0.045 ml) followed by N-propyl-2-aminothiazole (0.037 g) after 15 min. The reaction mixture was stirred at room temperature for 20 h and then concentrated under reduced pressure. The residue was subjected to preparative hplc and the product (0.022 g) was obtained as a colourless gum by concentration of the required fraction under reduced pressure and drying by repetitive addition of acetonitrile and concentration under reduced pressure. A solution of this product in trifluoroacetic acid (2 ml) was stored at room temperature for 18 h and the solvent removed under reduced pressure to give the title compound (0.019 g) as a colourless gum.

Hplc system 1 ($\lambda$=254 nm) Rt 8.5 min; Mass spectrum: Found: MH$^+$ 417 ($^{35}$Cl).

EXAMPLE 28

3-Chloro-N-ethyl-N-phenyl-5-[2-(pyridin-4-ylamino)-ethoxy]-benzamide hydrochloride A solution {2-[3-chloro-5-(ethyl-phenyl-carbamoyl)-phenoxy]-ethyl}-pyridin-4-yl-carbamic acid tert-butyl ester (0.080 g) in a mixture of dichloromethane (1 ml) and trifluoroacetic acid (1 ml) was stored at room temperature for 90 min and then concentrated under reduced pressure. The residue was triturated with ethereal hydrogen chloride to give the title compound (0.068 g) as a colourless solid.

Hplc system 1 ($\lambda$=254 nm) Rt 7.7 min; Mass spectrum: Found: MH$^+$ 396.1483 C$_{22}$H$_{23}$$^{35}$Cl$_1$N$_3$O$_2$ requires 396.1479.

EXAMPLE 29

3-Chloro-N-(3,5-difluoro-phenyl)-N-propyl-5-[2-(pyridin-4-ylamino)-ethoxy]-benzamide trifluoroacetate A solution (2-{3-chloro-5-[(propyl)-(3,5-difluoro-phenyl)-carbamoyl]-phenoxy}-ethyl)-pyridin-4-yl-carbamic acid tert-butyl ester (0.029 g) in trifluoroacetic acid (2 ml) was stored at room temperature for 18 h and then concentrated under reduced pressure.

The residue was subjected to preparative hplc and the title compound (0.020 g) was obtained as a colourless gum by concentration of the required fraction under reduced pressure and drying by repetitive addition of acetonitrile and concentration under reduced pressure.

Hplc system 1 ($\lambda$=254 nm) Rt 9.0 min; Mass spectrum: Found: MH$^+$ 446 ($^{35}$Cl).

EXAMPLE 30

3-Chloro-N-ethyl-N-(2-fluoro-phenyl)-5-[2-(pyridin-4-ylamino)-ethoxy]-benzamide trifluoroacetate 2M Oxalyl chloride solution in dichloromethane (0.080 ml) and DMF (0.001 ml) were added to a suspension of 3-[2-(tert-butoxycarbonyl-pyridin-4-yl-amino)-ethoxy]-5-chloro-benzoic acid (0.050 g) in anhydrous dichloromethane (1 ml). The reaction was stirred at room temperature for 2 h then a solution of N-ethyl-2-fluoroaniline (0.029 g) DMAP (0.001 g) and DIPEA (0.070 ml) were added. The reaction mixture was stirred at room temperature for 16 h and then triflouroacetic acid (1 ml) was added. The solvent was removed in vacuo, the residue was subjected to preparative hplc and the required fraction dried by repetitive addition of acetonitrile and concentration under reduced pressure to give the title compound (0.020 g) as a colourless gum.

Hplc system 1 ($\lambda$=254 nm) Rt 7.9 min; Mass spectrum: Found: MH$^+$ 414 ($^{35}$Cl).

EXAMPLE 31

N-(2-Carbamoyl-ethyl)-3-chloro-N-phenyl-5-[2-(pyridin-4-ylamino)-ethoxy]-benzamide trifluoroacetate 2M Oxalyl chloride solution in dichloromethane (0.090 ml) and DMF (0.001 ml) were added to a suspension of 3-[2-(tert-butoxycarbonyl-pyridin-4-yl-amino)-ethoxy]-5-chloro-benzoic acid (0.059 g) in anhydrous dichloromethane (1 ml). The reaction was stirred at room temperature for 2 h then 3-phenylamino-propionitrile[8] (0.027 g), DMAP (0.002 g) and DIPEA (0.078 ml) were added. The reaction mixture was stirred at room temperature for 2 h then trifluoroacetic acid (2 ml) was added and the reaction mixture stirred overnight open to the air. The reaction mixture was concentrated in vacuo and the residue was subjected to preparative hplc. The title compound (0.060 g) was obtained as a colourless gum by concentration of the required fraction under reduced pressure and drying by repetitive addition of acetonitrile and concentration under reduced pressure.

Hplc system 1 ($\lambda$=254 nm) Rt 5.9 min; Mass spectrum: Found: MH$^+$ 439.1528 C$_{23}$H$_{24}$$^{35}$Cl$_1$N$_4$O$_3$ requires 439.1537.

EXAMPLE 32

N-(2-Carbamoyl-ethyl)-3-chloro-N-(2-fluoro-phenyl)-5-[2-(pyridin-4-ylamino)-ethoxy]-benzamide trifluoroacetate A solution of (2-{3-chloro-5-[(2-cyano-ethyl)-(2-fluoro-phenyl)-carbamoyl]-phenoxy}-ethyl)-pyridin-4-yl-carbamic acid tert-butyl ester (0.055 g) and water (0.020 ml) in a mixture of trifluoroacetic acid (1 ml) and dichloromethane (1 ml) was stirred at room temperature for 2 h and then the solvent removed under reduced pressure. The residue was purified by preparative hplc to give the title compound (0.035 g) as a colourless gum by concentration of the required fraction under reduced pressure and drying by repetitive addition of acetonitrile and concentration under reduced pressure.

Hplc system 1 ($\lambda$=254 nm) Rt 5.7 min; Mass spectrum: Found: MH$^+$ 457.1435 C$_{23}$H$_{23}$$^{35}$Cl$_1$F$_1$N$_4$O$_3$ requires 457.1443.

EXAMPLE 33

N-(2-Carbamoyl-ethyl)-3-chloro-N-(2-chloro-phenyl)-5-[2-(pyridin-4-ylamino)-ethoxy]-benzamide trifluoroacetate A solution of (2-{3-chloro-5-[(2-chloro-phenyl)-(2-cyano-ethyl)-carbamoyl]-phenoxy}-ethyl)-pyridin-4-yl-carbamic acid tert-butyl ester (0.055 g) and water (0.020 ml) in a mixture of trifluoroacetic acid (1 ml) and dichloromethane (1 ml) was stirred at room temperature for 2 h and then the solvent removed under reduced pressure. The residue was purified by preparative hplc to give title compound (0.035 g) as a colourless gum by concentration of the required fraction under reduced pressure and drying by repetitive addition of acetonitrile and concentration under reduced pressure.

Hplc system 1 ($\lambda$=254 nm) Rt 6.0 min; Mass spectrum: Found: MH$^+$ 473.1130 $C_{23}H_{23}{}^{35}Cl_2N_4O_3$ requires 473.1147.

EXAMPLE 34

4-[{3-Chloro-5-[2-(pyridin-4-ylamino)-ethoxy]-benzoyl}-(2-fluoro-phenyl)-amino]-butyric acid methyl ester trifluoroacetate A solution of 4-[{3-[2-(tert-butoxycarbonyl-pyridin-4-yl-amino)-ethoxy]-5-chloro-benzoyl}-(2-fluoro-phenyl)-amino]-butyric acid methyl ester (0.020 g) in a mixture of dichloromethane (1 ml) and trifluoroacetic acid (1 ml) was stored at room temperature for 16 h and then concentrated under reduced pressure to give the title compound (0.022 g) as a colourless gum.

Hplc system 1 ($\lambda$=254 nm) Rt 8.1 min; Mass spectrum: Found: MH$^+$ 486.1576 $C_{25}H_{26}{}^{35}Cl_1F_1N_3O_4$ requires 486.1596.

EXAMPLE 35

4-[{3-Chloro-5-[2-(pyridin-4-ylamino)-ethoxy]-benzoyl}-(2-fluoro-phenyl)-amino]-butyric acid A solution of 4-[{3-[2-(tert-butoxycarbonyl-pyridin-4-yl-amino)-ethoxy]-5-chloro-benzoyl}-(2-fluoro-phenyl)-amino]-butyric acid (0.020 g) in a mixture of dichloromethane (1 ml) and trifluoroacetic acid (1 ml) was stored at room temperature for 2 h and then concentrated under reduced pressure to give the title compound (0.0239) as a colourless gum.

Hplc system 3 ($\lambda$=220–330 nm) Rt 3.1 min; Mass spectrum: Found: MH$^+$ 472.1453 $C_{24}H_{24}{}^{35}Cl_1F_1N_3O_4$ requires 472.1439.

EXAMPLE 36

N-(3-Carbamoyl-propyl)-3-chloro-N-(2-fluoro-phenyl)-5-[2-(pyridin-4-ylamino)-ethoxy]-benzamide trifluoroacetate A solution of (2-{3-[(3-Carbamoyl-propyl)-(2-fluoro-phenyl)-carbamoyl]-5-chloro-phenoxy}-ethyl)-pyridin-4-yl-carbamic acid tert-butyl ester (0.030 g) in trifluoroacetic acid (2 ml) was stored at room temperature for 18 h and then concentrated under reduced pressure. The residue was subjected to preparative hplc and the title compound (0.009 g) was obtained as a colourless gum by concentration of the required fraction under reduced pressure and drying by repetitive addition of acetonitrile and concentration under reduced pressure.

Hplc system 1 ($\lambda$=254 nm) Rt 6.0 min; Mass spectrum: Found: MH$^+$ 471.1594 $C_{24}H_{25}{}^{35}Cl_1F_1N_4O_3$ requires 471.1599.

EXAMPLE 37

3-Chloro-N-(2-fluoro-phenyl)-N-(4-oxo-4-pyrrolidin-1-yl-butyl)-5-[2-(pyridin-4-ylamino)-ethoxy]-benzamide trifluoroacetate A solution of (2-{3-chloro-5-[(2-fluoro-phenyl)-(4-oxo-4-pyrrolidin-1-yl-butyl)-carbamoyl]-phenoxy}-ethyl)-pyridin-4-yl-carbamic acid tert-butyl ester (0.025 g) in mixture of trifluoroacetic acid (1 ml) and dichloromethane (1 ml) was stored at room temperature for 1 h and then the solvent removed under reduced pressure. The residue was subjected to preparative hplc to give the title compound (0.024 g) as a colourless gum by concentration of the required fraction under reduced pressure and drying by repetitive addition of acetonitrile and concentration under reduced pressure.

Hplc system 1 ($\lambda$=254 nm) Rt 7.7 min; Mass spectrum: Found: MH$^+$ 525.2063 $C_{28}H_{31}{}^{35}Cl_1F_1N_4O_3$ requires 525.2068.

EXAMPLE 38

4-((2-Carbamoyl-phenyl)-{3-chloro-5-[2-(pyridin-4-ylamino)-ethoxy]-benzoyl}-amino)-butyric acid methyl ester trifluoroacetate A solution of 4-[{3-[2-(tert-butoxycarbonyl-pyridin-4-yl-amino)-ethoxy]-5-chloro-benzoyl}-(2-carbamoyl-phenyl)-amino]-butyric acid methyl ester (0.031 g) in a mixture of dichloromethane (1 ml) and trifluoroacetic acid (1 ml) was stored at room temperature for 1 h and then concentrated under reduced pressure to give the title compound (0.032 g) as a colourless gum.

Hplc system 1 ($\lambda$=254 nm) Rt 6.2 min; Mass spectrum: Found: MH$^+$ 511.

EXAMPLE 39

4-((2-Carbamoyl-phenyl)-{3-chloro-5-[2-(pyridin-4-ylamino)-ethoxy]-benzoyl}-amino)-butyric acid 2M Aqueous sodium hydroxide (0.200 ml) was added to a stirred solution of 4-((2-carbamoyl-phenyl)-{3-chloro-5-[2-(pyridin-4-ylamino)-ethoxy]-benzoyl}-amino)-butyric acid methyl ester trifluoroacetate (0.030 g) in 1,4-dioxan (1 ml). 2M Aqueous hydrochloric acid (0.2 ml) was added after 16 h. The reaction mixture was evaporated in vacuo and the residue was subjected to preparative hplc to give the title compound (0.024 g) as a colourless gum by concentration of the required fraction under reduced pressure and drying by repetitive addition of acetonitrile and concentration under reduced pressure.

Hplc system 2 ($\lambda$=254) Rt 8.0 min; Mass spectrum: Found: (M-H$_2$O)H$^+$ 479.1492 $C_{25}H_{24}{}^{35}Cl_1N_4O_4$ requires 479.1486.

EXAMPLE 40

3-Chloro-N-(2-fluoro-phenyl)-5-[2-(pyridin-4-ylamino)-ethoxy]-N-[3-(1H-tetrazol-5-yl)-propyl]-benzamide A mixture of (2-{3-chloro-5-[(3-cyano-propyl)-2-fluoro-phenyl)-carbamoyl]-phenoxy}-ethyl)-pyridin-4-ylcarbamic acid tert-butyl ester (0.132 g) and tributyltin azide (1.2 ml) was heated at 160° C. for 5 h. The reaction mixture was cooled to room temperature and 1M ethereal hydrogen chloride was added. The reaction mixture was partioned between acetonitrile and petroleum ether. The acetonitrile layer was removed and extracted further with petroleum ether. The acetonitrile layer was then subjected to prepartive hplc to give the title compound as a colourless gum by concentration of the required fraction under reduced pressure and drying by repetitive addition of acetonitrile and concentration under reduced pressure.

Hplc system 1 ($\lambda$=254 nm) Rt 6.6 min; Mass spectrum: Found: MH$^+$ 496.1684 $C_{24}H_{24}{}^{35}Cl_1F_1N_7O_2$ requires 496.1664.

EXAMPLE 41

3-Chloro-N-[2-(2,3-dihydroxy-propoxy)-ethyl]-N-phenyl-5-[2-(pyridin-4-ylamino)-ethoxy]-benzamide trifluoroacetate A solution of [2-(3-chloro-5-{[2-(2,2-dimethyl-[1,3] dioxolan-4-ylmethoxy)-ethyl]-phenyl-carbamoyl}-phenoxy)-ethyl]-pyridin-4-yl-carbamic acid tert-butyl ester (0.037 g) in mixture of trifluoroacetic acid (1 ml) and dichloromethane (1 ml) was stored at room temperature for 3 h and then the solvent removed under reduced pressure. The residue was subjected to preparative hplc to give the title compound (0.010 g) as a colourless gum by concentration of the required fraction under reduced pressure and drying by repetitive addition of acetonitrile and concentration under reduced pressure.

Hplc system 1 ($\lambda$=254 nm) Rt 5.9 min; Mass spectrum: Found: MH$^+$ 486 ($^{35}$Cl).

EXAMPLE 42

3-Chloro-N-[2-(2,3-dihydroxy-propoxy)-ethyl]-N-(2-fluoro-phenyl)-5-[2-(pyridin-4-ylamino)-ethoxy]-benzamide trifluoroacetate A solution of (2-{3-chloro-5-[[2-(2,2-dimethyl-[1,3] dioxolan-4-ylmethoxy)-ethyl]-(2-fluoro-phenyl)-carbamoyl]-phenoxy}-ethyl)-pyridin-4-yl-carbamic acid tert-butyl ester (0.035 g) and water (0.010 ml) in mixture of trifluoroacetic acid (1 ml) and dichloromethane (1 ml) was stored at room temperature for 3 h and then the solvent removed under reduced pressure. The residue was subjected to preparative hplc to give the title compound (0.022 g) as a colourless gum by concentration of the required fraction under reduced pressure and drying by repetitive addition of acetonitrile and concentration under reduced pressure.

Hplc system 1 ($\lambda$=254 nm) Rt 5.8 min; Mass spectrum: Found: MH$^+$ 504.1709 $C_{25}H_{28}{}^{35}Cl_1F_1N_3O_5$ requires 504.1701.

EXAMPLE 43

3-Chloro-N-[2-(2,3-dihydroxy-propoxy)-ethyl]-N-(4-fluoro-phenyl)-5-[2-(pyridin-4-ylamino)-ethoxy]-benzamide hydrochloride A solution of (2-{3-chloro-5-[[2-(2,2-dimethyl-[1,3] dioxolan-4-ylmethoxy)-ethyl]-(4-fluoro-phenyl)-carbamoyl]-phenoxy}-ethyl)-pyridin-4-yl-carbamic acid tert-butyl ester (0.042 g) in mixture of trifluoroacetic acid (1 ml) and dichloromethane (1 ml) was stored at room temperature for 3 h and then the solvent removed under reduced pressure. The residue was dissolved in a mixture of acetonitrile (2 ml) amd 2M aqueous hydrochloric acid (0.5 ml) and subjected to preparative hplc to give title compound (0.022 g) as a colourless gum by concentration of the required fraction under reduced pressure and drying by repetitive addition of acetonitrile and concentration under reduced pressure.

Hplc system 1 ($\lambda$=254 nm) Rt 5.8 min; Mass spectrum: Found: MH$^+$ 504.1709 $C_{25}H_{28}{}^{35}Cl_1F_1N_3O_5$ requires 504.1701.

EXAMPLE 44

(R)-1-{3-[{3-Chloro-5-[2-(pyridin-4-ylamino)-ethoxy]-benzoyl}-(2-fluoro-phenyl)-amino]-propyl}-pyrrolidine-2-carboxylic acid trifluoroacetate A solution of (R)-1-{3-[{3-[2-(tert-butoxycarbonyl-pyridin-4-yl-amino)-ethoxy]-5-chloro-benzoyl}-(2-fluoro-phenyl)-amino]-propyl}-pyrrolidine-2-carboxylic acid tert-butyl ester and (R)-1-[3-(2-fluoro-phenylamino)-propyl]-pyrrolidine-2-carboxylic acid tert butyl ester (0.110 g) in trifluoroacetic acid (5 ml) for 18 h and then the solvent removed under reduced pressure. The residue was subjected to preparative hplc to give the title compound (0.027 g) as a colourless gum by concentration of the required fraction under reduced pressure and drying by repetitive addition of acetonitrile and concentration under reduced pressure.

Hplc system 1 ($\lambda$=254 nm) Rt 5.5 min; Mass spectrum: Found: MH$^+$ 541.2000 $C_{28}H_{30}{}^{35}Cl_1F_1N_4O_4$ requires 541.2018.

EXAMPLE 45

3-Chloro-N-(3-oxo-3-piperidin-1-yl-propyl)-N-phenyl-5-[2-(pyridin-4-ylamino)-ethoxy]-benzamide trifluoroacetate The following procedure was performed using a TECAN despensing robot. To a 0.1M solution of 3-({3-[2-(tert-butoxycarbonyl-pyridin-4-yl-amino)-ethoxy]-5-chloro-benzoyl}-phenyl-amino)-propionic acid in DMF (0.250 ml) was dispensed a 0.4M solution of PyBroP® in DMF (0.125 ml) and a 0.2M solution of piperidine (0.375 ml). Finally a 1M solution of DIPEA in DMF (0.100 ml) was added to the reaction mixture. The reaction mixture was stored at room temperature for 24 h, and then concentrated. The residue was stored in a mixture of dichloromethane (0.5 ml) and trifluoroacetic acid (1 ml) for 6 h and concentrated. The residue was then subjected to preparative hplc and the title compound (0.008 g) obtained as a colourless gum by concentration of the required fraction under reduced pressure and drying by repetitive addition of acetonitrile and concentration under reduced pressure.

Hplc system 3 ($\lambda$=220–330 nm) Rt 3.8 min; Mass spectrum: Found: MH$^+$ 506 ($^{35}$Cl).

Using commercially available amines, the following compounds were prepared by the same method:

EXAMPLE 46

3-Chloro-N-[2-(ethyl-methyl-carbamoyl)-ethyl]-N-phenyl-5-[2-(pyridin-4-ylamino)-ethoxy]-benzamide trifluoroacetate Hplc system 3 ($\lambda$=220–330 nm) Rt 3.6 min; Mass spectrum: Found: MH$^+$ 481 ($^{35}$Cl).

EXAMPLE 47

N-(2-tert-Butylcarbamoyl-ethyl)-3-chloro-N-phenyl-5-[2-(pyridin-4-ylamino)ethoxy]-benzamide trifluoroacetate Hplc system 3 ($\lambda$=220–330 nm) Rt 3.7 min; Mass spectrum: Found: MH$^+$ 495 ($^{35}$Cl).

EXAMPLE 48

3-Chloro-N-[2-(2,2-dimethyl-propylcarbamoyl)-ethyl]-N-phenyl-5-[2-(pyridin-4-ylamino)-ethoxy]-benzamide trifluoroacetate Hplc system 3 ($\lambda$=220–330 nm) Rt 3.8 min; Mass spectrum: Found: MH$^+$ 509 ($^{35}$Cl).

EXAMPLE 49

3-Chloro-N-(3-oxo-3-thiomorpholin-4-yl-propyl)-N-phenyl-5-[2-(pyridin-4-ylamino)-ethoxy]-benzamide trifluoroacetate Hplc system 3 ($\lambda$=220–330 nm) Rt 3.7 min; Mass spectrum: Found: MH$^+$ 525 ($^{35}$Cl).

EXAMPLE 50

3-Chloro-N-(3-oxo-3-thiazolidin-3-yl-propyl)-N-phenyl-5-[2-(pyridin-4-ylamino)-ethoxy]-benzamide trifluoroacetate Hplc system 3 ($\lambda$=220–330 nm) Rt 3.6 min; Mass spectrum: Found: MH$^+$ 511 ($^{35}$Cl).

EXAMPLE 51

3-Chloro-N-phenyl-5-[2-(pyridin-4-ylamino)-ethoxy]-N-(2-sulfamoyl-ethyl)-benzamide trifluoroacetate A solution of (2-{3-chloro-5-[(2-fluorosulfonyl-ethyl)-phenyl-carbamoyl]-phenoxy}-ethyl)-pyridin-4-yl-carbamic acid tert-butyl ester (0.017 g) in a mixture of acetone (10 ml) and ammonia (0.88) was stirred at 80° C. for 3 h. The solvent was removed under reduced pressure and the residue subjected to preparative hplc. A solution of this product in a mixture of trifluoroacetic acid (3 ml) and dichloromethane (1.5 ml) was stored for 1 h then evaporated to give the title compound as a colourless gum (0.009 g).

Hplc system 1 ($\lambda$=254 nm) Rt 6.4 min; Mass spectrum: Found: MH$^+$ 475.1214 C$_{22}$H$_{24}$$^{35}$Cl$_1$N$_4$O$_4$S$_1$ requires 475.1207.

EXAMPLE 52

N-(2-tert-Butylsulfamoyl-ethyl)-3-chloro-N-phenyl-5-[2-(pyridin-4-ylamino)-ethoxy]-benzamide trifluoroacetate A solution of (2-{3-chloro-5-[(2-fluorosulfonyl-ethyl)-phenyl-carbamoyl]-phenoxy}-ethyl)-pyridin-4-yl-carbamic acid tert-butyl ester (0.020 g) in tert-butylamine (0.75 ml) was stored at room temperature for 24 h. The amine was evaporated and the residue dissolved in a mixture of trifluoroacetic acid (1 ml) and dichloromethane (0.5 ml) and was stored for 64 h. The solvent was removed and the residue subjected to preparative hplc. The title compound (0.015 g) was obtained as a yellow gum by concentration of the required fraction under reduced pressure and drying by repetitive addition of acetonitrile and concentration under reduced pressure.

Hplc system 1 ($\lambda$=254 nm) Rt 7.8 min; Mass spectrum: Found: MH$^+$ 531 ($^{35}$Cl).

EXAMPLE 53

3-Chloro-N-(2-isopropylsulfamoyl-ethyl)-N-phenyl-5-[2-(pyridin-4-ylamino)-ethoxy]-benzamide trifluoroacetate A solution of (2-{3-chloro-5-[(2-fluorosulfonyl-ethyl)-phenyl-carbamoyl]-phenoxy}-ethyl)-pyridin-4-yl-carbamic acid tert-butyl ester (0.020 g) in isopropylamine (0.75 ml) was stored at room temperature for 24 h. The amine was evaporated in vacuo and the residue dissolved in a mixture of trifluoroacetic acid (1 ml) and dichloromethane (0.5 ml) was stored for 64 h. The solvent was removed and the residue subjected to preparative hplc. The title compound (0.015 g) was obtained as a colourless gum by concentration of the required fraction under reduced pressure and drying by repetitive addition of acetonitrile and concentration under reduced pressure.

Hplc system 1 ($\lambda$=254 nm) Rt 7.8 min; Mass spectrum: Found: MH$^+$ 517 ($^{35}$Cl).

EXAMPLE 54

3-Chloro-N-isopropyl-N-[2-(1-methyl-1H-tetrazol-5-yl)-ethyl]-5-[2-(pyridin-4-ylamino)-ethoxy]-benzamide trifluoroacetate A solution of [2-(3-chloro-5-{isopropyl-[2-(1-methyl-1H-tetrazol-5-yl)-ethyl]-carbamoyl}phenoxy)-ethyl]-pyridin-4-yl-carbamic acid tert-butyl ester (0.028 g) in a mixture of dichloromethane (0.5 ml) and trifluoroacetic acid (1 ml) was stored at room temperature for 2 h and then concentrated under reduced pressure. The residue was subjected to preparative hplc and the title compound (0.023 g) was obtained as a colourless gum by concentration of the required fraction under reduced pressure and drying by repetitive addition of acetonitrile and concentration under reduced pressure.

Hplc system 1 ($\lambda$=254 nm) Rt 6.1 min; Mass spectrum: Found: MH$^+$ 444.1913 C$_{21}$H$_{27}$$^{35}$Cl$_1$N$_7$O$_2$ requires 444.1915.

EXAMPLE 55

N-(2-Carbamoyl-ethyl)-3-chloro-N-cyclopropylmethyl-5-[2-(pyridin-4-ylamino)-ethoxy]-benzamide trifluoroacetate A solution of (2-{3-chloro-5-[(2-cyano-ethyl)-cyclopropylmethyl-carbamoyl]-phenoxy}-ethyl)-pyridin-4-yl-carbamic acid tert-butyl ester (0.07 g) in a mixture of dichloromethane (5 ml) and trifluoroacetic acid (2 ml) was stored at room temperature for 18 h and then concentrated under reduced pressure to give the title compound as a light brown oil (0.071 g).

Hplc system 1 ($\lambda$=254 nm) Rt 5.8 min; Mass spectrum: Found: MH$^+$ 417.1709 C$_{21}$H$_{26}$$^{35}$ClN$_4$O$_3$ requires 417.1693.

EXAMPLE 56

N-(2-Carbamoyl-ethyl)-3-chloro-N-(2,2-dimethyl-propyl)-5-[2-(pyridin-4-ylamino)-ethoxy]-benzamide trifluoroacetate A solution of (2-{3-chloro-5-[(2-cyano-ethyl)-(2,2-dimethyl-propyl)-carbamoyl]-phenoxy}-ethyl)-pyridin-4-yl-carbamic acid tert-butyl ester (0.052 g) in a mixture of dichloromethane (5 ml) and trifluoroacetic acid (2 ml) was stored at room temperature for 18 h and then concentrated under reduced pressure. The residue was subjected to preparative hplc and the title compound (0.02 g) was obtained as a colourless oil by concentration of the required fraction under reduced pressure and drying by repetitive addition of acetonitrile and concentration under reduced pressure.

Hplc system 1 ($\lambda$=254 nm) Rt 6.4 min; Mass spectrum: Found: MH$^+$ 433.1995 C$_{22}$H$_{30}$$^{35}$ClN$_4$O$_3$ requires 433.2006.

EXAMPLE 57

N-(2-Carbamoyl-ethyl)-3-chloro-5-[2-(pyridin-4-ylamino)-ethoxy]-N-(tetrahydro-furan-2-ylmethyl)-benzamide trifluoroacetate A solution of (2-{3-chloro-5-[(2-cyano-ethyl)-tetrahydro-furan-2-ylmethyl)-carbamoyl]-phenoxy}-ethyl)-pyridin-4- yl-carbamic acid tert-butyl ester (0.052 g) in a mixture of dichloromethane (5 ml) and trifluoroacetic acid (2 ml) was stored at room temperature for 18 h and then concentrated under reduced pressure. The residue was subjected to preparative hplc and the title compound (0.037 g) was obtained as a colourless oil by concentration of the required fraction under reduced pressure and drying by repetitive addition of acetonitrile and concentration under reduced pressure.

Hplc system 1 ($\lambda$=254 nm) Rt 5.3 min; Mass spectrum: Found: MH$^+$ 447.1807 C$_{22}$H$_{28}$$^{35}$ClN$_4$O$_4$ requires 447.1799.

EXAMPLE 58

N-(2-Carbamoyl-ethyl)-3-chloro-N-isopropyl-5-[2-(pyridin-4-ylamino)-ethoxy]-benzamide trifluoroacetate A solution of (2-{3-chloro-5-[(2-cyano-ethyl)-isopropyl-carbamoyl]-phenoxy}-ethyl)-pyridin-4-yl-carbamic acid tert-butyl ester (0.071 g) in a mixture of dichloromethane (4 ml) and trifluoroacetic acid (1 ml) was stored at room temperature for 12 h and then concentrated under reduced pressure. The residue was subjected to preparative hplc and the title compound (0.045 g) was obtained as a yellow oil by concentration of the required fraction under reduced pressure and drying by repetitive addition of acetonitrile and concentration under reduced pressure.

Hplc system 1 ($\lambda$=254 nm) Rt 5.1 min; Mass spectrum: Found: MH$^+$ 405 ($^{35}$Cl).

EXAMPLE 59

N-(2-Carbamoyl-ethyl)-3-chloro-N-isobutyl-5-[2-(pyridin-4-ylamino)-ethoxy]-benzamide trifluoroacetate A solution of (2-{3-chloro-5-[(2-cyano-ethyl)-isobutyl-carbamoyl]-phenoxy}ethyl)-pyridin-4-yl-carbamic acid tert-butyl ester (0.059 g) in a mixture of dichloromethane (5 ml) and trifluoroacetic acid (2 ml) was stored at room temperature for 18 h and then concentrated under reduced pressure. The residue was subjected to preparative hplc and the title compound (0.047 g) was obtained as a colourless oil by concentration of the required fraction under reduced pressure and drying by repetitive addition of acetonitrile and concentration under reduced pressure.

Hplc system 1 ($\lambda$=254 nm) Rt 5.7 min; Mass spectrum: Found: MH$^+$ 419 ($^{35}$Cl).

EXAMPLE 60

3-Chloro-N-(2-diethylcarbamoyl-ethyl)-N-isopropyl-5-[2-(pyridin-4-ylamino)-ethoxy]-benzamide trifluoroacetate A solution of (2-{3-chloro-5-[(2-diethylcarbamoyl-ethyl)-isopropyl-carbamoyl]-phenoxy}-ethyl)-pyridin-4-yl-carbamic acid tert-butyl ester trifluoroacetate (0.06 g) in a mixture of dichloromethane (2 ml) and trifluoroacetic acid (1 ml) was stored at room temperature for 3 h and then concentrated under reduced pressure to give the title compound as a colourless oil (0.043 g).

Hplc system 1 ($\lambda$=254 nm) Rt 7.6 min; Mass spectrum: Found: MH$^+$ 461 ($^{35}$Cl).

EXAMPLE 61

3-Chloro-N-isopropyl-N-(3-oxo-3-piperidin-1-yl-propyl)-5-[2-(pyridin-4-ylamino)-ethoxy]-benzamide trifluoroacetate To a stirred solution of 3-({3-[2-(tert-butoxycarbonyl-pyridin-4-yl-amino)-ethoxy]-5-chloro-benzoyl}-isopropyl-amino)-propionic acid hydrochloride (0.02 g) and PyBroP® (0.035 g) in DMF (0.45 ml) was added DIPEA (0.026 ml) followed by piperidine (0.014 ml) after 5 min. The reaction was stirred at room temperature for 24 h, and then concentrated under reduced pressure. The remaining solid residue was stored in a mixture of dichloromethane (2 ml) and trifluoroacetic acid (1 ml) for 6 h, and then concentrated under reduced pressure. The residue was then subjected to preparative hplc and the title compound (0.011 g) obtained as a colourless oil by concentration of the required fraction under reduced pressure and drying by repetitive addition of acetonitrile and concentration under reduced pressure.

Hplc system 3 ($\lambda$=220–330 nm) Rt 3.65 min; Mass spectrum: Found: MH$^+$ 473 ($^{35}$Cl).

Using commercially available amines, the following compounds were prepared in a similar manner:

EXAMPLE 62

3-Chloro-N-[2-(3-methyl-but-2-yl-carbamoyl)-ethyl]-N-isopropyl-5-[2-(pyridin-4-ylamino)-ethoxy]-benzamide trifluoroacetate Hplc system 1 ($\lambda$=254 nm) Rt 8.0 min; Mass spectrum: Found: MH$^+$ 475 ($^{35}$Cl).

EXAMPLE 63

3-Chloro-N-[2-(3,3-dimethyl-but-2-yl-carbamoyl)-ethyl]-N-isopropyl-5-[2-(pyridin-4-ylamino)-ethoxy]-benzamide trifluoroacetate Hplc system 1 ($\lambda$=254 nm) Rt 8.5 min; Mass spectrum: Found: MH$^+$ 489 ($^{35}$Cl).

EXAMPLE 64

3-Chloro-N-[2-(ethyl-methyl-carbamoyl)-ethyl]-N-isopropyl-5-[2-(pyridin-4-ylamino)-ethoxy]-benzamide trifiuoroacetate Hplc system 3 ($\lambda$=220–330 nm) Rt 3.5 min; Mass spectrum: Found: MH$^+$ 447 ($^{35}$Cl).

EXAMPLE 65

3-Chloro-N-isopropyl-N-(3-oxo-3-pyrrolidin-1-yl-propyl)-5-[2-(pyridin-4-ylamino)-ethoxy]-benzamide trifluoroacetate Hplc system 3 ($\lambda$=220–330 nm) Rt 3.5 min; Mass spectrum: Found: MH$^+$ 459 ($^{35}$Cl).

EXAMPLE 66

3-Chloro-N-isopropyl-N-(3-morpholin-4-yl-3-oxo-propyl)-5-[2-(pyridin-4-ylamino)-ethoxy]-benzamide mixture with 3-({3-chloro-5-[2-(pyridin-4-ylamino)-ethoxy]-benzoyl}-isopronyl-amino)-propionic acid (1:2) trifluoroacetate Hplc system 3 ($\lambda$=220–330 nm) Rt 3.4 min; Mass spectrum: Found: MH$^+$ 475 ($^{35}$Cl).

EXAMPLE 67

N-(2-tert-Butylcarbamoyl-ethyl)-3-chloro-N-isopropyl-5-[2-(pyridin-4-ylamino)-ethoxy]-benzamide trifluoroacetate Hplc system 3 ($\lambda$=220–330 nm) Rt 3.7 min; Mass spectrum: Found: MH$^+$ 461 ($^{35}$Cl).

EXAMPLE 68

3-Chloro-N-[2-(2,2-dimethyl-propylcarbamoyl)-ethyl]-N-isopropyl-5-[2-(pyridin-4-ylamino)-ethoxy]-benzamide trifluoroacetate Hplc system 3 ($\lambda$=220–330 nm) Rt 3.7 min; Mass spectrum: Found: MH$^+$ 475 ($^{35}$Cl).

EXAMPLE 69

3-Chloro-N-isopropyl-N-(3-oxo-3-thiomorpholin-4-yl-propyl)-5-[2-(pyridin-4-ylamino)-ethoxy]-benzamide trifluoroacetate Hplc system 3 ($\lambda$=220–330 nm) Rt 3.6 min; Mass spectrum: Found: MH$^+$ 491 ($^{35}$Cl).

EXAMPLE 70

3-Chloro-N-isopropyl-N-(3-oxo-3-thiazolidin-3-yl-propyl)-5-[2-(pyridin-4-ylamino)-ethoxy]-benzamide trifluoroacetate Hplc system 3 ($\lambda$=220–330 nm) Rt 3.6 min; Mass spectrum: Found: MH$^+$ 477 ($^{35}$Cl).

EXAMPLE 71

3-Chloro-N-[2-(1,1-dimethyl-propylcarbamoyl)-ethyl]-N-isopropyl-5-[2-(pyridin-4-ylamino)-ethoxy]-benzamide trifluoroacetate Hplc system 1 ($\lambda$=254 nm) Rt 8.4 min; Mass spectrum: Found: MH$^+$ 475.

EXAMPLE 72

3-Chloro-N-isopropyl-N-(3-methanesulfonylamino-propyl)-5-[2-(pyridin-4-ylamino)-ethoxy]-benzamide trifluoroacetate To a solution of N-(3-amino-propyl)-3-chloro-N-isopropyl-5-[2-(pyridin-4-ylamino)-ethoxy]-benzamide trifluoroacetate (0.02 g) in dry acetonitrile (1 ml) was added a mixture of methanesulfonyl chloride (0.005 g) and triethylamine (0.017 ml) in acetonitrile (1 ml). The resultant mixture was stirred at room temperature for 15 h, and then concentrated under reduced pressure. The residue was stored in a mixture of dichloromethane (1 ml) and trifluoroacetic acid (2 ml) for 4 h, and then concentrated under reduced pressure. The residue was then subjected to preparative hplc and the title compound obtained as a colourless oil by concentration of the required fraction under reduced pressure and drying by repetitive addition of acetonitrile and concentration under reduced pressure.

Hplc system 1 ($\lambda$=254 nm) Rt 6.5 min; Mass spectrum: Found: MH$^+$ 469 ($^{35}$Cl).

Using commercially available sulfonyl chlorides, the following compounds were prepared in a similar manner:

EXAMPLE 73

3-Chloro-N-isopropyl-N-[3-(propane-1-sulfonylamino)-propyl]-5-[2-(pyridin-4-ylamino)-ethoxy]-benzamide trifluoroacetate Hplc system 1 ($\lambda$=254 nm) Rt 8.0 min; Mass spectrum: Found: MH$^+$ 497 ($^{35}$Cl).

EXAMPLE 74

3-Chloro-N-(3-ethanesulfonylamino-propyl)-N-isopropyl-5-[2-(pyridin-4-ylamino)-ethoxy]-benzamide trifluoroacetate Hplc system 1 ($\lambda$=254 nm) Rt 6.7 min; Mass spectrum: Found: MH$^+$ 483 ($^{35}$Cl).

EXAMPLE 75

3-Chloro-N-isopropyl-N-[3-(propane-2-sulfonylamino)-propyl]-5-[2-(pyridin-4-ylamino)-ethoxy]-benzamide trifluoroacetate Hplc system 1 ($\lambda$=254 nm) Rt 8.9 min; Mass spectrum: Found: MH$^+$ 497 ($^{35}$Cl).

EXAMPLE 76

1-{3-Chloro-5-[2-(pyridin-4-ylamino)-ethoxy]-benzoyl}-piperidine-2-carboxylic acid trifluoroacetate 1-{3-[2-(tert-Butoxycarbonyl-pyridin-4-yl-amino)-ethoxy]-5-chloro-benzoyl}-piperidine-2-carboxylic acid ethyl ester (0.16 g) in 1,4-dioxan (2 ml) was treated with 2M sodium hydroxide solution (0.6 ml) and stored at room temperature for 18 h. The solution was concentrated under reduced pressure and the residue stored in a mixture of dichloromethane (1 ml) and trifluoroacetic acid (1 ml). After 3 h, the solution was concentrated under reduced pressure and the residue was subjected to preparative hplc. The title compound (0.100 g) was obtained as a colourless oil by concentration of the required fraction under reduced pressure and drying by repetitive addition of acetonitrile and concentration under reduced pressure.

Hpcl system 1 ($\lambda$=254 nm) Rt 7.6 min; Mass spectrum: Found: MH$^+$ 404 ($^{35}$Cl).

EXAMPLE 77

{3-Chloro-5-[2-(pyridin-4-ylamino)-ethoxy]-phenyl}-(2-methyl-piperidin-1-yl)-methanone trifluoroacetate A solution of {2-[3-chloro-5-(2-methyl-piperidine-1-carbonyl)-phenoxy]-ethyl}-pyridin-4-yl-carbamic acid tert-butyl ester (0.065 g) in a mixture of dichloromethane (5 ml) and trifluoroacetic acid (2 ml) was stored at room temperature for 5 h and then concentrated under reduced pressure. The residue was subjected to preparative hplc and the title compound (0.061 g) was obtained as a colourless oil by concentration of the required fraction under reduced pressure and drying by repetitive addition of acetonitrile and concentration under reduced pressure.

Hplc system 1 ($\lambda$=254 nm) Rt 8.1 min; Mass spectrum: Found: MH$^+$ 374 ($^{35}$Cl).

EXAMPLE 78

3-Chloro-N-cyclopentyl-5-[2-(pyridin-4-ylamino)-ethoxy]-N-(3-trifluoromethanesulfonylamino-propyl)-benzamide trifluoroacetate A solution of (2-{3-chloro-5-[cyclopentyl-(3-trifluoromethanesulfonylamino-propyl)-carbamoyl]-phenoxy}-ethyl)-pyridin-4-yl-carbamic acid tert-butyl ester (0.0118 g) in dichloromethane (1 ml) and trifluoroacetic acid (1 ml) was stored at room temperature for 19 h and then concentrated under reduced pressure. The title compound was obtained as a pale brown gum (0.010 g).

Hplc system 1 ($\lambda$=254 nm) Rt 10.2 min; Mass spectrum: Found: MH$^+$ 549.1567 $C_{23}H_{29}{}^{35}ClF_3N_4O_4S$ requires 549.1550.

EXAMPLE 79

3-Chloro-N-isopropyl-N-methyl-5-[2-(pyridin-4-ylamino)-ethoxy]-benzamide trifluoroacetate A solution of {2-[3-chloro-5-(isopropyl-methyl-carbamoyl)-phenoxy]-ethyl}-pyridin-4-yl-carbamic acid tert-butyl ester (0.060 g) in dichloromethane (4 ml) and trifluoroacetic acid (4 ml) was stored at room temperature for 2 h and then concentrated under reduced pressure. The residue was subjected to preparative hplc to give the title compound as a yellow gum (0.061 g).

Hplc system 1 ($\lambda$=254 nm) Rt 6.8 min; Mass spectrum: Found: MH$^+$ 348.1470 C$_{18}$H$_{23}$$^{35}$ClN$_3$O$_2$ requires 348.1479.

EXAMPLE 80

N-[2-(3-Amino-[1,2,4]oxadiazol-5-yl)-ethyl]-3-chloro-N-isopropyl-5-[2-(pyridin-4-ylamino)-ethoxy]-benzamide trifluoroacetate A solution of [2-(3-{[2-(3-amino[1,2,4]oxadiazol-5-yl)-ethyl]-isopropyl-carbamoyl}-5-chloro-phenoxy)-ethyl]-pyridin-4-yl-carbamic acid tert-butyl ester (0.064 g) in dichloromethane (1 ml) and trifluoroacetic acid (1 ml) was stored at room temperature for 5 h and then concentrated under reduced pressure. The residue was subjected to preparative hplc to give the title compound as a pale yellow foam (0.043 g).

Hplc system 1 ($\lambda$=254 nm) Rt 6.2 min; Mass spectrum: Found: MH$^+$ 445.1743 C$_{21}$H$_{26}$$^{35}$ClN$_6$O$_3$ requires 445.1755.

EXAMPLE 81

N-(2-Cyano-ethyl)-N-isopropyl-3-methyl-5-[2-(pyridin-4-ylamino)-ethoxy]-benzamide trifluoroacetate A solution of 3-methyl-5-[2-(pyridin-4-ylamino)-ethoxy]-benzoic acid trifluoroacetate salt (0.026 g) in anhydrous DMF (2 ml) was treated at room temperature with 3-isopropylamino-propionitrile$^9$ (0.017 g), PyBrop® (0.062 g) and DIPEA (0.025 ml). More PyBrop® was added after 2 days (0.072 g) and 7 days (0.065 g). More 3-isopropylamino-propionitrile was added after 2 days (0.03 ml), 4 days (0.1 ml) and 7 days (0.1 ml). After 24 h more, the mixture was evaporated to dryness under reduced pressure and the residue subjected to preparative hplc giving the title compound as a clear colourless gum (0.016 g).

Hplc system 2 ($\lambda$=254 nm) Rt 9.6 min; Mass spectrum: Found: MH$^+$ 367.2140 C$_{21}$H$_{27}$N$_4$O$_2$ requires 367.2134.

EXAMPLE 82

N-(2-Carbamoyl-ethyl)-N-isopropyl-3-methyl-5-[2-(pyridin-4-ylamino)-ethoxy]-benzamide trifluoroacetate A solution of N-(2-cyano-ethyl)-N-isopropyl-3-methyl-5-[2-(pyridin-4-ylamino)-ethoxy]-benzamide trifluoroacetate (0.011 g) in dichloromethane (1.5 ml) and trifluoroacetic acid (0.5 ml) was stored at room temperature overnight and then concentrated under reduced pressure. The title compound was obtained as a pale yellow foam (0.012 g).

Hplc system 2 ($\lambda$=254 nm) Rt 8.2 min; Mass spectrum: Found: MH$^+$ 385.

EXAMPLE 83

3-Chloro-N-isopropyl-5-[2-(pyridin-4-ylamino)]-N-(2-[1,2,4]triazol-1-yl-ethyl)-benzamide Tributyltin azide (1.0 g) was added to (2-{3-chloro-5-[(2-cyano-ethyl)-cyclopentyl-carbamoyl]-phenoxy}-ethyl)-pyridin-4-yl-carbamic acid tert-butyl ester (0.11 g). The neat mixture was heated at 160° C. for 4 h. cooled to room temperature and quenched with 2M sodium hydroxide solution and extracted with ether. The aqueous layer was acidified with 5M hydrochloric acid and subjected to preparative hplc to give the title compound (0.022 g) as a colourless oil.

Hplc system 1 ($\lambda$=254 nm) Rt 6.5 min; Mass spectrum: Found: MH$^+$ 456 ($^{35}$Cl).

EXAMPLE 84

3-Chloro-N-isopropyl-5-[2-(pyridin-4-ylamino)-ethoxy]-N-(2-[1,2,4]triazol-1-yl-ethyl)-benzamide trifluoroacetate To a solution of (2-{3-chloro-5-[isopropyl-(2-[1,2,4]triazol-1-yl-ethyl)-carbamoyl]-phenoxy}-ethyl)-pyridin-4-yl-carbamic acid tert-butyl ester (0.097 g) in dichloromethane (5 ml) was added trifluoroacetic acid (2 ml) and the mixture was stirred at room temperature for 3 h. The solvent was evaporated under reduced pressure and the residue subjected to preparative hplc to give the title compound (0.093 g) as a clear oil.

Hplc system 1 ($\lambda$=254 nm) Rt 6.0 min; Mass spectrum: Found: MH$^+$ 544 ($^{35}$Cl).

EXAMPLE 85

N-(3-Amino-propyl)-3-chloro-N-isopropyl-5-[2-(pyridin-4-ylamino)-ethoxy]-benzamide bis (trifluoroacetate)

A solution of (2-{3-[(3-amino-propyl)-isopropyl-carbamoyl]-5-chloro-phenoxy}-ethyl)-pyridin-4-yl-carbamic acid tert-butyl ester (0.025 g) in dichloromethane (1 ml) was treated with dichloromethane:trifluoroacetic acid (1:1 v/v) (1 ml), stirred for 3 h at room temperature and concentrated under reduced pressure. The residue was subjected to preparative hplc to give the title compound (0.018 g) as a light brown oil.

Hplc system 1 ($\lambda$=254 nm) Rt 4.9 min; Mass spectrum: Found: MH$^+$ 377 ($^{35}$Cl).

EXAMPLE 86

3-Chloro-N-isopropyl-5-[2-(pyridin-4-ylamino)-ethoxy]-N-(3-trifluoromethanesulfonylamino-propyl)-benzamide trifluoroacetate A solution of (2-{3-chloro-5-[isopropyl-(3-trifluoromethanesulfonylamino-propyl)-carbamoyl]-phenoxy}-ethyl)-pyridin-4-yl-carbamic acid tert-butyl ester trifluoroacetate (0.038 g) in dichloromethane (1 ml) was treated with dichloromethane:trifluoroacetic acid (1:1 v/v) (1 ml) stirred for 3 h at room temperature and concentrated under reduced pressure. The residue was subjected to preparative hplc to give the title compound (0.024 g) as an oil.

Hplc system 1 ($\lambda$=254 nm) Rt 8.9 min; Mass spectrum: Found: MH$^+$ 523 ($^{35}$Cl).

EXAMPLE 87

{3-Chloro-5-[2-(pyridin-4-ylamino)-ethoxy]-phenyl}-(2,5-dimethyl-pyrrolidin-1-yl)-methanone trifluoroacetate A solution of {2-[3-chloro-5-(2,5-dimethyl-pyrrolidine-1-carbonyl)-phenoxy]-ethyl}-pyridin-4-yl-carbamic acid tert-butyl ester (0.260 g) in dichloromethane (1 ml) was treated with dichloromethane:trifluoroacetic acid (1:1 v/v) (1 ml), stirred for 3 h at room temperature and concentrated under reduced pressure. The residue was taken up into ethyl acetate and filtered through silica (50 g) to give the title compound (0.102 g) as an oil.

Hplc system 1 ($\lambda$=254 nm) Rt 7.5 min; Mass spectrum: Found: MH$^+$ 374 ($^{35}$Cl).

EXAMPLE 88

3-Chloro-N-[3-(2,2-dimethyl-propionylamino)-propyl]-N-isopropyl-5-[2-(pyridin-4-ylamino)-ethoxy]-benzamide trifluoroacetate A solution of [2-(3-chloro-5-{[3-(2,2-dimethyl-propionylamino)-propyl]-isopropyl-carbamoyl}-phenoxy)-ethyl]-pyridine-4-yl-carbamic acid tert-butyl ester in dichloromethane (1 ml) was treated with dichloromethane:trifluoroacetic acid (1:1 v/v) (1 ml), stirred for 3 h at room temperature and concentrated under reduced pressure. The residue was subjected to preparative hplc to give the title compound (0.039 g) as an oil.

Hplc system 3 ($\lambda$=220–330 nm) Rt 3.7 min; Mass spectrum: Found: MH$^+$ 475 ($^{35}$Cl).

EXAMPLE 89

3-Chloro-N-[3-(2,2-dimethyl-propionylamino)-propyl]-N-isopropyl-5-[2-(pyridin-4-ylamino)-ethoxy]-benzamide trifluoroacetate To a solution of (2-{3-[(3-amino-propyl)-isopropyl-carbamoyl]-5-chloro-phenoxy}-ethyl)-pyridin-4-yl-carbamic acid tert-butyl ester (0.040 g), DIPEA (0.03 ml) in dichloromethane (1 ml) was added a solution of tert-butyl acetyl chloride (0.014 ml) in dichloromethane (1 ml) and the mixture was stirred for 3 h at room temperature. The mixture was evaporated under reduced pressure, was dissolved in dichloromethane (1 ml), was treated with 1 ml of dichloromethane:trifluoroacetic acid (1:1), stirred for 3 h at room temperature and concentrated under reduced pressure. The residue was subjected to preparative hplc to give the title compound (0.037 g) as an oil.

Hplc system 3 ($\lambda$=220–330 nm) Rt 2.7 min; Mass spectrum: Found MH$^+$ 489 ($^{35}$Cl).

EXAMPLE 90

3-Chloro-N-(4-fluoro-phenyl)-5-[2-(pyridin-4-ylamino)-ethoxy]-N-(3-[1,2,4]triazol-1-yl-propyl)-benzamide bis(trifluoroacetate)

A suspension of 3-[2-(tert-butoxycarbonyl-pyridin-4-yl-amino)-ethoxy]-5-chloro-benzoic acid (0.050 g), 4-fluorophenyl-(3-[1,2,4]triazol-1-yl-propyl)-amine (0.056 g) and EEDQ (0.050 g) in acetonitrile (1 ml) was stirred at 50° C. under nitrogen for 5 h. The solvent was removed and the residue was purified by flash chromatography on silica eluting with dichloromethane:methanol:ammonia (99:1:0.1 v/v/v). The resultant oil was treated with trifluoroacetic acid then concentrated under vacuum to give the title compound as a colourless gum (0.008 g).

Hplc system 3 ($\lambda$=220–330 nm) Rt 3.7 min; Mass spectrum: Found: MH$^+$ 495 ($^{35}$Cl).

EXAMPLE 91

3-Chloro-N-cyclopentyl-5-[2-(pyridin-4-ylamino)-ethoxy]-N-(2-[1,2,4]triazol-1-yl-ethyl)-benzamide A solution of 2-[3-chloro-5-(cyclopentyl-(2-[1,2,4] triazol-1-yl-ethyl)-carbamoyl)-phenoxy]-ethyl}-pyridin-4-yl-carbamic acid tert-butyl ester (0.022 g) and trifluoroacetic acid (0.5 ml) in dicloromethane (0.5 ml) was stirred at room temperature for 1 h then concentrated under vacuum. The residue was purified by flash chromatography eluting with dichloromethane:methanol (90:10 then 80:20 v/v) to give the title compound as an off-white powder (0.013 g).

Mass spectrum: Found: MH$^+$ 455 ($^{35}$Cl); Hplc system 1 ($\lambda$=254 nm) Rt 7.0 min.

EXAMPLE 92

3-Chloro-N-cyclopentyl-5-[2-(pyridin-4-ylamino)-ethoxy]-N-(4-[1,2,4]triazol-1-yl-butyl)-benzamide A solution of {2-[3-chloro-5-(cyclopentyl-(4-[1,2,4] triazol-1-yl-butyl)-carbamoyl)-phenoxy]-ethyl}-pyridin-4-yl-carbamic acid tert-butyl ester (0.069 g) and trifluoroacetic acid (0.5 ml) in dichloromethane (0.5 ml) was stirred at room temperature for 1 h then concentrated under vacuum. The residue was purified by flash chromatography eluting with dichloromethane:methanol:ammonia (92:8:1 v/v/v), to give the title compound as a white foam (0.026 g).

Mass spectrum: Found: MH$^+$ 483 ($^{35}$Cl); Hplc system 1 ($\lambda$=254 nm) Rt 6.9 min.

EXAMPLE 93

3-Chloro-N-(4-fluoro-phenyl)-5-[2-(pyridin-4-ylamino)-ethoxy]-N-(3-tetrazol-2-yl-propyl)-benzamide trifluoroacetate A suspension of 3-[2-(tert-butoxycarbonyl-pyridin-4-yl-amino)-ethoxy]-5-chloro-benzoic acid (0.05 g) 4-fluorophenyl-(3-tetrazol-2-yl-propyl)-amine (0.056 g) and EEDQ (0.05 g) in acetonitrile (1 ml) was stirred under nitrogen at room temperature for 18 h then at 50° C. for 2 h. The solvent was removed and the residue was purified by flash chromatography, eluting with dichloromethane:methanol:ammonia (99:1:0.1 v/v/v). The resultant oil was treated with trifluoroacetic acid then concentrated under vacuum to give the title compound as a colourless gum (0.004 g).

Mass spectrum: Found: MH$^+$ 496 ($^{35}$Cl); Hplc system 3 ($\lambda$=220–330 nm) Rt 3.6 min.

EXAMPLE 94

3-Chloro-N-(3-fluoro-phenyl)-5-[2-(pyridin-4-ylamino)-ethoxy]-N-(3-tetrazol-2-yl-propyl)-benzamide A solution of {2-[3-chloro-5-(3-fluorophenyl-(3-tetrazol-2-yl-propyl)-carbamoyl)-phenoxy]-ethyl}-pyridin-4-yl-carbamic acid tert-butyl ester (0.07 g) in trifluoroacetic acid (0.75 ml) and dichloromethane (0.75 ml) was stirred at room temperature for 1 h then concentrated under vacuum. The residue was purified by flash chromatography, eluting with dichloromethane/methanol/ammonia (90:10:1) to give the title compound as a white foam (0.042 g).

Mass spectrum: Found: MH$^+$ 496 ($^{35}$Cl); Hplc system 3 ($\lambda$=220–330 nm) Rt 3.5 min.

EXAMPLE 95

3-Chloro-N-(2-fluoro-phenyl)-5-[2-(pyridin-4-ylamino)-ethoxy]-N-(3-tetrazol-2-yl-propyl)-benzamide A solution of {2-[3-chloro-5-(2-fluorophenyl-(3-tetrazol-2-yl-propyl)-carbamoyl)-phenoxy]-ethyl}-pyridin-4-ylcarbamic acid tert-butyl ester (0.048 g) in trifluoroacetic acid (0.5 ml) and dichloromethane (0.5 ml) was stirred at room temperature for 1 h then concentrated under vacuum. The residue was purified by flash chromatography, eluting with dichloromethane:methanol:ammonia (95:5:0.5 then 90:10:1 v/v/v), to give the title compound as an off-white foam (0.035 g).

Mass spectrum: Found: MH$^+$ 496 ($^{35}$Cl); Hplc system 3 (λ=220–330 nm) Rt 3.5 min.

EXAMPLE 96

3-Chloro-N-phenyl-5-[2-(pyridin-4-ylamino)-ethoxy]-N-(2-tetrazol-2-yl-ethyl)-benzamide trifluoroacetate A solution of {2-[3-chloro-5-(phenyl-(3-tetrazol-2-yl-propyl)-carbamoyl)-phenoxy]-ethyl}-pyridin-4-yl-carbamic acid tert-butyl ester (0.024 g) in trifluoroacetic acid (0.25 ml) and dichloromethane (0.25 ml) was stirred at room temperature for 2 h then concentrated under vacuum, co-evaporating with dichloromethane to give the title compound as an off-white foam (0.026 g).

Mass spectrum: Found: MH$^+$ 464 ($^{35}$Cl); Hplc system 3 (λ=220–330 nm) Rt 3.5 min.

EXAMPLE 97

3-Chloro-N-phenyl-5-[2-(pyridin-4-ylamino)-ethoxy]-N-(2-[1,2,3]triazol-2-yl-ethyl)-benzamide trifluoroacetate A solution of {2-[3-chloro-5-(phenyl-(3-[1,2,3]-triazol-2-yl-propyl)-carbamoyl)-phenoxy]-ethyl}-pyridin-4-yl-carbamic acid tert-butyl ester (0.083 g) and trifluoroacetic acid (1 ml) in dichloromethane (1 ml) was stirred at room temperature for 2 h then concentrated under vacuum, co-evaporating with dichloromethane to give the title compound as a yellow-brown oil (0.103 g).

Mass spectrum: Found: MH$^+$ 463 ($^{35}$Cl); Hplc system 3 (λ=220–330 nm) Rt 3.6 min.

EXAMPLE 98

3-Chloro-N-phenyl-5-[2-(pyridin-4-ylamino)-ethoxy]-N-[2-(pyridin-2-yloxy)-ethyl]-benzamide bis(trifluoroacetate)

A solution of {2-[3-chloro-5-(phenyl-2-(pyridin-2-yloxy)-ethyl-carbamoyl)-phenoxy]-ethyl}-pyridin-4-yl-carbamic acid tert-butyl ester (0.065 g) and trifluoroacetic acid (0.75 ml) in dichloromethane (0.75 ml) was stirred at room temperature for 2 h then concentrated under vacuum, co-evaporating with dichloromethane to give the title compound as a yellow oil (0.086 g).

Mass spectrum: Found: MH$^+$ 489 ($^{35}$Cl); Hplc system 3 (λ=220–330 nm) Rt 3.8 min.

EXAMPLE 99

3-Chloro-N-isopropyl-N-(2-methoxy-ethyl)-5-[2-(pyridin-4-ylamino)-ethoxy]-benzamide A solution of {2-[3-chloro-5-(isopropyl-2-methoxy-ethyl-carbamoyl)-phenoxy]-ethyl}-pyridin-4-yl-carbamic acid tert-butyl ester (Intermediate SS8) (0.056 g) and trifluoro-acetic acid (0.6 ml) in dichloromethane (0.6 ml) was stirred at room temperature for 1 h then concentrated under vacuum. The residue was purified by flash chromatography eluting with dichloromethane:methanol:ammonia (94:6:1 then 92:8:1 v/v/v), to give the title compound as a colourless gum (0.036 g).

Mass spectrum: Found: MH$^+$ 392 ($^{35}$Cl); Hplc System 3 (λ=220–330 nm) Rt 3.5 min.

EXAMPLE 100

3-(Isopropyl-{3-methyl-5-[2-(pyridin-4-ylamino)-ethoxy]-benzoyl}-amino)-propionic acid methyl ester trifluoroacetate To a stirred solution of 3-methyl-5-[2-(pyridin-4-ylamino)-ethoxy]-benzoic acid trifluoroacetate (0.025 g) and TBTU (0.021 g) in DMF (1 ml) was added DIPEA (0.022 ml) followed by 3-isopropylamino-propionic acid methyl ester (0.01 g) after 3 min. The reaction was stirred at room temperature for 18 h, and then concentrated under reduced pressure. The residue was subjected to preparative hplc to give the title compound (0.031 g) as a colourless oil, by concentration of the required fraction under reduced pressure and drying by repetitive addition of acetonitrile and concentration under reduced pressure.

Hplc system 1 (λ=254 nm) Rt 6.8 min; $^1$H-NMR (CD$_3$OD, 250 MHz) δ 8.15 (d, 1H), 7.98 (d, 1H), 7.05 (m, 1H), 6.9 (m, 2H), 6.75 (m, 2H), 4.21 (t, 2H), 3.95 (m, 1H), 3.55–3.80 (m, 7H), 2.65 (t, 2H), 2.35 (s, 3H), 1.15 (d, 6H).

EXAMPLE 101

3-(Isopropyl-{3-methyl-5-[2-(pyridin-4-ylamino)-ethoxy]-benzoyl}-amino)-propionic acid trifluoroacetate To a solution of 3-(isopropyl-{3-methyl-5-[2-(pyridin-4-ylamino)-ethoxy]-benzoyl}-amino)-propionic acid methyl ester trifluoroacetate (0.031 g) in dioxan (1 ml) was added 2M aqueous sodium hydroxide (0.078 ml), and the resultant solution was stirred at room temperature for 3 h. 1M Aqueous hydrochloric acid (ca 0.5 ml) was added and the resultant solution was concentrated under reduced pressure. Th residue was subjected to preparative hplc and the title compound (0.027 g) was obtained as a colourless oil by concentration of the required fraction under reduced pressure and drying by repetitive addition of acetonitrile and concentration under reduced pressure.

Mass spectrum: Found: MH$^+$ 386; hplc system 1 (λ=254 nm) Rt 5.5 min.

EXAMPLE 102

6-({3-Methyl-5-[2-(pyridin-4-ylamino)-ethoxy]-benzoyl}-isopropyl-amino)-hexanoic acid trifluoroacetate P-Benzyloxybenzylalcohol (Wang) resin[10] (0.54 mmol/g, 0.250 g) was wetted with DMF (ca. 2 ml) and then treated with a mixture of 6-bromohexanoic acid (0.173 g), diisopropylcarbodiimide (0.139 ml) and 4-dimethylaminopyridine (2 mg) in dry DMF (1 ml). The mixture was agitated for 5 days and then filtered dry under suction. The resin was repeatedly washed with DMF (×3), and dichloromethane (×3) before drying under suction. The resin was then agitated with isopropylamine (1.5 ml) in dry DMF (1.5 ml) for 2 days. After filtration, the resin was repeatedly washed with DMF (×3) and dichloromethane (×3). The resin was then agitated with 3-methyl-5-[2-(pyridin-4-ylamino)-ethoxy]-benzoic acid (0.16 g), diisopropylcarbodiimide (0.127 ml) and

EXAMPLE 103

N-tert-Butyl-N-(2-tert-butylcarbamoyl-ethyl)-3-chloro-5-[2-(pyridin-4-ylamino)-ethoxy]-benzamide trifluoroacetate A suspension of 5% Pd on carbon (0.020 g) in a solution of (2-{3-[tert-butyl-(2-tert-butylcarbamoyl-ethyl)-carbamoyl]-5-chloro-phenoxy}-ethyl)-pyridin-4-yl-carbamic acid benzyl ester (0.024 g) in 1,4-dioxan (5 ml) was stirred under an atmosphere of hydrogen for 20 h. The catalyst was removed by filtration and the filtrate evaporated in vacuo. The residue was subjected to preparative hplc to give the title compound (0.003 g) as a colourless gum.

Hplc system 1 ($\lambda$=254 nm) Rt 8.2 min; Mass spectrum: Found: MH$^+$ 475.2478 $C_{25}H_{36}{}^{35}Cl_1N_4O_3$ requires 475.2476.

EXAMPLE 104

N-(2-tert-Butylcarbamoyl-ethyl)-3-chloro-N-cyclobutyl-5-[2-(pyridin-4-ylamino)-ethoxy]-benzamide trifluoroacetate A solution of (2-{3-[(2-tert-butylcarbamoyl-ethyl)-cyclobutyl-carbamoyl]-5-chloro-phenoxy}-ethyl)-pyridin-4-yl-carbamic acid tert-butyl ester (0.021 g) in a mixture of dichloromethane (1 ml) and trifluoroacetic acid (1 ml) was stored at room temperature for 64 h and then concentrated under reduced pressure to give the title compound (0.020 g) as a colourless gum.

Hplc system 1 ($\lambda$=254 nm) Rt 7.6 min; Mass spectrum: Found: MH$^+$ 473.2332 $C_{25}H_{34}{}^{35}Cl_1N_4O_3$ requires 473.2319.

EXAMPLE 105

3-Chloro-N-cyclobutyl-N-[2-(2,2-dimethyl-propylcarbamoyl)-ethyl]-5-[2-(pyridin-4-ylamino)-ethoxy]-benzamide trifluoroacetate A solution of [2-(3-chloro-5-{cyclobutyl-[2-(2,2-dimethyl-propylcarbamoyl)-ethyl]-carbamoyl}-phenoxy)-ethyl]-pyridin-4-yl carbamic acid tert-butyl ester (0.016 g) in a mixture of dichloromethane (1 ml) and trifluoroacetic acid (1 ml) was stored at room temperature for 64 h and then concentrated under reduced pressure to give the title compound (0.012 g) as a colourless gum.

Hplc system 1 ($\lambda$=254 nm) Rt 8.1 min; Mass spectrum: Found: MH$^+$ 487.2462 $C_{26}H_{36}{}^{35}Cl_1N_4O_3$ requires 487.2476.

EXAMPLE 106

N-(2-Carbamoyl-ethyl)-3-chloro-N-cyclobutyl-5-[2-(pyridin-4-ylamino)-ethoxy]-benzamide trifluoroacetate A solution of (2-{3-chloro-5-[(2-cyano-ethyl)-cyclobutyl-carbamoyl]-phenoxy}-ethyl)-pyridin-4-yl-carbamic acid tert-butyl ester (0.042 g) and water (0.050 ml) in mixture of trifluoroacetic acid (1 ml) and dichloromethane (1 ml) was stored at room temperature for 24 h and then the solvent removed under reduced pressure. The residue was subjected to preparative hplc to give the title compound (0.027 g) as a colourless gum by concentration of the required fraction under reduced pressure and drying by repetitive addition of acetonitrile and concentration under reduced pressure.

Hplc system 1 ($\lambda$=254 nm) Rt 5.6 min; Mass spectrum: Found: MH$^+$ 417.

EXAMPLE 107

3-Chloro-N-isopropyl-5-[2-(pyridin-4-ylamino)-ethoxy]-N-(2-sulfamoyl-ethyl)-benzamide trifluoroacetate A solution of (2-{3-chloro-5-[isopropyl-(2-sulfamoyl-ethyl)-carbamoyl]-phenoxy}-ethyl)-pyridin-4-yl-carbamic acid tert-butyl ester (0.012 g) in a mixture of dichloromethane (1 ml) and trifluoroacetic acid (1 ml) was stored at room temperature for 64 h and then concentrated under reduced pressure to give the title compound (0.011 g) as a colourless gum.

Hplc system 1 ($\lambda$=254 nm) Rt 5.6 min; Mass spectrum: Found: MH$^+$ 441.

EXAMPLE 108

3-Chloro-N-(2,2-dimethyl-propylsulfamoyl-ethyl)-N-isopropyl-5-[2-(pyridin-4-ylamino)-ethoxy]-benzamide trifluoroacetate A solution of [2-(3-chloro-5-{[2-(2,2-dimethyl-propylsulfamoyl)-ethyl]-isopropyl-carbamoyl}-phenoxy)-ethyl]-pyridin-4-yl-carbamic acid tert-butyl ester (0.042 g) in a mixture of dichloromethane (1 ml) and trifluoroacetic acid (1 ml) was stored at room temperature for 64 h and then concentrated under reduced pressure to give the title compound (0.024 g) as a straw coloured gum.

Hplc system 1 ($\lambda$=254 nm) Rt 8.7 min; Mass spectrum: Found: MH$^+$ 511.2143 $C_{22}H_{35}{}^{35}Cl_1N_4O_4S_1$ requires 511.2146.

EXAMPLE 109

3-Chloro-N-{2-(5-hydroxy-[1,2,4]oxadiazol-3-yl)-ethyl}-N-isopropyl-5-[2[(pyridin-4-ylamino)-ethoxy]-benzamide trifluoroacetate A solution of (3-chloro-N-{2-(5-hydroxy-[1,2,4]oxadiazol-3-yl)-ethyl}-N-isopropyl-5-[2[(pyridin-4-ylamino)-ethoxy]-benzamide carbamic acid tert-butyl ester (0.046 g) in a mixture of DCM (3 ml) and trifluoroacetic acid (1 ml) was stirred at room temperature for 3 h. The solvent was evaporated under pressure and the residue subjected to preparative hplc to give the title compound (0.027 g) as a clear oil.

Mass spectrum: Found: MH$^+$ 446 ($^{35}$Cl); Hplc system 1 ($\lambda$=254 nm) Rt 6.16 min.

EXAMPLE 110

N-(2-tert-Butylcarbamoyl-ethyl)-N-isopropyl-3-methyl-5-[2-(pyridin-4-ylamino)-ethoxy]-benzamide trifluoroacetate To a stirred solution of 3-(isopropyl-{3-methyl-5-[2-(pyridin-4-ylamino)-ethoxy]-benzoyl}-amino)-propionic

---

4-dimethylaminopyridine (0.012 g) for 3 days. After the excess reagents were removed by filtration, the resin was washed with DMF (×3) and dichloromethane (×3) before treatment with dichloromethane (1 ml) and trifluoroacetic acid (1 ml). After 1.5 h, the resin was filtered and washed thoroughly with dichloromethane. The combined filtrate and washings were evaporated to dryness under reduced pressure and subjected to preparative hplc. Evaporation of the required fraction gave the title compound as a gum (0.048 g).

Hplc system 1 ($\lambda$=254 nm) Rt 6.7 min; p-Benzyloxybenzyl alcohol resin—polymer matrix is copoly (styrene-1% divinylbenzene), 100–200 mesh; Novabiochem cat. no. 01-64-0014; Mass Spectrum: Found: MH$^+$ 428.

acid trifluoroacetate (0.018 g) and PyBroP® (0.017 g) in DMF (1 ml) was added DIPEA (0.012 ml) followed by tert-butylamine (0.005 ml), after 1 min. The reaction mixture was stirred at room temperature for 18 h, and then concentrated under reduced pressure. The residue was subjected to preparative hplc and the title compound (0.009 g) was obtained as a colourless oil by concentration of the required fraction under reduced pressure and drying by repetitive addition of acetonitrile and concentration under reduced pressure.

Hplc system 3 ($\lambda$=220–330 nm) Rt 3.8 min; Mass spectrum: Found: MH$^+$ 441.

Similarly prepared was:

EXAMPLE 111

N-{2-(2,2-dimethylpropylcarbamoyl)-ethyl}-N-isopropyl-3-methyl-5-[2-(pyridin-4-ylamino)-ethoxy]-benzamide Hplc system 3 ($\lambda$=220–330 nm) Rt 4.1 min; Mass spectrum: Found: MH$^+$ 455.

EXAMPLE 112

N-(5-tert-Butylcarbamoyl-pentyl)-3-chloro-N-isopropyl-5-[2-(pyridin-4-ylamino)-ethoxy]-benzamide trifluoroacetate To a stirred solution of 6-({3-chloro-5-[2-(pyridin-4-ylamino)-ethoxy]-benzoyl}-isopropyl-amino)-hexanoic acid trifluoroacetate (0.02 g) and PyBroP® (0.021 g) in DMF (1 ml) was added DIPEA (0.016 ml) followed by tert-butylamine (0.005 ml), after 1 min. The reaction mixture was stirred at room temperature for 18 h, and then concentrated under reduced pressure. The residue was subjected to preparative hplc and the title compound (0.0094 g) was obtained as a colourless oil by concentration of the required fraction under reduced pressure and drying by repetitive addition of acetonitrile and concentration under reduced pressure.

Hplc system 1 ($\lambda$=254 nm) Rt 8.3 min; Mass spectrum: Found: MH$^+$ 503.

Similarly prepared was:

EXAMPLE 113

3-Chloro-N-[5-(2,2-dimethyl-propylcarbamoyl)-pentyl]-N-isopropyl-5-[2-(pyridin-4-ylamino)-ethoxy]-benzamide trifluoroacetate Hplc system 1 ($\lambda$=254 nm) Rt 8.7 min; Mass spectrum: Found: MH$^+$ 517.

EXAMPLE 114

N-[5-tert-Butylcarbamoyl)-pentyl]-N-isopropyl-3-methyl-5-[2-(pyridin-4-ylamino)-ethoxy]-benzamide trifluoroacetate)

To a stirred solution of 6-[{3-methyl-5-[2-(pyridin-4-ylamino)-ethoxy]-benzoyl}-(isopropyl)-amino]-hexanoic acid trifluoroacetate (0.026 g) and PyBroP® (0.022 g) in DMF (1 ml) was added DIPEA (0.018 ml) followed by tert-butylamine (0.005 ml), after 1 min. The reaction mixture was stirred at room temperature for 18 h, and then concentrated under reduced pressure. The residue was subjected to preparative hplc and the title compound (0.002 g) was obtained as a colourless oil by concentration of the required fraction under reduced pressure and drying by repetitive addition of acetonitrile and concentration under reduced pressure.

Hplc system 1 ($\lambda$=254 nm) Rt 8.2 min; Mass spectrum: Found: MH$^+$ 483.

EXAMPLE 115

N-(5-Carbamoyl-pentyl)-N-isopropyl-3-methyl-5-[2-(pyridin-4ylamino)-ethoxy]-benzamide trifluoroacetate To a solution of 6-[{3-methyl-5-[2-(pyridin-4-ylamino)-ethoxy]-benzoyl}-(isopropyl)-amino]-hexanoic acid trifluoroacetate (0.022 g) in DMF (1 ml) was added HATU® (0.039 g), DIPEA (0.018 ml) and 0.5M ammonia in 1,4-dioxane solution (0.2 ml). The mixture was stirred overnight. The reaction mixture was evaporated under reduced pressure, the residue obtained was subjected to preparative hplc to give the title compound as a colourless oil (0.008 g).

Hplc system 1 ($\lambda$=254 nm) Rt 5.9 min; Mass spectrum: Found: MH$^+$ 427.

EXAMPLE 116

3-Chloro-N-(2-(4-tert-butylphenyl)-ethyl)-N-isopropyl-5-[2-(pyridin-4-ylamino)-ethoxy]-benzamide A solution of {2-[3-chloro-5-(isopropyl-(2-(4-tert-butylphenyl)-ethyl-carbamoyl)-phenoxy]-ethyl}-pyridin-4-yl-carbamic acid tert-butyl ester (0.062 g) in trifluoroacetic acid (0.75 ml) and dichloromethane (0.75 ml) was stirred at room temperature for 1 h then concentrated under vacuum. The residue was purified by flash chromatograpy, eluting with dichloromethane:methanol:ammonia(0.88) (94:6:1 v/v/v) to give the title compound as a pale yellow gum (0.033 g).

Mass Spectrum: Found: MH$^+$ 494 ($^{35}$Cl); Hplc System 3 ($\lambda$=220–330 nm) Rt 4.4 min.

Example 117

2-[{3-Chloro-5-[2-(pyridin-4-ylamino)-ethoxy]-benzoyl}-(2,4-difluoro-benzyl)-amino]-butyric acid trifluoroacetate p-Benzyloxybenzylalcohol resin[10] (0.54 mmol/g; 0.253 g) was wetted with DMF and then treated with a mixture of 2-(9H-fluoren-9-ylmethoxycarbonylamino)-butyric acid (0.221 g) and diisopropylcarbodiimide (0.107 ml) in dry DMF (1 ml). The mixture was agitated for 26 h and then filtered dry under suction. The resin was repeatedly washed with DMF (×3), dichloromethane (×3), and diethyl ether (×3) before drying under suction. The resin was then agitated with a 20% v/v solution of piperidine in DMF (2 ml) for 1.3 h. After filtration the resin was repeatedly washed with DMF (×3) and dichloromethane (×3). Trimethylorthoformate (0.3 ml), 2,4-difluorobenzaldehyde (0.3 ml), and dichloromethane (0.9 ml) were added and the mixture agitated for 4 days. The resin was filtered dry and washed with dichloromethane (×3) then a solution of tetramethylammonium triacetoxyborohydride (0.14 g) and glacial acetic acid (0.03 ml) in dichloromethane (1 ml) was added. The resin was agitated for 2 days, filtered dry, washed with dichloromethane (×3) and DMF (×3) and a solution of 3-[2-(tert-butoxycarbonyl-pyridin-4-yl-amino)-ethoxy]-5-chloro-benzoic acid (0.106 g), diisopropylcarbodiimide (0.046 ml), and 4-(N,N-dimethylamino)pyridine (trace) in DMF (0.75 ml) was added. After agitating for 19 h excess reagents were removed by filtration and the resin was washed with DMF (×3) and dichloromethane (×3) before treatment with dichloromethane (0.5 ml) and 95:5 v/v trifluoroacetic acid and water (2 ml). After 2 h the resin was filtered and washed thoroughly with dichloromethane. The combined filtrate and washings were evaporated to dryness under reduced pressure and subjected to preparative hplc. Evaporation of the required fraction gave the title compound as a pale cream foam (0.021 g).

Hplc system 1 ($\lambda$=254 nm) Rt 8.4 min; Mass spectrum: Found: MH$^+$ 504.1485 $C_{25}H_{24}{}^{35}ClF_2N_3O_4$ requires 504.1502.

EXAMPLE 118

4-[({3-Chloro-5-[2-(pyridin-4-ylamino)-ethoxy]-benzoyl}-isobutyl-amino)-methyl]-benzoic acid trifluoroacetate p-Benzyloxybenzylalcohol resin[10] (0.54 mmol/g; 0.25 g) was wetted with DMF and then treated with a solution of 4-(chloromethyl)benzoic acid (0.23 g) and diisopropylcarbodiimide (0.106 ml) in DMF (1 ml. The mixture was agitated overnight and the resin filtered and washed with DMF (×2) before repeating the entire coupling procedure. The resin was washed with DMF (×6) and then treated with isobutylamine (0.2 ml) in DMF (0.5 ml) together with a trace of sodium iodide. After agitating for 3 days the resin was filtered and washed with DMF (×3) and the amine reaction repeated this time overnight. The resin was then filtered dry, washed with DMF (×6), dichloromethane (×6) and diethyl ether (×2) and dried by suction. After wetting the resin with DMF it was treated with 3-[2-tert-butoxycarbonyl-pyridin-4-yl-amino)-ethoxy]-5-chloro-benzoic acid (0.053 g), diisopropylcarbodiimide (0.021 ml), and 4-N,N-dimethylamino) pyridine (trace) in DMF (0.5 ml). After agitating for 24 h the resin was filtered and washed with DMF (×6) and the coupling procedure repeated. The resin was then filtered and washed with DMF (×6), dichloromethane (×6) and diethyl ether (×2) before drying by suction. The resin was treated with a 1:1 v/v mixture of trifluoroacetic acid and dichloromethane (2 ml) with agitation for 80 min. The resin was filtered and washed with more of the trifluoroacetic acid mixture and then dichloromethane. The combined filtrate and washings were evaporated to dryness under reduced pressue and subjected to preparative hplc. The title compound was obtained as a colourless gum (0.019 g).

Hplc system 3 ($\lambda$=220–330 nm) Rt 4.2 min; Mass spectrum: Found: MH$^+$ 482.1864 $C_{26}H_{29}{}^{35}ClN_3O_4$ requires 482.1847.

EXAMPLE 119

4-[2-({3-Chloro-5-[2-(pyridin-4-ylamino)-ethoxy]-benzoyl}-isobutyl-amino)-ethyl]-benzoic acid trifluoroacetate p-Benzyloxybenzylalcohol resin[10] (0.54 mmol/g; 0.25 g) was wetted with DMF and then treated with a solution of 4-(2-chloroethyl)benzoic acid (0.25 g), diisopropyicarbodiimide (0.106 ml) and 4-(N,N-dimethylamino)pyridine (trace) in DMF (1 ml). The mixture was agitated overnight and the resin filtered and washed with DMF (×2) before repeating the entire coupling procedure. The resin was filtered and washed with DMF (×6) and then treated with isobutylamine (1 ml, DMF (0.7 ml) and sodium iodide (0.1 g) and the resin shaken and subjected to sonication alternately for 35 min. The resin was then agitated for 3 days and then filtered and washed with DMF (×6), dichloromethane (×6) and diethyl ether (×2) before drying by suction. After wetting the resin with DMF it was treated with 3-[2-(tert-butoxycarbonyl-pyridin-4-yl-amino)-ethoxy]-5-chloro-benzoic acid (0.053 g), diisopropylcarbodiimide (0.021 ml), and 4-(N,N-dimethylamino)pyridine (trace) in DMF (0.5 ml). After agitating for 24 h the resin was filtered and washed with DMF (×6) and the coupling procedure repeated. The resin was then filtered and washed with DMF (×6), dichloromethane (×6) and diethyl ether (×2) before drying by suction. The resin was then treated with a 1:1 v/v mixture of trifluoroacetic acid and dichloromethane (2 ml) with agitation for 1.25 h. The resin was filtered and washed with more of the trifluoroacetic acid mixture and then dichloromethane. The combined filtrate and washings were evaporated to dryness under reduced pressure and subjected to preparative hplc and the title compound was obtained as a clear brown-tinged oil (0.012 g).

Hplc system 1 ($\lambda$=254 nm) Rt 8.5 min; Mass spectrum: Found: MH$^+$ 496.1990 $C_{27}H_{31}{}^{35}ClN_3O_4$ requires 496.2003.

EXAMPLE 120

6-[{3-Chloro-5-[2-(pyridin-4-ylamino)-ethoxy]-benzoyl}-(2-fluoro-benzyl)-amino]-hexanoic acid trifluoroacetate p-Benzyloxybenzylalcohol resin[10] (0.54 mmol/g, 0.250 g) was wetted with DMF (ca. 2 ml) and then treated with a mixture of 6-bromohexanoic acid (0.173 g), diisopropylcarbodiimide (0.139 ml) and 4-(N,N-dimethylaminopyridine (0.02 g) in dry DMF (1 ml). The mixture was agitated for 5 days and then filtered dry under suction. The resin was repeatedly washed with DMF (×3), and dichloromethane (×3) before drying under suction. The resin was then agitated with 2-fluorobenzylamine (1.5 ml) in dry DMF (1.5 ml) for 2 days. After filtration, the resin was repeatedly washed with DMF (×3) and dichloromethane (×3). The resin was then agitated with 3-[2-(tert-butoxycarbonyl-pyridin-4-yl-amino)-ethoxy]-5-chloro-benzoic acid (0.16 g), diisopropylcarbodiimide (0.127 ml) and 4-dimethylaminopyridine (0.012 g) for 3 days. After the excess reagents were removed by filtration, the resin was washed with DMF (×3) and dichloromethane (×3) before treatment with dichloromethane (1 ml) and trifluoroacetic acid (1 ml). After 1.5 h, the resin was filtered and washed thoroughly with dichloromethane. The combined filtrate and washings were evaporated to dryness under reduced pressure and subjected to preparative hplc. Evaporation of the required fraction gave the title compound as a gum (0.0082 g).

Hplc system 1 ($\lambda$=254 nm) Rt 8.0 min; Mass spectrum: Found: MH$^+$ 514 ($^{35}$Cl).

Similarly prepared, using commercially available amines, were:

EXAMPLE 121

6-[{3-Chloro-5-[2-(pyridin-4-ylamino)-ethoxy]-benzoyl}-(3-fuoro-benzyl)-amino]-hexanoic acid trifluoroacetate Hplc system 1 ($\lambda$=254 nm) Rt 8.0 min; Mass spectrum: Found: MH$^+$ 514 ($^{35}$Cl).

EXAMPLE 122

6-[{3-Chloro-5-[2-(pyridin-4-ylamino)-ethoxy]-benzoyl}-(2-methoxy-ethyl)-amino]-hexanoic acid trifluoroacetate Hplc system 1 ($\lambda$=254 nm) Rt 5.9 min; Mass spectrum: Found: MH$^+$ 464 ($^{35}$Cl).

EXAMPLE 123

6-({3-Chloro-5-[2-(pyridin-4-ylamino)-ethoxy]-benzoyl}-pyridin-4-ylmethyl-amino)-hexanoic acid trifluoroacetate Hplc system 1 ($\lambda$=254 nm) Rt 4.4 min; Mass spectrum: Found: MH$^+$ 496 ($^{35}$Cl).

EXAMPLE 124

6-({3-Chloro-5-[2-(pyridin-4-ylamino)-ethoxy]-benzoyl}-cyclohexylmethyl-amino)-hexanoic acid trifluoroacetate Hplc system 1 ($\lambda$=254 nm) Rt 8.9 min; Mass spectrum: Found: MH$^+$ 502 ($^{35}$Cl).

EXAMPLE 125

6-({3-Chloro-5-[2-(pyridin-4-ylamino)-ethoxy]-benzoyl}-isobutyl-amino)-hexanoic acid trifluoroacetate Hplc system 1 ($\lambda$=254 nm) Rt 7.5 min; Mass spectrum: Found: MH$^+$ 462 ($^{35}$Cl).

EXAMPLE 126

6-({3-Chloro-5-[2-(pyridin-4-ylamino)-ethoxy]-benzoyl}-thiophen-2-ylmethyl-amino)-hexanoic acid trifluoroacetate Hplc system 3 ($\lambda$=220–330 nm) Rt 3.75 min; Mass spectrum: Found: MH$^+$ 501 ($^{35}$Cl).

EXAMPLE 127

6-({3-Chloro-5-[2-(pyridin-4-ylamino)-ethoxy]-benzoyl}-(2-methyl-butyl)-amino)-hexanoic acid trifluoroacetate Hplc system 3 ($\lambda$=220–330 nm) Rt 3.8 min; Mass spectrum: Found: MH$^+$ 476 ($^{35}$Cl).

EXAMPLE 128

4-({3-Chloro-5-[2-(pyridin-4-ylamino)-ethoxy]-benzol}-cyclobutyl-amino)-butyric acid trifluoroacetate p-Benzyloxybenzylalcohol resin[10] (0.54 mmol/g, 0.250 g) was wetted with DMF (ca. 2 ml) and then treated with a mixture of 4-bromobutanoic acid (0.112 g), diisopropylcarbodiimide (0.139 ml) and 4-N,N-dimethylaminopyridine) (0.02 g) in dry DMF (1 ml). The mixture was agitated for 2 days and then filtered dry under suction. The resin was repeatedly washed with DMF (×3), and dichloromethane (×3) before drying under suction. The resin was then agitated with cyclobutylamine (1.5 ml) in dry DMF (1.5 ml) for 1 day. After filtration, the resin was repeatedly washed with DMF (×3) and dichloromethane (×3). The resin was then agitated with 3-[2-(tert-butoxycarbonyl-pyridin-4-ylamino)-ethoxy]-5-chloro-benzoic acid (0.16 g), diisopropylcarbodiimide (0.127 ml) and 4-N,N-dimethylaminopyridine) (0.012 g) for 3 days. After the excess reagents were removed by filtration, the resin was washed with DMF (×3) and dichloromethane (×3) before treatment with dichloromethane (1 ml) and trifluoroacetic acid (1 ml). After 1.5 h, the resin was filtered and washed thoroughly with dichloromethane. The combined filtrate and washings were evaporated to dryness under reduced pressure and subjected to preparative hplc. Evaporation of the required fraction gave the title compound as a gum (0.0152 g).

Hplc system 1 ($\lambda$=254 nm) Rt 6.6 min; Mass spectrum: Found: MH$^+$ 432 ($^{35}$Cl).

Similarly prepared, using commercially available amines, were:

EXAMPLE 129

4-[{3-Chloro-5-[2-(pyridin-4-ylamino)-ethoxy]-benzoyl}-(3-fluoro-benzyl)-amino]-butyric acid trifluoroacetate Hplc system 1 ($\lambda$=254 nm) Rt 7.6 min; Mass spectrum: Found: MH$^+$ 486 ($^{35}$Cl)

EXAMPLE 130

4-({3-Chloro-5-[2-(pyridin-4-ylamino)-ethoxy]-benzoyl}-furan-2-ylmethyl-amino)-butyric acid trifluoroacetate Hplc system 1 ($\lambda$=254 nm) Rt 6.7 min; Mass spectrum: Found: MH$^+$ 458 ($^{35}$Cl).

EXAMPLE 131

4-[{3-Chloro-5-[2-(pyridin-4-ylamino)-ethoxy]-benzoyl}-(1-methyl-1H-benzoimidazol-2-yl)-amino]-butyric acid trifluoroacetate Hplc system 3 ($\lambda$=220–330 nm) Rt 3.8 min; Mass spectrum: Found: MH$^+$ 508 ($^{35}$Cl).

EXAMPLE 132

4-[{3-Chloro-5-[2-(pyridin-4-ylamino)-ethoxy]-benzoyl}-naphthalen-1-ylmethyl-amino)-butyric acid trifluoroacetate Hplc system 3 ($\lambda$=220–330 nm) Rt 4.2 min; Mass spectrum: Found: MH$^+$ 518 ($^{35}$Cl).

EXAMPLE 133

N-(5-Carbamoyl-pentyl)-3-chloro-N-(2-fluoro-benzyl)-5-[2-(pyridin-4-ylamino)-ethoxy]-benzamide trifluoroacetate Rink amide resin[11] (0.45 mmol/g, 0.250 g) was treated with piperidine (20% in DMF) and agitated for 30 min and then filtered dry under suction. The resin was repeatedly washed with DMF (×3) and dichloromethane (×3) before drying under suction. The resin was then treated with a mixture of 6-bromohexanoic add (0.11 g), diisopropylcarbodiimide (0.11 ml and 4-(N,N-dimethylaminopyridine) (0.02 g) in dry DMF (2 ml). The mixture was agitated for 24 h and then filtered dry under suction. The resin was repeatedly washed with DMF (×3), and dichloromethane (×3) before drying under suction. The resin was then agitated with 2-fluorobenzylamine (1.5 ml) in dry DMF (1.5 ml) for 3 days. After filtration, the resin was repeatedly washed with DMF (×3) and dichloromethane (×3). The resin was then agitated with 3-[2-(tert-butoxycarbonyl-pyridin-4-ylamino)-ethoxy]-5-chloro-benzoic acid (0.16 g), diisopropylcarbodiimide (0.127 ml) and 4-(N,N-dimethylaminopyridine) (0.012 g) for 3 days. After the excess reagents were removed by filtration, the resin was washed with DMF (×3) and dichloromethane (×3) before treatment with dichloromethane (2 ml) and trifluoroacetic acid (0.2 ml). After 1.5 h, the resin was filtered and washed thoroughly with dichloromethane. The combined filtrate and washings were evaporated to dryness under reduced pressure. The residue was dissolved in a mixture of dichloromethane (2 ml) and trifluoroacetic acid (1 ml) and stirred at room temperature for 2 h, after which the solution was evaporated to dryness under reduced pressure and subjected to preparative hplc. Evaporation of the required fraction gave the title compound as a gum (0.024 g).

Hplc system 1 ($\lambda$=254 nm) Rt 7.35 min; Mass spectrum: Found: MH$^+$ 513 ($^{35}$Cl).

Similarly prepared, using commercially available amines, were:

EXAMPLE 134

N-(5-Carbamoyl-pentyl)-3-chloro-5-[2-(pyridin-4-ylamino)-ethoxy]-N-(2,2,2-trifluoroethyl)-benzamide trifluoroacetate Hplc system 1 ($\lambda$=254 nm) Rt 6.9 min; Mass spectrum: Found: MH$^+$ 487 ($^{35}$Cl).

EXAMPLE 135

N-(5-Carbamoyl-pentyl)-3-chloro-N-(2-methoxy-ethyl)-5-[2-(pyridin-4-ylamino)-ethoxy]-benzamide trifluoroacetate Hplc -system 1 ($\lambda$=254 nm) Rt 5.4 min; Mass spectrum: Found: MH 463 ($^{35}$Cl).

EXAMPLE 136

N-(5-Carbamoyl-pentyl)-3-chloro-N-cyclohexylmethyl-5-[2-(pyridin-4-ylamino)-ethoxy]-benzamide trifluoroacetate Hplc system 3 ($\lambda$=220–330 nm) Rt 4.1 min; Mass spectrum: Found: MH$^+$ 501 ($^{35}$Cl).

EXAMPLE 137

N-(5-Carbamoyl-pentyl)-3-chloro-N-isobutyl-5-[2-(pyridin-4-ylamino)-ethoxy]-benzamide trifluoroacetate Hplc system 3 ($\lambda$=220–330 nm) Rt 3.8 min; Mass spectrum: Found: MH$^+$ 461 ($^{35}$Cl).

EXAMPLE 138

N-(5-Carbamoyl-pentyl)-3-chloro-N-furan-2-ylmethyl-5-[2-(pyridin-4-ylamino)-ethoxy]-benzamide trifluoroacetate Hplc system 1 ($\lambda$=254 nm) Rt 6.4 min; Mass spec-rum: Found: MH$^+$ 485 ($^{35}$Cl).

EXAMPLE 139

N-(5-Carbamoyl-pentyl)-3-chloro-5-[2-(pyridin-4-ylamino)-ethoxy]-N-thiophen-2-ylmethyl-benzamide trifluoroacetate Hplc system 3 ($\lambda$=220–330 nm) Rt 3.9 min; Mass spectrum: Found: MH$^+$ 501 ($^{35}$Cl).

EXAMPLE 140

6-({3-Chloro-5-[2-(pyridin-4-ylamino)-ethoxy]-benzoyl}-isopropyl-amino)-hexanoic acid trifluoroacetate Hplc system 1 ($\lambda$=254 nm) Rt 7.0 min; Mass spectrum: Found: MH$^+$ 448 ($^{35}$Cl).

EXAMPLE 141

3-Chloro-N-isopropyl-5-[2-(pyridin-4-ylamino)-ethoxy]-N-[2-(pyridin-2-yloxy)-ethyl]-benzamide)

A solution of {2-[3-chloro-5-(isopropyl-2-(pyridin-2-yloxy)-ethyl-carbamoyl)-phenoxy]-ethyl}-pyridin-4-yl-carbamic acid tert-butyl ester (0.033 g) and TFA (0.4 ml) in dichloromethane (0.4 ml) was stirred at room temp for 3 h then concentrated under vacuum. The residue was purified by flash chromatography on silica eluting with dichloromethane/methanol/ammonia (94:6:1) to give the title compound as a colourless gum (0.005 g).

Mass spectrum: Found: MH$^+$ 455 ($^{35}$Cl); Hplc system 3 ($\lambda$=220–330 nm) Rt 3.8 min.

EXAMPLE 142

3-Chloro-N,N-diisorropyl-5-[2-(pyridin-4-ylamino)-ethoxy]-benzamide trifluoroacetate {2-[3-Chloro-5-(diisopropylcarbamoyl)-phenoxy[-ethyl}-pyridin-4-yl-carbamic acid tert-butyl ester (0.073 g) was treated with dichloromethane (2 ml) containing trifluoroacetic acid (1 ml). After 2 h the excess solvents and reagents were evaporated at reduced pressure to give the title compound as a colourless gum (0.08 g).

Mass spectrum: Found: MH$^+$ 376.1799 $C_{20}H_{27}{}^{35}ClN_3O_2$ requires 376.1791; Hplc system 1 ($\lambda$=254 nm) Rt 8.2 min.

References

[1] Brown, P. M.; Thomson, R. H. *J.Chem.Soc., Perkin Trans. 1*, 1976, 997
[2] Kelly, T. A.; McNeil, D. W. *Tetrahedron Lett.*, 1994, 900
[3] Becker A. M.; Rickards R. W; Brown R. F. C. *Tetrahedron*, 1983, 4189
[4] U.S. Pat. No. 4,016,267.
[5] S. Dragon et al., Makromol. Chem., 1986, 187(1), 9–22.
[6] Japanese patent 60156659.
[7] J. Chem. Soc., Perkin Trans. 2. 1987, (12), 1789.
[8] U.S. Pat. No. 5,334,745.
[9] Japanese patent 60156659.
[10] p-Benzyloxybenzyl alcohol resin-polymer matrix is copoly(styrene-1% divinylbenzene), 100–200 mesh; Novabiochem cat. no. 01-64-0014
[11] Rink amide resin-polymer matrix is copoly(styrene-1% divinylbenzene), 100–200 mesh; Novabiochem cat. no. 01-64-0013

Compounds of formula (I) have been included in pharmacy formulations, and details of such formulations are given below.

TABLETS FOR ORAL ADMINISTRATION

A. Direct Compression

|  | % w/w |
| --- | --- |
| Active ingredient | 32.7 |
| Anhydrous lactose | 36.8 |
| Microcrystalline cellulose | 25.0 |
| Pregelatinised maize starch | 5.0 |
| Magnesium stearate | 0.5 |

The active ingredient was sieved and blended with the excipients. The resultant mix was compressed into tablets using a tablet machine fitted with suitable diameter punches.

A rotary machine may also be us ed for tabletting.

Tablets of various strengths may be prepared by for example altering the ratio of active ingredient to lactose or the compression weight and using punches to suit.

B. Wet Granulation

Formulation (i)

|  | % w/w |
|---|---|
| Active ingredient | 3.5 |
| Lactose | 73.25 |
| Starch | 15.0 |
| Pregelatinised maize starch | 7.5 |
| Magnesium stearate | 0.75 |

The active ingredient was sieved through a suitable sieve and blended with lactose, starch and pregelatinised maize starch. Suitable volumes of purified water were added and the powders were granulated. After drying, the granules were screened and blended with the magnesium stearate. The granules were then compressed into tablets using suitable diameter punches. The water used for granlation does not appear in the final product.

A rotary machine may also be used for tabletting.

Tablets of various strengths may be prepared by for example altering the ratio of active ingredient to lactose or the compression weight and using punches to suit.

Formulation (ii)

|  | % w/w |
|---|---|
| Active ingredient/lactose granule* | 93.0 |
| Microcrystalline cellulose | 5.5 |
| Crosscarmellose sodium | 1.0 |
| Magnesium stearate | 0.5 |
| * Active ingredient/lactose granule | |
| Active ingredient | 50.0 |
| Lactose | 50.0 |
| Purified water | qs+ |

+The water does not appear in the final product. Typical range 100–140 g per kg of blend.

The active ingredient and lactose were mixed together and granulated by the addition of purified water. The granules obtained after mixing were dried and passed through a screen, and the resulting granules were then mixed with the other tablet core excipients. The mix is compressed into tablets.

A rotary machine may also be used for tabletting.

Tablets of various strengths may be prepared by for example altering the ratio of active ingredient to lactose or the compression weight and using punches to suit.

The tablets may be film coated with suitable film-forming materials such as hydroxypropyl methylcellulose, preferably incorporating pigments in the formulation, using standard techniques. Alternatively the tablets may be sugar coated, or enteric coated.

| Coating Suspension | % w/w |
|---|---|
| Hydroxypropyl methylcellulose | 10.0 |
| Opaspray | 5.0 |

| Coating Suspension | % w/w |
|---|---|
| Purified water to | 100.0++ |
| Opadry | 10.0 |
| Purified Water to | 100.00++ |

++The water does not appear in the final product.

COMPRESSION COATED TABLET

The active ingredient may also be formulated as a tablet core using conventional excipients such as fillers, binders, disintegrants and lubricants, and this core then compressed within an outer tablet (compression coated) using conventional excipients such as a pH-independent hydrophilic polymer, fillers, binders, disintegrants and lubricants. This outer coat may also contain active ingredient. The compression of both the core and the outer compression coat can be achieved using conventional tabletting machinery.

Such a dosage form can be designed so as to control the release of active ingredient as required.

EFFERVESCENT TABLET

|  | % w/w |
|---|---|
| Active ingredient | 8.75 |
| Sodium bicarbonate | 41.03 |
| Monosodium citrate anhydrous | 41.22 |
| Aspartame | 2.5 |
| Polyvinylpyrrolidone | 2.0 |
| Sodium benzoate | 3.0 |
| Orange flavour | 1.0 |
| Lemon flavour | 0.5 |
| Absolute alcohol for granulation | qs |

The active ingredient, anhydrous monosodium citrate, sodium bicarbonate and aspartame were mixed together and granulated by the addition of a solution of the polyvinylpyrrolidone in the alcohol. The granules obtained after mixing were dried and passed through a screen, and the resulting granules were then mixed with the sodium benzoate and flavourings. The granulated material was compressed into tablets using suitable diameter punches.

A rotary machine may also be used for tabletting.

LIQUID-FILLED CAPSULE FORMULATIONS FOR ORAL ADMINISTRATION

Liquid formulations were prepared by slow addition of active ingredient into the other ingredients with constant mixing.

| Example | A<br>% w/w | B<br>% w/w |
|---|---|---|
| Active ingredient | 18.2 | 18.2 |
| Oleic acid | 60.985 | 68.485 |
| Polyethylene glycol 600 | 7.3 | 7.3 |
| Propylene glycol | 6.0 | 6.0 |
| Polysorbate 80 | 7.5 | — |
| Ascorbyl palmitate | 0.015 | 0.015 |

The liquid formulations were filled into gelatin capsules, the size of the capsule being used and the filler determining the possible fill weight/volume and hence the dose of active ingredient per capsule.

POWDER-FILLED CAPSULES

|  | % w/w |
|---|---|
| Active ingredient | 24.5 |
| Lactose | 75.0 |
| Magnesium stearate | 0.5 |

The active ingredient was sieved and blended with the excipients. The mix was filled into hard gelatin capsules using suitable machinery. The dose is determined by the fill weight and the capsule size.

SYRUP

|  | mg/ 5 ml dose |
|---|---|
| Active ingredient | 49.0 |
| Hydroxypropyl methylcellulose (viscosity type 4000) | 22 5 |
| Buffer | qs |
| Flavour | qs |
| Colour | qs |
| Preservative | qs |
| Sweetener | qs |
| Purified water to | 5.0 ml |

The hydroxypropyl methylcellulose was dispersed in hot water, cooled and then mixed with an aqueous solution containing the active ingredient and the other components of the formulation. The resultant solution was adjusted to volume and mixed. The syrup was clarified by filtration.

SUSPENSION

|  | mg/ 5 ml dose |
|---|---|
| Active ingredient | 49.0 |
| Aluminium monostearate | 75.0 |
| Sweetening agent | qs |
| Flavour | qs |
| Colour | qs |
| Fractionated coconut oil to | 5.0 ml |

The aluminium monostearate was dispersed in about 90% of the fractionated coconut oil. The resulting suspension was heated to 115° C. while stirring and then cooled. The sweetening agent, flavour and colour were added and the active ingredient was suitably dispersed. The suspension was made up to volume with the remaining fractionated coconut oil and mixed.

SUB-LINGUAL TABLET

|  | % w/w |
|---|---|
| Active ingredient/lactose granule* | 49.0 |
| Compressible sugar | 50.5 |
| Magnesium stearate | 0.5 |

The active ingredient was sieved through a suitable sieve, blended with the excipients and compressed using suitable punches. Tablets of various strengths may be prepared by altering either the ratio of active ingredient to excipients or the compression weight and using punches to suit.

A rotary machine may also be used for tabletting.

SUPPOSITORY FOR RECTAL ADMINISTRATION

|  |  |
|---|---|
| Active ingredient | 49.0 mg |
| *Witepsol W32 | 1.0 g |

A suspension of the active ingredient in molten Witepsol was prepared and filled using suitable machinery, into 1 g size suppository moulds.

FOR INJECTION

|  | % w/v |
|---|---|
| Active ingredient | 1.0 |
| Water for injections B.P. to | 100 |

Sodium chloride may be added to adjust the tonicity of the solution and the pH may be adjusted to that of maximum stability and/or to facilitate soution of the active ingredient using dilute acid or alkali or by the addition of suitable buffer salts. Antioxidants and metal chelating salts may also be included. The solution is clarified, made up to final volume with water and the pH re-measured and adjusted if necessary.

The solution may be packaged for injection, for example by filling and sealing in ampoules, vials or syringes. The ampoules, vials or syringes mat be aseptically filled (e.g. the solution may be sterilised by filtration and filled into sterile ampoules under aseptic conditions) and/or terminally sterilised (e.g. by heating in an autoclave using one of the acceptable cycles). The solution may be packed under an inert atmosphere of nitrogen.

Preferably the solution is filled into ampoules, sealed by fusion of the glass and terminally sterilised.

FOR INHALATION

Inhalation Cartridges

|  | mg/cartridge |
|---|---|
| Active ingredient (micronised) | 0.56 |
| Lactose | 25.00 |

The active ingredient was micronised in a fluid energy mill to a fine particle size range prior to blending with normal tabletting grade lactose in a high energy mixer. The powder blend was filled into No 3 hard gelatin capsules on a suitable encapsulating machine. The contents of the cartridges were administered using a powder inhaler such as the Glaxo Rotahaler.

Metered Dose Pressurised Aerosol

| Suspension Aerosol | mg/metered dose | Per can |
|---|---|---|
| Active ingredient (micronised) | 0.280 | 73.92 mg |
| Oleic acid | 0.020 | 5.28 mg |
| Isopentane | 23.64 | 5.67 g |
| Tetrafluroethane | 61.25 | 14.70 g |

The active ingredient was micronised in a fluid energy mill to a fine particle size range. The oleic acid was mixed with the above at a temperature of 10–15° C. and the micronised drug was mixed into the solution with a high shear mixer. The suspension was metered into aluminium aerosol cans and suitable metering valves, delivering 85 mg of suspension, were crimped onto the cans and the dichlorodifluoromethane was pressure filled into the cans through the valves.

NASAL SPRAY

|  | % w/v |
|---|---|
| Active ingredient | 7.0 |
| Sodium chloride | 0.9 |
| Purified water to | 100 |
| Shot weight | 100 mg (equivalent to 7 mg active ingredient |

The active ingredient and sodium chloride were dissolved in a portion of the water, the solution made to volume with the water and the solution thoroughly mixed.

The pH may be adjusted to facilitate solution of the active ingredient, using acid or alkali and/or subsequently adjusted if necessary taking into account the pH for optimum stability. Alternatively, suitable buffer salts may be used. The solution may be preserved with, for example, benzalkanium chloride and phenylethyl alcohol, for a multi-dose nasal spray.

BIOLOGICAL RESULTS

The compounds of the present invention are thrombin inhibitors. The results below illustrate the thrombin activity of a range of of compounds of formula (I) using the previously described biological method:

| Example no. | IC$_{50}$ nm |
|---|---|
| 1 | 8 |
| 6 | 5 |
| 9 | 7 |
| 13 | 15 |
| 17 | 14 |
| 20 | 9 |
| 29 | 62 |
| 37 | 17 |
| 40 | 9 |
| 41 | 28 |
| 47 | 61 |
| 49 | 38 |
| 55 | 50 |
| 58 | 107 |
| 72 | 63 |
| 90 | 22 |
| 92 | 15 |
| 91 | 34 |
| 99 | 40 |
| 118 | 1o |
| 109 | 140 |
| 124 | 28 |
| 128 | 41 |
| 138 | 91 |

What is claimed is:
1. A compound represented by formula (I)

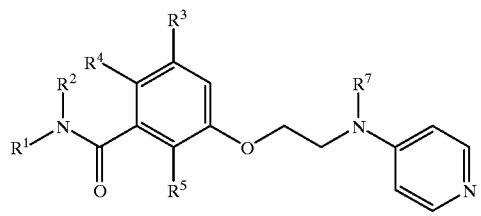

(I)

where $R^1$ and $R^2$ independently represent a group

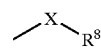

or $R^1$ and $R^2$ together form a $C_{3-7}$ heterocycloalkyl or heterocycloalkenyl group which may be optionally substituted by $C_{1-6}$ alkyl, $C_{1-4}$ alkoxy, halogen, carboxylic acid or a $C_{1-4}$ carboxylic acid ester group;

$R^3$ represents hydrogen, $C_{1-3}$ alkyl, halogen, or $C_{1-2}$ alkoxy;

$R^4$, $R^5$ and $R^6$ independently represent hydrogen, or halogen;

$R^7$ represents hydrogen or $C_{1-6}$alkyl;

R8 represents hydrogen, C3–7 cycloalkyl, C3–7 cycloalkenyl, C3–7 heterocycloalkyl, C3–7 heterocycloalkenyl, aryl, or heteroaryl, which groups are optionally substituted by one or more groups selected from halogen, hydroxy, CN, $C_{1-6}$ alkyl, $C_{1-6}$ alkoxy, $C_{1-6}$ acyloxy, $NR^9R^{10}$, $NHCOR^{11}$, $NHSO_2R^{12}$, $COR^3$, $CO_2R^{14}$, $CONR^{15}R^{16}$, and $SO_2NHR^{17}$;

X represents a bond, a $C_{1-6}$alkyl chain, or a $C_{3-6}$alkenyl chain, where one or two nitrogen, oxygen, or sulfur atoms may be optionally contained within each chain, and the chains are optionally substituted by one or more groups selected from halogen, hydroxy, CN, $C_{1-6}$alkyl, C$_{1-6}$alkoxy, C$_{1-6}$acyloxy, NR$^9$R$^{10}$, NHCOR$^{11}$, NHSO$_2$R$^{12}$, COR$^{13}$, CO$_2$R$^{14}$, CONR$^{15}$R$^{16}$, and SO$_2$NHR$^{17}$;

R$^9$–R$^{17}$ represent hydrogen, C$_{1-6}$alkyl, or R$^9$ and R$^{10}$ or R$^{15}$ and R$^{16}$ form a C$_{3-7}$ heterocycloalkyl ring, or R$^{12}$ additionally may represent trifluoromethyl;

or pharmaceutically acceptable salt or solvate thereof.

2. A compound according to claim 1 where R$^1$ represents a group

where X represents a bond or C$_{1-6}$ alkyl group and R$^8$ represents hydrogen, C$_{3-7}$ cycloalkyl, aryl, or heteroaryl.

3. A compound according to claim 2 where X represents a bond and R$^8$ represents phenyl optionally substituted by one or more halogen groups, or C$_{3-7}$ cycloalkyl.

4. A compound according to claim 2 or claim 3 where X represents a C$_{1-6}$ alkyl group and R$^8$ represents hydrogen, cycloalkyl, or heteroaryl.

5. A compound according to claim 1 where R$^2$ represents a group

and X represents C$_{3-6}$ alkenyl, or a C$_{1-6}$ alkyl which optionally contains an oxygen group within the chain and is optionally substituted by a group selected from hydroxy, C$_{1-6}$ alkoxy, NHSO2R$^{12}$ CO$_2$R$^{14}$, CONR$^{15}$R$^{16}$, C$_{1-6}$ acyloxy or SO$_2$NHR$^{17}$, and R$^8$ represents hydrogen, C$_{3-7}$ heterocycdoalkyl, aryl optionally substituted by CO$_2$R$^{14}$, or heteroaryl optionally substituted by hydroxy or C$_{1-6}$ alkyl.

6. A compound according to claim 1 where R$^3$ represents C$_{1-3}$ alkyl or halogen.

7. A compound according to claim 1 where R$^4$, R$^5$ and R$^6$ represent hydrogen or halogen.

8. A compound according to claim 1 where R$^7$ is hydrogen.

9. A compound according to claim 1 represented by formula (IA)

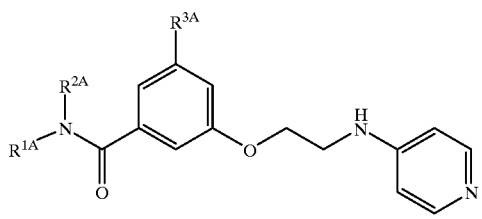

(IA)

where

R$^{1A}$ represents a group

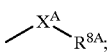

X$^A$ represents a bond, C$_{1-6}$ alkyl:

R$^{8A}$ represents hydrogen, C$_{3-7}$ cycloalkyl, aryl optionally substituted by halogen, or heteroaryl;

R$^{2A}$ represents a group

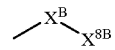

where

X$^B$ represents C$_{1-6}$ alkyl optionally substituted by CO$_2$$^{R14A}$;

R$^{8B}$ represents hydrogen, phenyl substituted by CO$_2$R$^{14A}$, oxadiazole substituted by a hydroxy group, or an unsubstituted C-linked tetrazole group;

R$^{3A}$ represents C$_{1-3}$ alkyl, or halogen;

or pharmaceutically acceptable salt or solvate thereof.

10. N-Cyclohexyl-3,N-dimethyl-5-[2-(pyridin-4-ylamino)-ethoxy]-benzamide;

3-Chloro-N-cycohexyl-N-methyl-5-[2-(pyridin-4-ylamino)-ethoxy]-benzamide;

3-Bromo-N-cyclohexyl-N-methyl-5-[2-(pyridin-4-ylamino)-ethoxy]-benzamide;

N-Allyl-3-chloro-N-cyclohexyl-5-[2-(pyridin-4-ylamino)-ethoxy]-benzamide;

N-Allyl-3-bromo-N-cyclohexyl-5-[2-(pyridin-4-ylamino)-ethoxy]-benzamide;

({3-Chloro-5-[2-(pyridin-4-ylamino)-ethoxy]-benzoyl}-cyclohexyl-amino)-acetic acid;

({3-Bromo-5-[2-(pyridin-4-ylamino)-ethoxy]-benzoyl}-cyclohexyl-amino)-acetic acid;

N-Allyl-3-chloro-N-cyclopentyl-5-[2-(pyridin-4-ylamino)-ethoxy]-benzamide;

N-Allyl-3-bromo-N-cyclopentyl-5-[2-(pyridin-4-ylamino)-ethoxy]-benzamide;

3-Chloro-N-propyl-5-[2-(pyridin-4-ylamino)-ethoxy]-N-(tetrahydro-pyran-4-yl)-benzamide;

3-Bromo-N-propyl-5-[2-(pyridin-4-ylamino)-ethoxy]-N-(tetrahydro-pyran-4-yl)-benzamide;

3-Chloro-N-propyl-N-pyridin-3-yl-5-[2-(pyridin-4-ylamino)-ethoxy]-benzamide;

3-Bromo-N-propyl-N-pyridin-3-yl-5-[2-(pyridin-4-ylamino)-ethoxy]-benzamide;

3-Chloro-N-(3,5-difluorophenyl)-N-propyl-5-[2-(pyridin-4-ylamino)-ethoxy]-benzamide;

3-Bromo-N-(3,5-difluorophenyl)-N-propyl-5-[2-(pyridin-4-ylamino)-ethoxy]-benzamide;

2-[{3-Chloro-5-[2-(pyridin-4-ylamino)-ethoxy]-benzoyl}-(2,4-difluoro-benzyl)-amino]-butyric acid;

4-[({3-Chloro-5-[2-(pyridin-4-ylamino)-ethoxy]-benzoyl}-isobutyl-amino)-methyl]-benzoic acid;

4-[2-({3-Chloro-5-[2-(pyridin-4-ylamino)-ethoxy]-benzoyl}-isobutyl-amino)-ethyl]-benzoic acid;

3-Chloro-N-cyclopentyl-5-[2-(pyridin-4-ylamino)-ethoxy]-N-(3-trifluoromethanesulfonylamino-propyl)-benzamide;

3-Chloro-N-isopropyl-N-methyl-5-[2-(pyridin-4-ylamino)-ethoxy]-benzamide;

N-[2-(3-Amino-[1,2,4]oxadiazol-5-yl)-ethyl]-3-chloro-N-isopropyl-5-[2-(pyridin-4-ylamino)-ethoxy]-benzamide;

N-(2-Carbamoyl-ethyl)-N-isopropyl-3-methyl-5-[2-(pyridin-4-ylamino)-ethoxy]-benzamide;

N-(2-Carbamoyl-ethyl)-3-chloro-N-cyclopropylmethyl-5-[2-(pyridin-4-ylamino)-ethoxy]-benzamide;

N-(2-Carbamoyl-ethyl)-3-chloro-5-[2-(pyridin-4-ylamino)-ethoxy]-N-tetrahydrofuran-2-ylmethyl)-benzamide;

N-(2-Carbamoyl-ethyl)-3-chloro-N-(2,2-dimethyl-propyl)-5-[2-(pyridin-4-ylamino)-ethoxy]-benzamide;

N-(2-Carbamoyl-ethyl)-3-chloro-N-isopropyl-5-[2-(pyridin-4-ylamino)-ethoxy]-benzamide;

N-(2-Carbamoyl-ethyl)-3-chloro-N-isobutyl-5-[2-(pyridin-4-ylamino)-ethoxy]-benzamide;

6-[{3-Chloro-5-[2-(pyridin-4-ylamino)-ethoxy]-benzoyl}-(2-fluoro-benzyl)-amino]-hexanoic acid;

6-({3-Chloro-5-[2-(pyridin-4-ylamino)-ethoxy]-benzoyl}-isobutyl-amino)-hexanoic acid;

6-[{3-Chloro-5-[2-(pyridin-4-ylamino)-ethoxy]-benzoyl}-(2-methoxy-ethyl)-amino]-hexanoic acid;

6-[{3-Chloro-5-(2-(pyridin-4-ylamino)-ethoxy]-benzoyl}-cyclohexylmethyl-amino)-hexanoic acid;

6-[{3-Chloro-5-[2-(pyridin-4-ylamino)-ethoxy]-benzoyl}-(3-fluoro-benzyl)-amino]-hexanoic acid;

6-({3-Chloro-5-[2-(pyridin-4-ylamino)-ethoxy]-benzoyl}-pyridin-4-ylmethyl-amino)-hexanoic acid;

N-(5-Carbamoyl-pentyl)-3-chloro-N-furan-2-ylmethyl-5-[2-(pyridin-4-ylamino)-ethoxy]-benzamide;

N-(5-Carbamoyl-pentyl)-3-chloro-5-[2-(pyridin-4-ylamino)-ethoxy]-N-(2,2,2-trifluoroethyl)-benzamide;

N-(5-Carbamoyl-pentyl)-3-chloro-N-(2-fluoro-benzyl)-5-[2-(pyridin-4-ylamino)-ethoxy]-benzamide;

N-(5-Carbamoyl-pentyl)-3-chloro-N-(2-methoxy-ethyl)-5-[2-(pyridin-4-ylamino)-ethoxy]-benzamide;

N-(5-Carbamoyl-pentyl)-3-chloro-N-cyclohexylmethyl-5-[2-(pyridin-4-ylamino)-ethoxy]-benzamide;

N-(5-Carbamoyl-pentyl)-3-chloro-N-isobutyl-5-[2-(pyridin-4-ylamino)-ethoxy]-benzamide;

N-(5-Carbamoyl-pentyl)-3-chloro-5-[2-(pyridin-4-ylamino)-ethoxy]-N-thiophen-2-ylmethyl-benzamide;

1-{3-Chloro-5-[2-(pyridin-4-ylamino)-ethoxy]-benzoyl}-piperidine-2-carboxylic acid;

4-({3-Chloro-5-[2-(pyridin-4-ylamino)-ethoxy]-benzoyl}-cyclobutyl-amino)-butyric acid;

4-({3-Chloro-5-[2-(pyridin-4-ylamino)-ethoxy]-benzoyl}-furan-2-ylmethyl-amino)-butyric acid;

4-[{3-Chloro-5-[2-(pyridin-4-ylamino)-ethoxy]-benzoyl}-(3-fluoro-benzyl)-amino]-butyric acid;

{3-Chloro-5-[2-(pyridin-4-ylamino)-ethoxy-phenyl}-(2-methyl-piperidin-1-yl)-methanone;

3-Chloro-N-(2-diethylcarbamoyl-ethyl)-N-isopropyl-5-[2-(pyridin-4-ylamino)-ethoxy]-benzamide;

3-Chloro-N-isopropyl-N-(3-methanesufonylamino-propyl)-5-[2-(pyridin-4-ylamino)-ethoxy]-benzamide;

3-Chloro-N-isopropyl-N-[3-(propane-1-sulfonylamino)-propyl]-5-[2-(pyridin-4-ylamino)-ethoxy]-benzamide;

3-Chloro-N-isopropyl-N-(3-oxo-3-piperidin-1-yl-propyl)-5-[2-(pyridin-4-ylamino)-ethoxy]-benzamide;

3-Chloro-N-[2-(ethyl-methyl-carbamoyl)-ethyl]-N-isopropyl-5-[2-(pyridin-4-ylamino)-ethoxy]-benzamide;

3-Chloro-N-isopropyl-N-(3-oxo-3-pyrrolidin-1-yl-propyl)-5-[2-(pyridin-4-ylamino)-ethoxy]-benzamide;

3-Chloro-N-isopropyl-N-(3-morpholin-4-yl-3-oxo-propyl)-5-[2-(pyridin-4-ylamino)-ethoxy]-benzamide mixture with 3-({3-chloro-5-[2-(pyridin-4-ylamino)-ethoxy]-benzoyl}-isopropyl-amino)-propionic acid (1:2);

N-(2-tert-Butylcarbamoyl-ethyl)-3-chloro-N-isopropyl-5-[2-(pyridin-4-ylamino)-ethoxy]-benzamide;

3-Chloro-N-[2-(2,2-dimethyl-propylcarbamoyl)-ethyl]-N-isopropyl-5-[2-(pyridin-4-ylamino)-ethoxy]-benzamide;

3-Chloro-N-isopropyl-N-(3-oxo-3-thiomorpholin-4-yl-propyl)-5-[2-(pyridin-4-ylamino)-ethoxy]-benzamide;

3-Chloro-N-isopropyl-N-(3-oxo-3-thiazolidin-3-yl-propyl)-5-[2-(pyridin-4-ylamino)-ethoxy]-benzamide;

3-Chloro-N-(3-ethanesulfonylamino-propyl)-N-isopropyl-5-[2-(pyridin-4-ylamino)-ethoxy]-enzamide;

3-Chloro-N-isopropyl-N-[3-propane-2-sulfonylamino)-propyl]-5-[2-(pyridin-4-ylamino)-ethoxy]-benzamide;

3-Chloro-N-(4-fluoro-phenyl)-5-[2-(pyridin-4-ylamino)-ethoxy]-N-(3-[1,2,4]triazol-1-yl-propyl)-benzamide;

3-Chloro-N-cyclopentyl-5-[2-(pyridin-4-ylamino)-ethoxy]-N-(2-1,2,4]triazol-1-yl-ethyl)-benzamide;

3-Chloro-N-cyclopentyl-5-[2-(pyridin-4-ylamino)-ethoxy]-N-(4-[1,2,4]triazol-1-yl-butyl)-benzamide;

3-Chloro-N-(4-fuoro-phenyl)-5-[2-(pyridin-4-ylamino)-ethoxy]-N-(3-tetrazol-2-yl-propyl)-benzamide;

3-Chloro-N-(3-fluoro-phenyl)-5-[2-(pyridin-4-ylamino)-ethoxy]-N-(3-tetrazol-2-yl-propyl)-benzamide;

3-Chloro-(2-fluoro-phenyl)-5-[2-(pyridin -4-ylamino)-ethoxy-]-N-(3-tetrazol-2-yl-propyl)-benzamide;

3-Chloro-N-phenyl-5-[2-(pyridin-4-ylamino)-ethoxy]-N-(2tetrazol-2-yl-ethyl)-benzamide;

3-Chloro-N-phenyl-5-[2-(pyridin-4-ylamino)-ethoxy]-N-(2-[1,2,3]triazol-2-yl-ethyl)-benzamide;

3-Chloro-N-phenyl-5-[2-(pyridin-4-ylamino)-ethoxy]-N-(2-(pyridin-2-yloxy)-ethyl]-benzamide;

3-Chloro-N-isopropyl-N-(2-methoxy-ethyl)-5-[2-(pyridin-4-ylamino)-ethoxy]-benzamide;

6-({3-Chloro-5-[2-(pyridin-4-ylamino)-ethoxy]-benzoyl}-thiophen-2-ylmethyl-amino)-hexanoic acid;

6-[{3-Chloro-5-[2-(pyridin-4-ylamino)-ethoxy]-benzoyl}-(2-methyl-butyl)-amino]-hexanoic acid;

{3-Chloro-5-[2-(pyridin-4-ylamino)-ethoxy]-phenyl}-(2,5-dimethyl-pyrrolidin-1-yl)-methanone;

4-({3-Chloro-5-[2-(pyridin-4-ylamino)-ethoxy]-benzoyl}-naphthalen-1-ylmethyl-amino)-butyric acid;

4-[{3-Chloro-5-[2-(pyridin-4-ylamino)-ethoxy]-benzoyl}-(1-methyl-1H-benzoimidazol-2-yl)-amino]-butyric acid;

3-Chloro-N-isopropyl-5-[2-(pyridin-4-ylamino)-ethoxy]-N-(3-trifluoromethanesulfonylamino-propyl)-benzamide;

N-(3-Amino-propyl)-3-chloro-N-isopropyl-5-[2-(pyridin-4-ylamino)-ethoxy]-benzamide;

({3-Chloro-5-[2-(pyridin-4-ylamino)-ethoxy]-benzoyl}-cyclopentyl-amino)-acetic acid;

3-Chloro-N-cyclopentyl-N-propyl-5-[2-(pyridin-4-ylamino)-ethoxy]-benzamide;

3-Chloro-N-cyclopentyl-N-(3-hydroxy-propyl)-5-[2-(pyridin-4-ylamino)-ethoxy]-benzamide;

3-Chloro-N-propyl-5-[2-(pyridin-4-ylamino)-ethoxy]-N-(tetrahydro-pyran-4-yl)-benzamide;

3-Chloro-N-cyclopentyl-N-(2,3-dihydroxy-propyl)-5-[2-(pyridin-4-ylamino)-ethoxy]-benzamide;

3-Chloro-N-cyclopentyl-N-(3-morpholin-4-yl-propyl)-5-[2(pyridin-4-ylamino)-ethoxy]-benzamide;

4-({3-Chloro-5-[2-(pyridin-4-ylamino)-ethoxy]-benzoyl}-cyclopentyl-amino)-butyric acid ethyl ester;

3-Chloro-N-cyclopentyl-5-[2-(pyridin-4-ylamino)-ethoxy]-N-(3-pyrrolidin-1-yl-propyl)-benzamide;

N-(3-Carbamoyl-propyl)-3-chloro-N-cyclopentyl-5-[2-(pyridin-4-ylamino)-ethoxy]-benzamide;

N-(2-Carbamoyl-ethyl)-3-chloro-N-cyclopentyl-5-[2-(pyridin-4-ylamino)-ethoxy]-benzamide;

N-Carbamoylmethyl-3-chloro-N-cyclopentyl-5-[2-(pyridin-4-ylamino)-ethoxy]-benzamide;

3-Chloro-N-ethyl-N-phenyl-5-[2-(pyridin-4-ylamino)-ethoxy]-benzamide;

N-(2-Carbamoyl-ethyl)-3-chloro-N-cyclopropyl-5-[2-(pyridin-4-ylamino)-ethoxy]-benzamide;

3-Chloro-N,N-dipropyl-5-[2-(pyridin-4-ylamino)-ethoxy]-benzamide;

4-({3-Chloro-5-[2-(pyridin-4-ylamino)-ethoxy]-benzoyl}-cyclopentyl-amino)-butyric acid;

N-(2-Carbamoyl-ethyl)-3-chloro-N-phenyl-5-[(2-(pyridin-4-ylamino)-ethoxy]-benzamide;

N-(2-Carbamoyl-ethyl)-3-chloro-N-(2-chloro-phenyl)-5-[2-(pyridin-4-ylamino)-ethoxy]-benzamide;

N-(2-Carbamoyl-ethyl)-3-chloro-N-(2-fluoro-phenyl)-5-[2-(pyridin-4-ylamino)-ethoxy]-benzamide;

4-[{3-Chloro-5-[2-(pyridin-4-ylamino)-ethoxy]-benzoyl}-(2-fluoro-phenyl)amino]-butyric acid methyl ester;

4-[{3-Chloro-5-[2-(pyridin-4-ylamino)-ethoxy]-benzoyl}-(2-fluoro-phenyl)-amino]-butyric acid;

3-Chloro-N-(2-fluoro-phenyl)-N-(4-oxo-4-pyrrolidin-1-yl-butyl)-5-[2-(pyridin-4-ylamino)-ethoxy]-benzamide;

N-(3-Carbamoyl-propyl)-3-chloro-N-(2-fluoro-phenyl)-5-]2-(pyridin-4-ylamino)-ethoxy]-benzamide;

4-((2-Carbamoyl-phenyl)-{3-chloro-5-[2-(pyridin-4-ylamino)-ethoxy]-benzoyl}-amino)-butyric acid methyl ester;

4-((2-Carbamoyl-phenyl)-{3-chloro-5-[2-(pyridin-4-ylamino)-ethoxy]-benzoyl}-amino)-butyric acid;

3-Chloro-N-(2-fluoro-phenyl)-5-[2-(pyridin-4-ylamino)-ethoxy]-N-[3-(1H-tetrazol-5-yl)-propyl]-benzamide;

3-Chloro-N-[2-(2,3-dihydroxy-propoxy)-ethyl]-N-(2-fluoro-phenyl)-5-[2-(pyridin-4-ylamino)-ethoxy]-benzamide;

(R)-1-{3-[{3-Chloro-5-[2-(pyridin-4-ylamino]-ethoxy-benzoyl}-(2-fluoro-phenyl)-amino]-propyl}-pyrrolidine-2-carboxylic acid;

3-Chloro-N-phenyl-5-[2-(pyridin-4-ylamino)-ethoxy]-N-(2-sulfamoyl-ethyl)-benzamide;

3-Chloro-N-[2-(ethyl-methyl-carbamoyl)-ethyl]-N-phenyl-5-[2-(pyridin-4-ylamino)-ethoxy]-benzamide;

3-Chloro-N-[2-(ethyl-methyl-carbamoyl)-ethyl]-N-phenyl-5-[2-(pyridin-4-ylamino)-ethoxy]-benzamide;

N-(2-tert-Butylcarbamoyl-ethyl)-3-chloro-N-phenyl-5-[2-(pyridin-4-ylamino)-ethoxy]-benzamide;

3-Chloro-N-[2-(2,2-dimethyl-propylcarbamoyl)-ethyl]-N-phenyl-5-[2-(pyridin-4-ylamino)-ethoxy]-benzamide;

3-Chloro-N-(3-oxo-3-thiomorpholin-4-yl-propyl)-N-phenyl-5-[2-(pyridin-4-ylamino)-ethoxy]-benzamide;

3-Chloro-N-(3-oxo-3-thiazolidin-3-yl-propyl)-N-phenyl-5-[2-(pyridin-4-ylamino)-ethoxy]-benzamide;

N-tert-Butyl-3-chloro-5-[2-(pyridin-4-ylamino)-ethoxy]-benzamide;

3-Chloro-N-isopropyl-N-[2-(1-methyl-1H-tetrazol-5-yl)-ethyl]-5-[2-(pyridin-4-ylamino)-ethoxy]-benzamide;

3-Chloro-N-(3,5-difluoro-phenyl)-N-propyl-5-[2-(pyridin-4-ylamino)-ethoxy]-benzamide;

3-Chloro-N-(3-morpholin-4-yl-propyl)-5-[2-(pyridin-4-ylamino)-ethoxy]-N-(tetrahydro-pyran-4-yl)-benzamide;

3-Chloro-5-[2-(pyridin-4-ylamino)-ethoxy]-N-(3-pyrrolidin-1-yl-propyl)-N-(tetrahydro-pyran-4-yl)-benzamide;

N-(2-Carbamoyl-ethyl)-3-chloro-N-(1-propyl-butyl)-5-[2-(pyridin-4-ylamino)-ethoxy]-benzamide;

3-Chloro-N-cyclopentyl-N-(4-oxo-4-pyrrolidin-1-yl-butyl)-5-[2-(pyridin-4-ylamino)-ethoxy]-benzamide;

3-Chloro-N-ethyl-N-(2-fluoro-phenyl)-5-[2-(pyridin-4-ylamino)-ethoxy]-benzamide;

3-Chloro-N-propyl-5-[2-(pyridin-4-ylamino)-ethoxy]-N-[1,3,4]thiadiazol-2-yl-benzamide;

3-Chloro-N-propyl-5-[2-(pyridin-4-ylamino)-ethoxy]-N-thiazol-2-yl-benzamide;

3-Chloro-N-[2-(2,3-dihydroxy-propoxy)-ethyl]-N-phenyl-5-[2-(pyridin-4-ylamino)-ethoxy]-benzamide;

N-(2-tert-Butylsulfamoyl-ethyl)-3-chloro-N-phenyl-5-[2-(pyridin-4-ylamino)-ethoxy]-benzamide;

3-Chloro-N-(2-isopropylsulfamoyl-ethyl)-N-phenyl-5-[2-(pyridin-4-ylamino)-ethoxy]-benzamide;

3-Chloro-N-isopropyl-5-[2-(pyridin-4-ylamino)-ethoxy]-N-[2-(pyridin-2-yloxy)-ethyl]-benzamide;

3-Chloro-N-[2-(2,3-dihydroxy-propoxy)-ethyl]-N-(4-fluoro-phenyl)-5-[2-(pyridin-4-ylamino)-ethoxy]-benzamide;

3-Chloro-N-cyclopentyl-5-[2-(pyridin-4-ylamino)-ethoxy]-N-[2-(1H-tetrazol-5-yl)-ethyl]-benzamide;

3-Chloro-N-isopropyl-5-[2-(pyridin-4-ylamino)-ethoxy]-N-(2-[1,2,4]triazol-1-yl-ethyl)-benzamide;

3-Chloro-N-[2-(3-methyl-but-2-yl-carbamoyl)-ethyl]-N-isopropyl-5-[2-(pyridin-4-ylamino)-ethoxy]-benzamide;

3-Chloro-N-[2-(3,3-dimethyl-but-2-yl-carbamoyl)-ethyl]-N-isopropyl-5-[2-(pyridin-4-ylamino)-ethoxy]-benzamide;

3-Chloro-N-[2-(5-hydroxy-[1,2,4]oxadiazol-3-yl)-ethyl]-N-isopropyl-5-[2-(pyridin-4-ylamino)-ethoxy]-benzamide;

N-tert-Butyl-N-(2-tert-butylcarbamoyl-ethyl)-3-chloro-5-[2-(pyridin-4-ylamino)-ethoxy]-benzamide;

N-(2-tert-Butylcarbamoyl-ethyl)-3-chloro-N-cyclobutyl-5-[2-(pyridin-4-ylamino)-ethoxy]-benzamide;

3-Chloro-N-cyclobutyl-N-[2-(2,2-dimethyl-propylcarbamoyl)-ethyl]-5-[2-(pyridin-4-ylamino)-ethoxy]-benzamide;

N-(2-Carbamoyl-ethyl)-3-chloro-N-cyclobutyl-5-[2-(pyridin-4-ylamino)-ethoxy]-benzamide;

3-Chloro-N-isopropyl-5-[2-(pyridin-4-ylamino)-ethoxy]-N-(2-sulfamoyl-ethyl)-benzamide;

3-Chloro-N-(2,2-dimethyl-propylsulfamoyl-ethyl)-N-isopropyl-5-[2-(pyridin-4-ylamino)-ethoxy]-benzamide;

6-({3-Chloro-5-[2-(pyridin-4-ylamino)-ethoxy]-benzoyl}isopropyl-amino)-hexanoic acid;

N-(2-tert-Butylcarbamoyl-ethyl)-N-isopropyl-3-methyl-5-[2-(pyridin-4-ylamino)-ethoxy]-enzamide;

N-(5-tert-Butylcarbamoyl-pentyl)-N-isopropyl-3-methyl-5-[2-(pyridin-4-ylamino)-ethoxy]-benzamide;

3-Chloro-N-[5-(2,2-dimethyl-propylcarbamoyl)-pentyl]-N-isopropyl-5-[2-(pyridin-4-ylamino)-ethoxy]-benzamide;

N-(5-Carbamoyl-pentyl)-N-isopropyl-3-methyl-5-[2-pyridin-4-ylamino)-ethoxy]-benzamide;

3-Chloro-N-(2-(4-tert-butylphenyl)-ethyl)-N-isopropyl-5-[2-(pyridin-4-ylamino)-ethoxy]-benzamide;

3-Chloro-N-isopropyl-5-[2-(pyridin-4-ylamino)ethoxy]-N-[3-(2,2-dimethyl-propionylamino)-propyl]-benzamide;

3-Chloro-N-isopropyl-5-(2-(pyridin-4-ylamino)ethoxy]-N-[3-(3,3-dimethyl-butyrylamino)-propyl]-benzamide;

3-Chloro-N-[2-(1,1-dimethyl-propylcarbamoyl)-ethyl]-N-isopropyl-5-[2-(pyridin-4-ylamino)-ethoxy]-benzamide;

N-{2-(2,2-dimethylpropylcarbamoyl)-ethyl}-N-isopropyl-3-methyl-5-[2-(pyridin-4-ylamino)-ethoxy]-benzamide;

3-(Isopropyl-{3-methyl-5-[2-(pyridin-4-ylamino)-ethoxy]-benzoyl}-amino)-propionic acid;

3-(Isopropyl-{3-methyl-5-[2-(pyridin-4-ylamino)-ethoxy]-benzoyl}-amino)-propionic acid methyl ester;

N-(5-tert-Butylcarbamoyl-pentyl)-3-chloro-N-isopropyl-5-[2-(pyridin-4-ylamino)-ethoxy]-benzamide;

6-({3-Methyl-5-[2-(pyridin-4-ylamino)-ethoxy]-benzoyl}-isopropyl-amino)-hexanoic acid;

N-(2-Cyano-ethyl)-N-isopropyl-3-methyl-5-[2-(pyridin-4-ylamino)-ethoxy]-benzamide;

3-Chloro-N,N-diisopropyl-5-[2-(pyridin-4-ylamino)-ethoxy]-benzamide;

3-Chloro-N-isopropyl-N-(3-oxo-3-thiazolidin-3-yl-propyl)-5-[2-(pyridin-4-ylamino)-ethoxy]-benzamide;

or pharmaceutically acceptable salt or solvate thereof.

11. 3-Chloro-N[2-(5-hydroxy-[1,2,4]oxadiazol-3-yl)-ethyl)N-isopropyl-5-[2[(pyridin-4-ylamino)-ethoxyl]-benzamide;

4-({3-Chloro-5-[2-(pyridin-4-ylamino)-ethoxy]-benzoyl}-clobutyl-amino)-butyric acid;

6-({3-Chloro-5-[2-(pyridin-4-ylamino)-ethoxy]-benzoyl}-isobutyl-amino)-hexanoic acid;

4-[({3-Chloro-5-[2-(pyridin-4-ylamino)-ethoxy]-benzoyl}-isobutyl-amino)-methyl]-benzoic acid 4-[2-({3-Chloro-5-[2-(pyridin-4-ylamino)-ethoxy]-benzoyl}-isobutyl-amino)-ethyl]-benzoic acid;

4-({3-Chloro-5-[2-(pyridin-4-ylamino)-ethoxy]-benzoyl}-cyclopentyl-amino)-butyric acid ethyl ester;

4-({3-Chloro-5-(pyridin-4-ylamino)-ethoxy]-benzoyl}-cyclopentyl-amino)-butyric acid;

3-Chloro-N-cyclopentyl-5-[2-(pyridin-4-ylamino)-ethoxy]-N-[2-(1H-tetrazol-5-yl)-ethyl]-benzamide;

6-({3-Chloro-5-[2-(pyridin-4-ylamino)-ethoxy]-benzoyl}-cyclohexylmethyl-amino)-hexanoic acid;

6-({3-Chloro-5-[2-(pyridin-4-ylamino)-ethoxy]benzoyl}-thiophen-2-ylmethyl-amino)-hexanoic acid;

4-[{3-Chloro-5-[2-(pyridin-4-ylamino)-ethoxy]-benzoyl}-(2-fluoro-phenyl)-amino]-butyric acid methyl ester;

4-[{3-Chloro-5-[2-(pyridin-4-ylamino)-ethoxy]-benzoyl}-(2-fluoro-phenyl)-amino]-butyric acid;

3-Chloro-N-(2-fluoro-phenyl)-5-[2-(pyridin-4-ylamino)-ethoxy]-N-[3-(1H-tetrazol-5-yl)-propyl]-benzamide;

or pharmaceutically acceptable salt or solvate thereof.

12. A method of treatment of a mammal, suffering from a condition susceptible of amelioration by a thrombin inhibitor comprising administration of an effective amount of a compound according to claim 1 or a pharmaceutically acceptable derivative thereof.

13. A pharmaceutical composition comprising a compound according to claim 1 or a pharmaceutically acceptable derivative thereof together with one or more pharmaceutically acceptable carriers.

14. A process for preparing a compound of formula (I) as claimed in claim 1, or a pharmaceutically acceptable derivative thereof which comprises:

(A), reaction of a compound of formula (II) with a compound of formula (III),

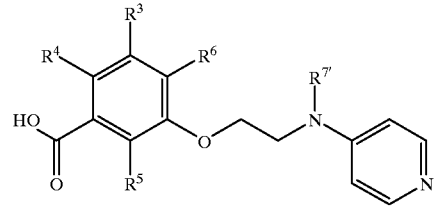

(II)

(III)

where R<sup>7'</sup> represents R⁷ or a suitable protecting group, (B), reaction of compounds of formula (XIV) and (XV)

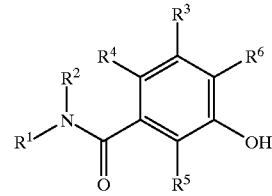

(XIV)

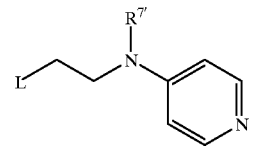

(XV)

where L is a suitable leaving group, in the presence of a suitable base, or (C), reaction of compounds of formula (I) with compounds of formula (III) which are bound to a solid phase resin via a carboxamide or carboxylate functional group on R⁸ or X, by amide coupling techniques, followed by deprotection of any protecting groups and cleavage from the resin under suitable conditions.

* * * * *